US012613173B2

(12) United States Patent
Alhusban et al.

(10) Patent No.: US 12,613,173 B2
(45) Date of Patent: Apr. 28, 2026

(54) APPARATUS AND METHOD FOR EVALUATING PHYSICAL STRENGTH OR ROBUSTNESS OF SOLID PHARMACEUTICAL DOSAGE FORMS BASED ON AN IMPACT STRIKE TEST

(71) Applicant: ASTRAZENECA AB, Södertälje (SE)

(72) Inventors: Farhan Alhusban, Cambridge (GB);
Brian Clark, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 329 days.

(21) Appl. No.: 18/552,768

(22) PCT Filed: Apr. 8, 2022

(86) PCT No.: PCT/US2022/024010
§ 371 (c)(1),
(2) Date: Sep. 27, 2023

(87) PCT Pub. No.: WO2022/217043
PCT Pub. Date: Oct. 13, 2022

(65) Prior Publication Data
US 2024/0167926 A1 May 23, 2024

Related U.S. Application Data

(60) Provisional application No. 63/173,102, filed on Apr. 9, 2021.

(51) Int. Cl.
*G01N 3/303* (2006.01)
*G01N 3/04* (2006.01)
*G01N 33/15* (2006.01)

(52) U.S. Cl.
CPC ............. *G01N 3/303* (2013.01); *G01N 33/15* (2013.01); *G01N 2203/001* (2013.01);
(Continued)

(58) Field of Classification Search
CPC .......... G01N 3/20; G01N 3/303; G01N 33/15; G01N 2203/001; G01N 2203/0033;
(Continued)

(56) References Cited

U.S. PATENT DOCUMENTS

| | | | | |
|---|---|---|---|---|
| 4,640,120 | A | * 2/1987 | Garritano | G01N 3/303 73/12.13 |
| 5,165,287 | A | * 11/1992 | Manahan, Sr. | G01N 3/20 73/826 |
| 2012/0240688 | A1* | 9/2012 | Myers | G01N 3/08 73/826 |

FOREIGN PATENT DOCUMENTS

| | | |
|---|---|---|
| DE | 2941483 A1 | 5/1980 |
| EP | 1061353 A2 | 12/2000 |

(Continued)

OTHER PUBLICATIONS

Japanese Office Action for JP Appl. No. 2023-561648 dated Jul. 24, 2024 (3 pages).
(Continued)

*Primary Examiner* — Brandi N Hopkins
(74) *Attorney, Agent, or Firm* — MEDLER FERRO WOODHOUSE & MILLS PLLC

(57) ABSTRACT

A solid pharmaceutical dosage form testing apparatus and a method are presented. The solid pharmaceutical dosage form testing apparatus includes a striker component, an impact platform, a sensor data acquisition system, and a solid dosage form placement mechanism. The solid dosage form placement mechanism has first and second push components that are movable toward each other to position a solid dosage form at an impact site. The method includes performing an impact strike test on a first plurality of solid dosage forms, and measuring a plurality of peak impact force values. The method may include performing a drop test on a second plurality of solid dosage forms, and mea-
(Continued)

suring a plurality of physical defect rates. The method may include determining a model that describes a relationship between peak impact force values and physical defect rates, and determining, based on the model, a predicted physical defect rate.

8 Claims, 38 Drawing Sheets

(52) U.S. Cl.
CPC ............... *G01N 2203/0033* (2013.01); *G01N 2203/0087* (2013.01); *G01N 2203/0218* (2013.01); *G01N 2203/0234* (2013.01); *G01N 2203/0676* (2013.01)

(58) Field of Classification Search
CPC ... G01N 2203/0087; G01N 2203/0218; G01N 2203/0234; G01N 2203/0676
USPC ........................................ 73/788, 794, 12.06
See application file for complete search history.

(56) References Cited

FOREIGN PATENT DOCUMENTS

| | | | |
|---|---|---|---|
| JP | 2001116671 | A | 4/2001 |
| JP | 2010237197 | A | 10/2010 |

OTHER PUBLICATIONS

International Search Report and Written Opinion issued in PCT/US2022/024010, dated Nov. 4, 2022.

Kirk E. Wilson and Andrea Potter, "Advantages of Impact Testing over Hardness Testing in Determining Physical Integrity of Tablets", Journal Drug Development and Industrial Pharmacy, vol. 24, Nov. 1, 1998 (Nov. 1, 1998), pp. 1017-1024.

Hare C. et al., "Impact breakage of pharmaceutical tablets", International Journal of Pharmaceutics, vol. 536, No. 1, Dec. 22, 2017 (Dec. 22, 2017), pp. 370-376.

* cited by examiner

FIG. 1A

Figure 1B:
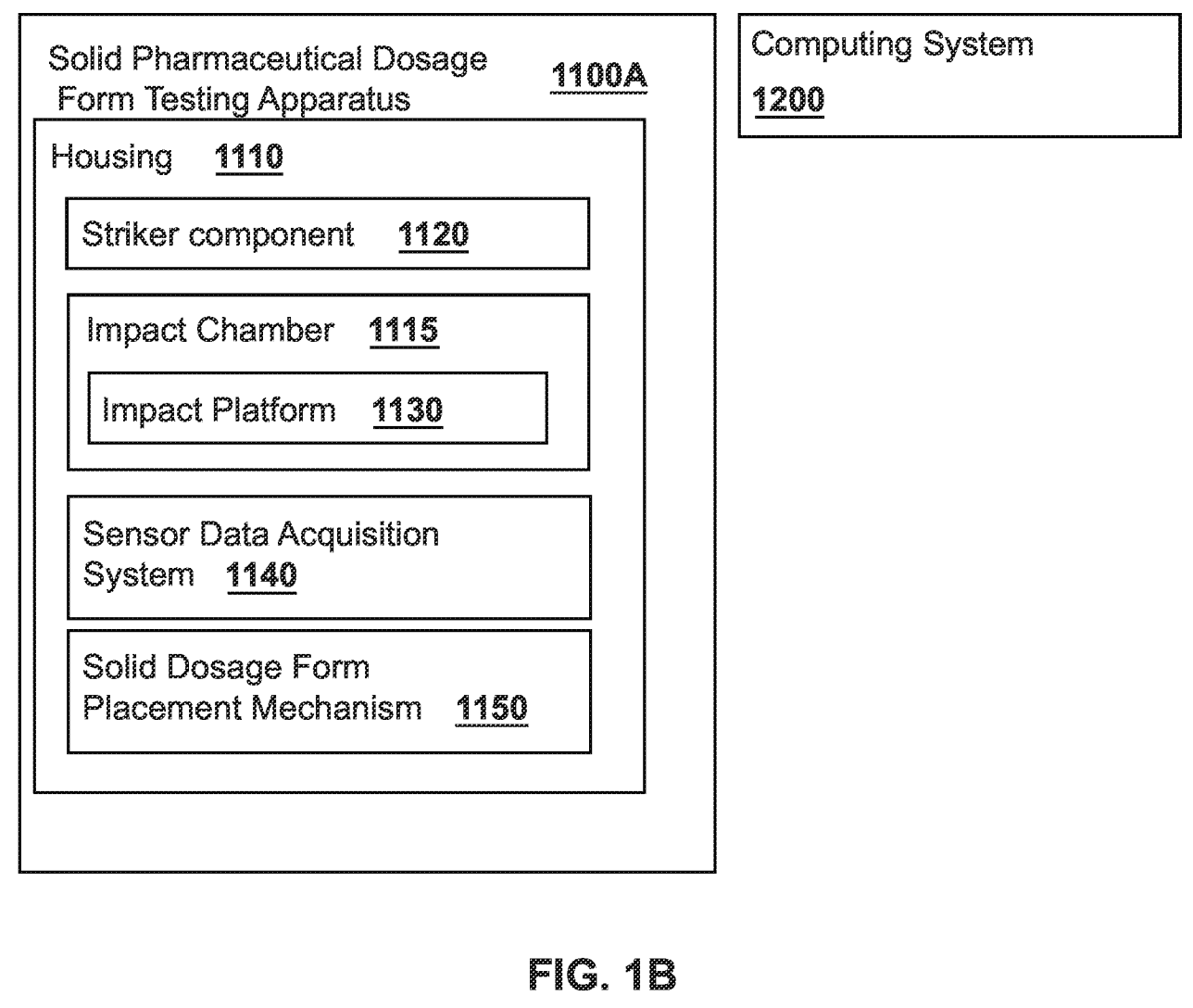

Computing System
1200

Solid Pharmaceutical Dosage
Form Testing Apparatus          1100A

Housing    1110

Striker component    1120

Impact Chamber    1115

Impact Platform    1130

Sensor Data Acquisition
System    1140

Solid Dosage Form
Placement Mechanism    1150

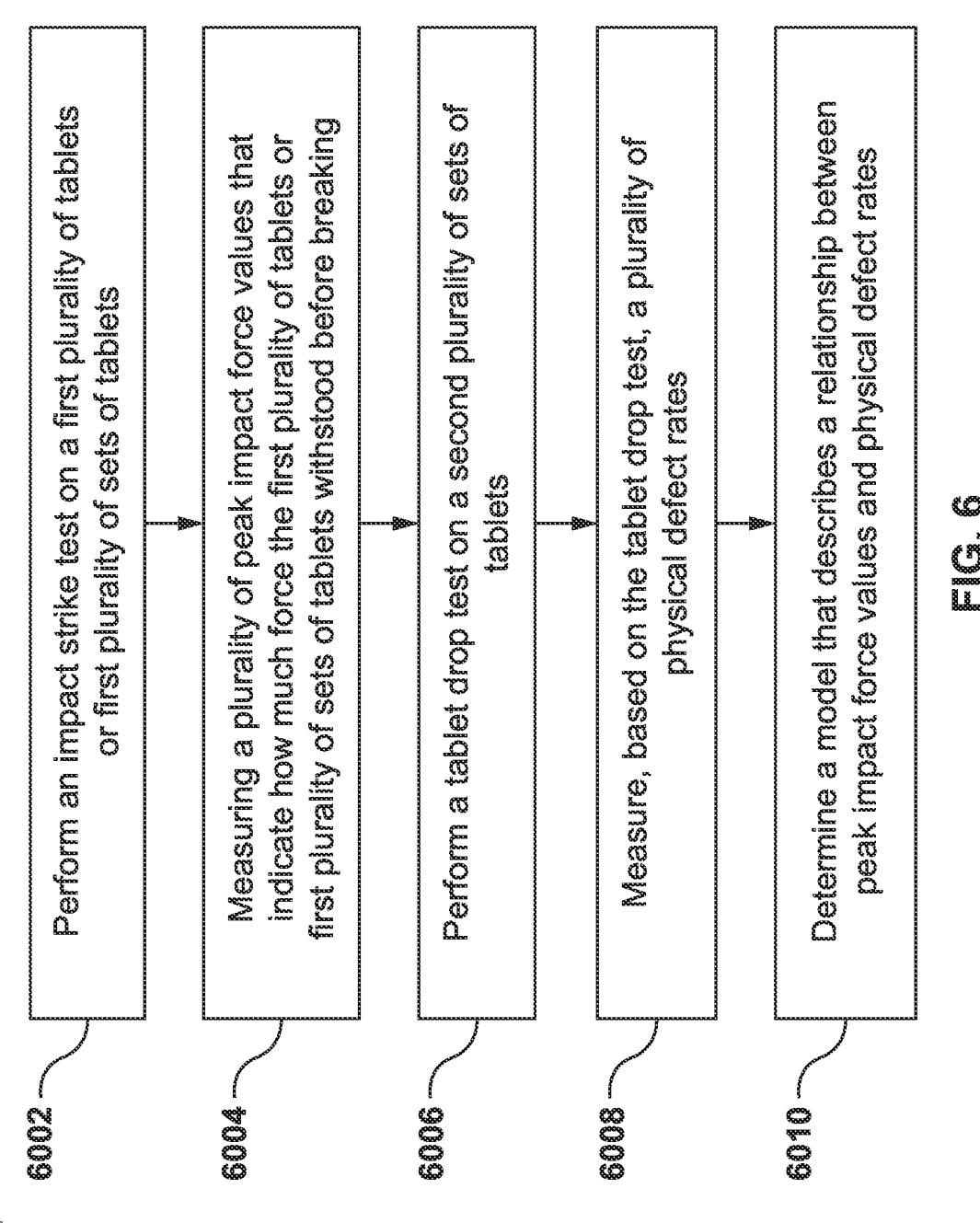

6002 — Perform an impact strike test on a first plurality of tablets or first plurality of sets of tablets 6004 — Measuring a plurality of peak impact force values that indicate how much force the first plurality of tablets or first plurality of sets of tablets withstood before breaking 6006 — Perform a tablet drop test on a second plurality of sets of tablets 6008 — Measure, based on the tablet drop test, a plurality of physical defect rates 6010 — Determine a model that describes a relationship between peak impact force values and physical defect rates Formulation: MCC:DCPA 50:50 2MPa

| Tablet Shape | NC 10mm | | Oval | |
|---|---|---|---|---|
| | Force [N] | Energy [J] | Force [N] | Energy [J] |
| Average (N=10) | 315 | 0.05582 | 259 | 0.02693 |
| Coefficient of variation % | 1.78 | 39.19 | 4.59 | 51.39 |

FIG. 8C

Formulation: MAN:MCC 50:50 3MPa

| Tablet Shape | NC 10mm | | Oval | |
|---|---|---|---|---|
| | Force [N] | Energy [J] | Force [N] | Energy [J] |
| Average (N=10) | 396 | 0.03588 | 338 | 0.02170 |
| Coefficient of variation % | 4.57 | 4.86 | 1.39 | 5.76 |

FIG. 8D

| Specimen ID | Average force at Peak [N] | Predicted defects after 5 drops at 2 meters height % |
|---|---|---|
| Tablet Type 11 (Formulation 1, 200mg) | 408 | ~1.8 |
| Tablet Type 12 (Formulation 2, 150mg) | 234 | ~3.5 |
| Tablet Type 13 (Formulation 2, 100mg) | 128 | ~17 |

FIG. 11A

| | % defects from 1 meter 1 drop | % defects from 1 meter 5 drops | % defects from 1 meter 10 drops | % defects from 2 meter 1 drop | % defects from 2 meter 5 drops | % defects from 2 meter 10 drops |
|---|---|---|---|---|---|---|
| Impact force P- value | 0.0001 | <0.0001 | 0.0002 | 0.0003 | <0.0001 | <0.0001 |
| Impact force R2 | 0.86 | 0.91 | 0.83 | 0.83 | 0.96 | 0.93 |
| Tensile Strength P- value | 0.151 | 0.080 | 0.043 | 0.289 | 0.103 | 0.024 |
| Tensile Strength R2 | 0.24 | 0.33 | 0.42 | 0.14 | 0.30 | 0.49 |

13002 — Receive peak impact force value measured by a tablet testing apparatus

13004 — Determine, based on the peak impact force value, at least one predicted physical defect rate

APPARATUS AND METHOD FOR EVALUATING PHYSICAL STRENGTH OR ROBUSTNESS OF SOLID PHARMACEUTICAL DOSAGE FORMS BASED ON AN IMPACT STRIKE TEST

FIELD OF THE INVENTION

The present invention is directed to an apparatus and method for evaluating physical strength or robustness of solid pharmaceutical dosage forms, such as tablets, mini tablets, pills, chewable gums, wafers, disks, caplets, lozenges, pastilles, implants, granules, and pellets, based on an impact strike test.

BACKGROUND

Solid pharmaceutical dosage forms, for example, tablets, mini tablets, pills, chewable gums, wafers, disks, caplets, lozenges, pastilles, implants, granules, and pellets, provide a mode in which medicine or other compounds may be delivered into a body of a user. A variety of pharmaceutical or drug formulations may be manufactured or formed into the tablets, mini tablets, pills, chewable gums, wafers, disks, caplets, lozenges, pastilles, implants, granules, and pellets. In some cases, different formulations may yield tablets, mini tablets, pills, chewable gums, wafers, disks, caplets, lozenges, pastilles, implants, granules, and pellets with different mechanical or other physical properties.

SUMMARY

In view of the foregoing, provided herein are a solid pharmaceutical dosage form testing apparatus and a method for evaluating toughness of solid pharmaceutical dosage forms, for example, tablets, mini tablets, pills, chewable gums, wafers, disks, caplets, lozenges, pastilles, implants, granules and pellets. In one aspect, a solid pharmaceutical dosage form testing apparatus includes a striker component, an impact platform, a sensor data acquisition system, and a placement mechanism for holding and properly positioning a solid pharmaceutical dosage form under the striker component. The placement mechanism has a first push component and a second push component that are movable toward each other to position a solid pharmaceutical dosage form at an impact site. The method includes performing an impact strike test on a first plurality of solid pharmaceutical dosage forms or a first plurality of sets of solid pharmaceutical dosage forms, and measuring a plurality of peak impact force values. The method further may include performing a drop test on a second plurality of sets of solid pharmaceutical dosage forms, and measuring a plurality of physical defect rates. The method may further include determining a model that describes a relationship between peak impact force values and physical defect rates, and determining, based on the model, a predicted physical defect rate.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The drawings are not necessarily to scale.

FIGS. 1A and 1B depict block diagrams of a solid pharmaceutical dosage form testing apparatus according to embodiments herein.

FIG. 2BB depicts front and side views of a tablet testing apparatus sized for benchtop use according to embodiments herein.

FIG. 6 is a flow diagram which depicts a method for evaluating the strength of a tablet or a sample of a batch of tablets according to an embodiment herein.

FIGS. 8C and 8D depict various values of peak impact force and energy imparted to a tablet during an impact strike test according to embodiments herein.

FIGS. 11A and 11B illustrates predicted physical defect rates based on various peak impact force values according to an embodiment herein.

FIG. 12A illustrates a comparison between p-values and $R^2$ values associated with peak impact force and with p-values and $R^2$ values associated with tensile strength according to an embodiment herein.

DETAILED DESCRIPTION

Figure 2A:
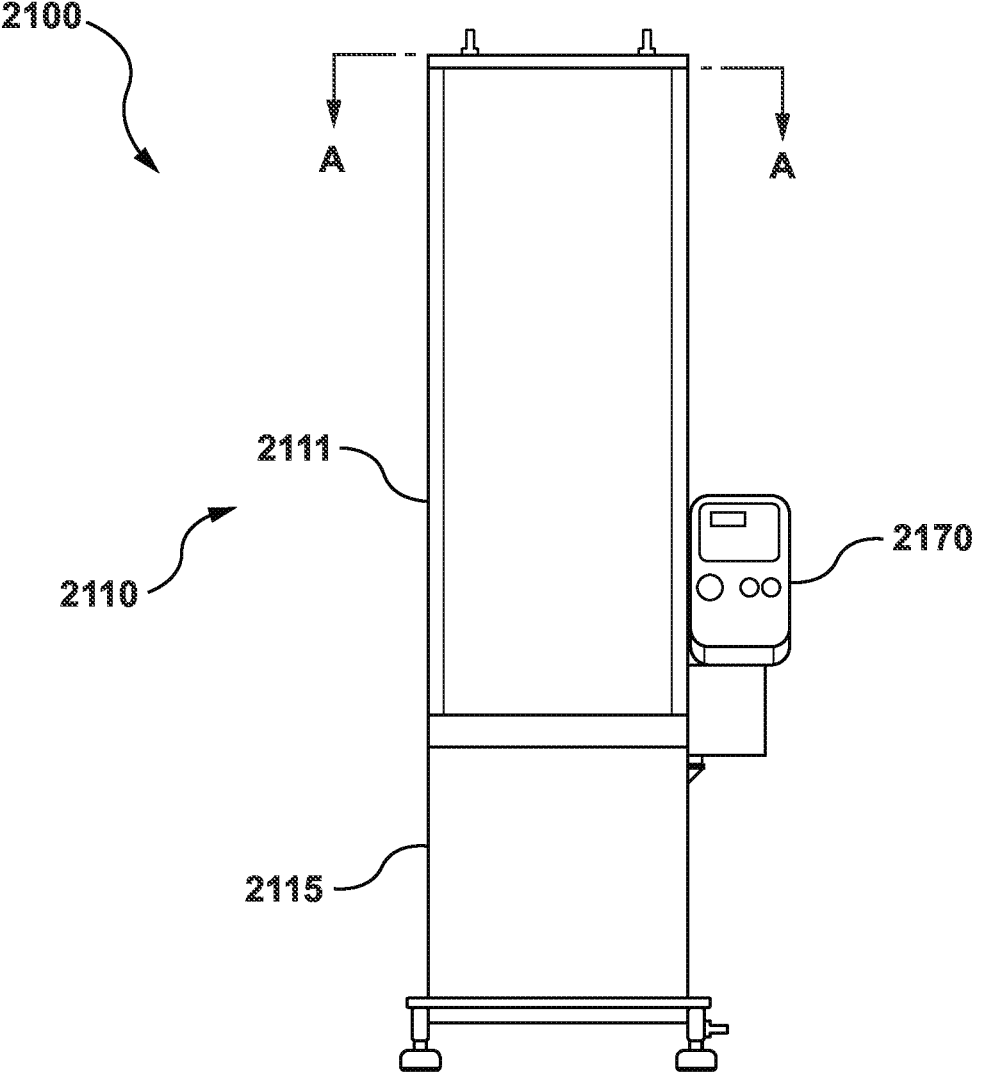
FIGS. 2A and 2B depict views of a tablet testing apparatus according to embodiments herein.

It should be appreciated that the particular implementations shown and described herein are examples of solid pharmaceutical dosage forms and testing thereof and are not intended to otherwise limit the scope of the application in any way. As used in this specification, the singular forms "a," "an" and "the" specifically also encompass the plural forms of the terms to which they refer, unless the content clearly dictates otherwise.

The following detailed description is merely exemplary in nature and is not intended to limit the invention or the application and uses of the invention. Although the description of embodiments hereof is in the context of evaluating or assessing physical strength or robustness of solid pharmaceutical dosage forms, such as tablets or sample of a batch of tablets, the invention may also be used in in the context of evaluating or assessing physical strength or robustness of solid pharmaceutical dosage forms, such as mini tablets, pills, chewable gums, wafers, disks, caplets, lozenges, pastilles, implants, granules, and pellets, and samples of batches thereof, where it is deemed useful. Furthermore, there is no intention to be bound by any expressed or implied theory presented in the preceding technical field, background, brief summary or the following detailed description.

One aspect of the present application relates to evaluating or assessing physical strength or robustness of solid pharmaceutical dosage forms that are a sample or subset of a batch of tablets, wherein "tablet" as used herein may refer to a tablet core, a coated tablet and an uncoated tablet, to assess their ability to withstand forces or conditions in various environments to which the tablets may be exposed, such as a manufacturing facility, for instance, during a coating process of a tablet core, a packaging process and/or an inspection process, a warehouse facility, a pharmacy, a hospital, a patient's home, or an environment during shipping of the tablets from the manufacturing facility to the pharmacy, hospital, home, or some other location. For instance, the tablets may be accidentally dropped onto solid surfaces in these environments or subjected to forces during processing, for instance forces received by a tablet core during a coating process, and evaluating the physical strength or robustness of these tablets may involve predicting or otherwise determining a physical defect rate associated with the tablets if they are dropped, e.g., from a particular height and/or are dropped a particular number of times. Such an evaluation or assessment may be used to determine whether a tablet's formulation, such as a pharmaceutical formulation or drug formulation, yields sufficiently robust mechanical or other physical properties to allow the tablets to withstand conditions or events to which the tablets may be exposed. In some instances, assessing the physical strength of a sample or subset of a batch of tablets may involve determining their tensile strength via, e.g., a hardness test, and using the tensile strength as an indication of the tablets' strength (the tensile strength may be calculated from, e.g., pharmacopeia hardness test data and tablet dimensions generated from the Sotax HT100 and compression tool dimensions using Pitt's equation, which is discussed in K. T. Pitt & M. G. Heasley's "*Powder Technology*", pp. 169-175). However, a parameter such as tensile strength does not account for a rapid transfer of energy, such as free-falling tablets hitting a solid surface. Such events may impart a shock or other force to a falling tablet, and may fracture or otherwise break the tablet. In some cases, a tablet or tablet's formulation may have a high tensile strength, as determined via a hardness test, but may still have poor ability to handle shocks, impacts, or other events involving a rapid transfer of energy. Thus, the hardness test and the tensile strength parameter may have poor predictability of physical defect rates for tablets in a large scale manufacturing setting, and my lead to deviations between the predicted versus actual physical robustness of manufactured tablets.

In an embodiment, a peak impact force parameter may be used to assess the physical strength of tablets. More particularly, values of the peak impact force parameter, also referred to as peak impact force values, may be used to predict a physical defect rate for a batch of tablets. The peak impact force values may be measured by, e.g., performing an impact strike test in which a striker component strikes and breaks one or more of a sample of a batch of tablets. During the test, a peak amount of force imparted to a tablet, or an average of peak amounts of force imparted to a set of tablets, may be measured. Because these measurements are better indicators of the rapid transfer of energy, they may provide a better ability to assess the physical strength of tablets, or more specifically to predict physical defect rates for tablets.

In an embodiment, the peak impact force parameter may be used as an indirect measurement or approximation of impact toughness, also referred to as toughness, of a tablet (e.g., a core tablet, a coated tablet, an uncoated table, etc.) or a batch of tablets (e.g., tablet cores, coated tablets, uncoated tables, etc.). In some cases, the toughness of a sample or subset of a batch of tablets may be directly measured, such as by determining an area under a stress-strain curve of the tablets. In such cases, the directly measured toughness of the tablet or sample of the batch of tablets may be used to predict a physical defect rate for the batch of tablets. In an embodiment, a computing system or other device may receive sensor data which is indicative of force received by a tablet during an impact strike test. In some implementations, the computing system may be configured to determine, based on the sensor data, whether the tablet was broken, or suffered some other physical defect, during the impact strike test.

In an embodiment, the impact strike test may be performed with a solid pharmaceutical dosage form or tablet testing apparatus which uses a striker component that is releasably suspended above an impact site. In some implementations, the tablet testing apparatus may include a solid pharmaceutical dosage form or tablet placement mechanism (also referred to as a tablet centering mechanism or a tablet holder) for placing a solid pharmaceutical dosage form or tablet so that the solid pharmaceutical dosage form or tablet is centered around an impact site, and is located directly under the striker component. When implemented as a tablet placement mechanism, the mechanism may thus place a tablet at a location at which a center of the tablet is aligned with a center of a tip of the striker component, such that the center of the tablet will be struck by the falling striker component. In some implementations, the tablet placement mechanism may have recessed portions for accommodating a curvature of tablet. The recessed portion, when engaged with the tablet, may push the tablet toward an impact site. In some implementations, the tablet testing apparatus may include a channel for directing air flow toward an impact chamber that surrounds the impact site. The air flow may reduce a likelihood of debris or other material, which may be generated during the impact strike test, from escaping a housing of the tablet testing apparatus. In an embodiment, the tablet testing apparatus may include a waste collection apparatus or component that is configured to perform waste collection or waste removal after every impact strike test, or after every few impact strike tests. The waste collection or waste removal may involve, e.g., automatically remove a tablet from an impact site, wherein the removed tablet may have been broken or otherwise subjected to an impact strike test. In some instances, the tablet placement mechanism may be configured, after the tablet has been removed, to automatically retrieve a new tablet and place the new tablet at the impact site, so that an impact strike test can be performed on the new tablet. In an embodiment, the tablet testing apparatus may be configured to automate a tablet testing process, by automatically loading a tablet onto an impact platform, causing the tablet placement mechanism to automatically place the tablet at an impact site on the impact platform, causing a striker component to be released onto and strike the tablet, collect sensor data or other measurements relating to the striking of the tablet, cause the waste collection apparatus to automatically remove the tablet from the impact platform, and repeat the process by loading a next tablet onto the impact platform. In this manner, the tablet testing apparatus may be able to automatically test a sample or subset of a batch of tablets in a carousel fashion.

Figure 1A:
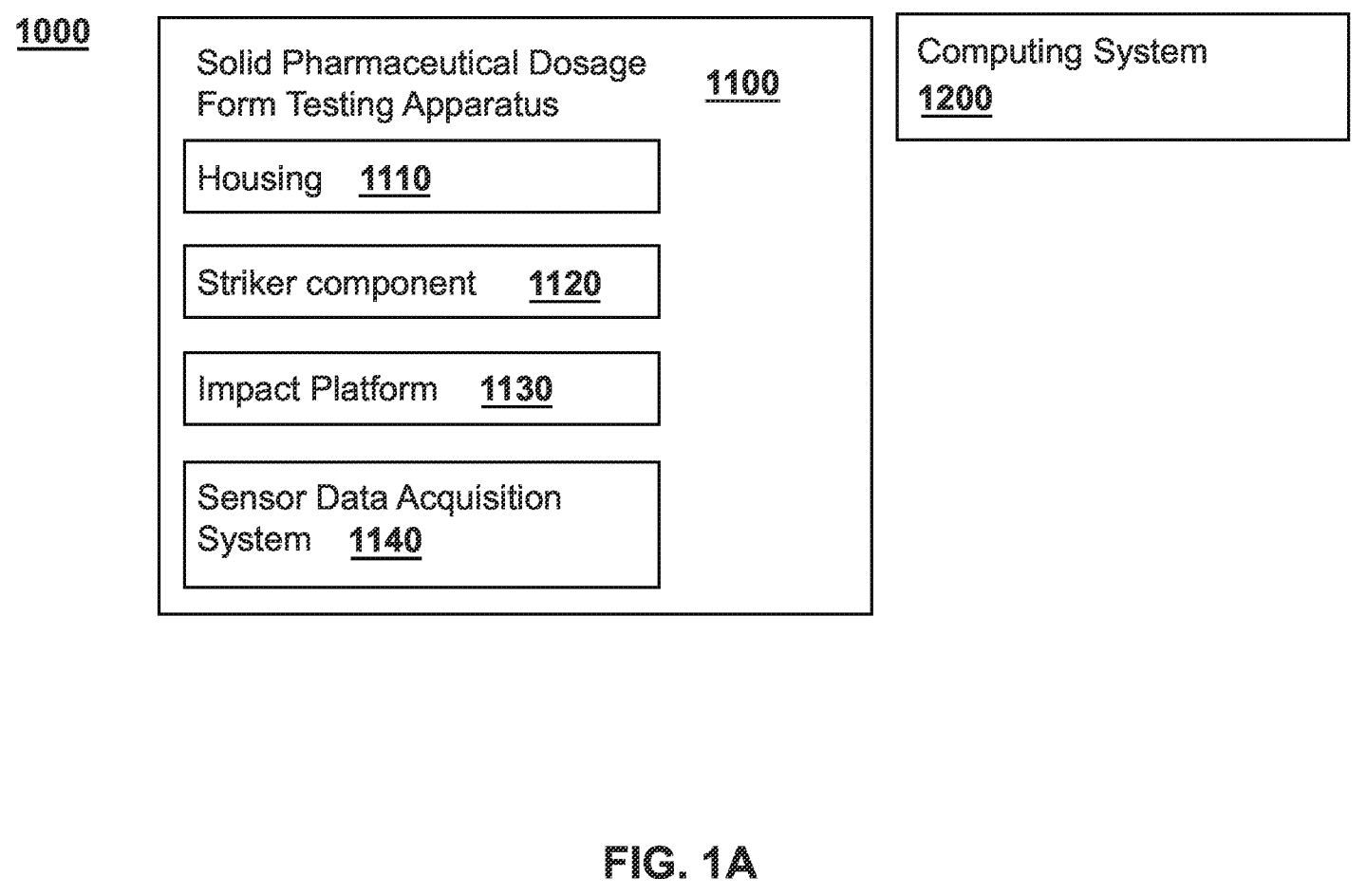

FIG. 1A provides a block diagram of a system 1000 for evaluating a mechanical property or properties for a solid pharmaceutical dosage form such as a tablet or a sample of a batch of tablets, and/or for assessing a mechanical or physical strength or robustness of the tablets. In some instances, the system 1000 may be part of a pharmaceutical or other manufacturing facility that manufactures drug tablets, dietary tablets, or other ingestible tablets, or any such formulations for pills, chewable gums, wafers, disks, caplets, lozenges, pastilles, implants, granules, and pellets. For instance, the system 1000 may be used to provide a quality control process within the manufacturing facility or research/development facility, by being used to predict whether a batch of tablets will be strong or otherwise robust enough to withstand handling by the manufacturer, by pharmacists, doctors, patients, or others. Such handling may involve events such as dropping of the tablets onto a hard surface or other events which may subject the tablets to a shock or force that can break or otherwise introduce physical defect into the tablets.

In the embodiment of FIG. 1A, the system 1000 may include a solid pharmaceutical dosage form testing apparatus 1100 and a computing system 1200. As discussed below in more detail, the solid pharmaceutical dosage form testing apparatus 1100 may be used to perform an impact strike test on a tablet, and more specifically to generate sensor data that measures an amount of force or energy involved in striking the tablet. In an embodiment, the solid pharmaceutical dosage form testing apparatus 1100 may include a housing 1110 in which various components of the solid pharmaceutical dosage form testing apparatus 1100, such as a striker component 1120 and an impact platform 1130, are disposed. The impact platform 1130 may be configured as a substrate or a surface on which a solid pharmaceutical dosage form can be disposed. More specifically, the impact platform 1130 may include an impact site at which the striker component 1120 will collide with the impact platform 1130 or with a solid pharmaceutical dosage form disposed directly over the impact site. For example, the striker component 1120 may be suspended over the impact platform 1130. In this example, the impact site may be a location on a top surface of the impact platform 1130 that is directly under the striker component 1120. The housing 1110 may include a striker mechanism configured to releasably suspend the striker component 1120 above the impact site on the impact platform 1130. The striker mechanism may be able to, as part of an impact strike test, release the striker component 1120 to allow the striker component 1120 to fall or drop toward the impact site under the influence of gravity. The falling striker component 1120 may hit or otherwise strike a solid pharmaceutical dosage form (if any) disposed at the impact site. In some cases, the striker component 1120 may strike the tablet with sufficient momentum or energy to cause the tablet to fracture or otherwise break into multiple pieces.

In an embodiment, the solid pharmaceutical dosage form testing apparatus 1100 may include a sensor data acquisition system 1140 for acquiring or otherwise generating sensor data associated with an impact strike test that is performed using the solid pharmaceutical dosage form testing apparatus 1100. As stated above, the sensor data may measure or otherwise indicate a parameter such as a speed or kinetic energy of the striker component 1120 as it is falling toward a solid pharmaceutical dosage form at the impact site, and/or an amount of force imparted to a solid pharmaceutical dosage form by the striker component 1120. In some instances, the sensor data acquisition system 1140 may include one or more sensors for generating the sensor data. For instance, the one or more sensors may include a first sensor configured to measure a speed or kinetic energy of the striker component 1120 as it is falling, and include a second sensor configured to measure an amount of energy imparted by the striker component 1120 to a solid pharmaceutical dosage form when the striker component 1120 strikes the solid pharmaceutical dosage form. In some implementations, the sensor data acquisition system 1140 may be configured to store the sensor data. For example, the sensor data acquisition system 1140 may include a circuit, e.g., an analog-to-digital converter (DAC) and/or a digital signal processing (DSP) circuit configured to receiving the sensor data from the one or more sensors, and/or may include a non-transitory computer-readable medium (e.g., a solid state drive or a hard disk drive) for storing the sensor data.

FIG. 1B illustrates a solid pharmaceutical dosage form testing apparatus 1100A in accordance with an embodiment hereof, which may be an embodiment of the solid pharmaceutical dosage form testing apparatus 1100, that includes a solid dosage form placement mechanism 1150 and an impact chamber 1115. In an embodiment, the solid dosage form placement mechanism 1150 may be configured to push or otherwise move a solid dosage form, such as a tablet, mini tablet, pill, chewable gum, wafer, disk, caplet, lozenge, pastille, implant, granule or pellet, toward an impact site on an impact platform 1130, so as to cause the solid dosage form to be located directly under a striker component 1120 before a start of an impact strike test. In some implementations, the impact chamber 1115 may be a chamber that is part of a housing 1110 and surrounds the impact platform 1130. The impact chamber 1115 may be used to trap or otherwise contain debris that may be generated when a solid dosage form is struck by a striker component 1120. More specifically, the impact chamber 1115 may prevent the debris from diffusing to an environment outside of the housing 1110, so as to protect technicians or other personnel who are monitoring an impact strike test from being exposed to pharmaceutical compounds or other material in the debris.

In an embodiment, a computing system 1200 of FIGS. 1A and 1B may be configured to process sensor data. In some implementations, the data processing may involve, e.g., determining a model which describes a relationship between: (i) how much impact force a solid dosage form is able to withstand before breaking and (ii) a likelihood of the solid dosage form experiencing a physical defect as a result of being dropped, or some other relationship. In some implementations, the data processing may involve generating a prediction regarding a physical defect rate among a solid dosage form or batch of solid dosage forms, wherein the physical defect rate may indicate a likelihood that one of the batch of solid dosage forms will experience a physical defect when dropped onto a hard surface or when experiencing some other type of physical shock.

In an embodiment, a computing system 1200 may include, e.g., at least one processing circuit (e.g., a computer processor) and a non-transitory computer-readable medium (e.g., a solid state drive). The processing circuit may be configured to perform the processing of the sensor data. In some instances, the processing circuit may process the sensor data by executing instructions stored on or in the non-transitory computer-readable medium. The computing system 1200 may be a standalone device (e.g., a desktop computer or a server) separate from a solid pharmaceutical dosage form testing apparatus 1100, or may be a part of a solid pharmaceutical dosage form testing apparatus 1100 (e.g., a computing circuit or chip embedded within the solid pharmaceutical dosage form testing apparatus 1100).

Figure 2B:
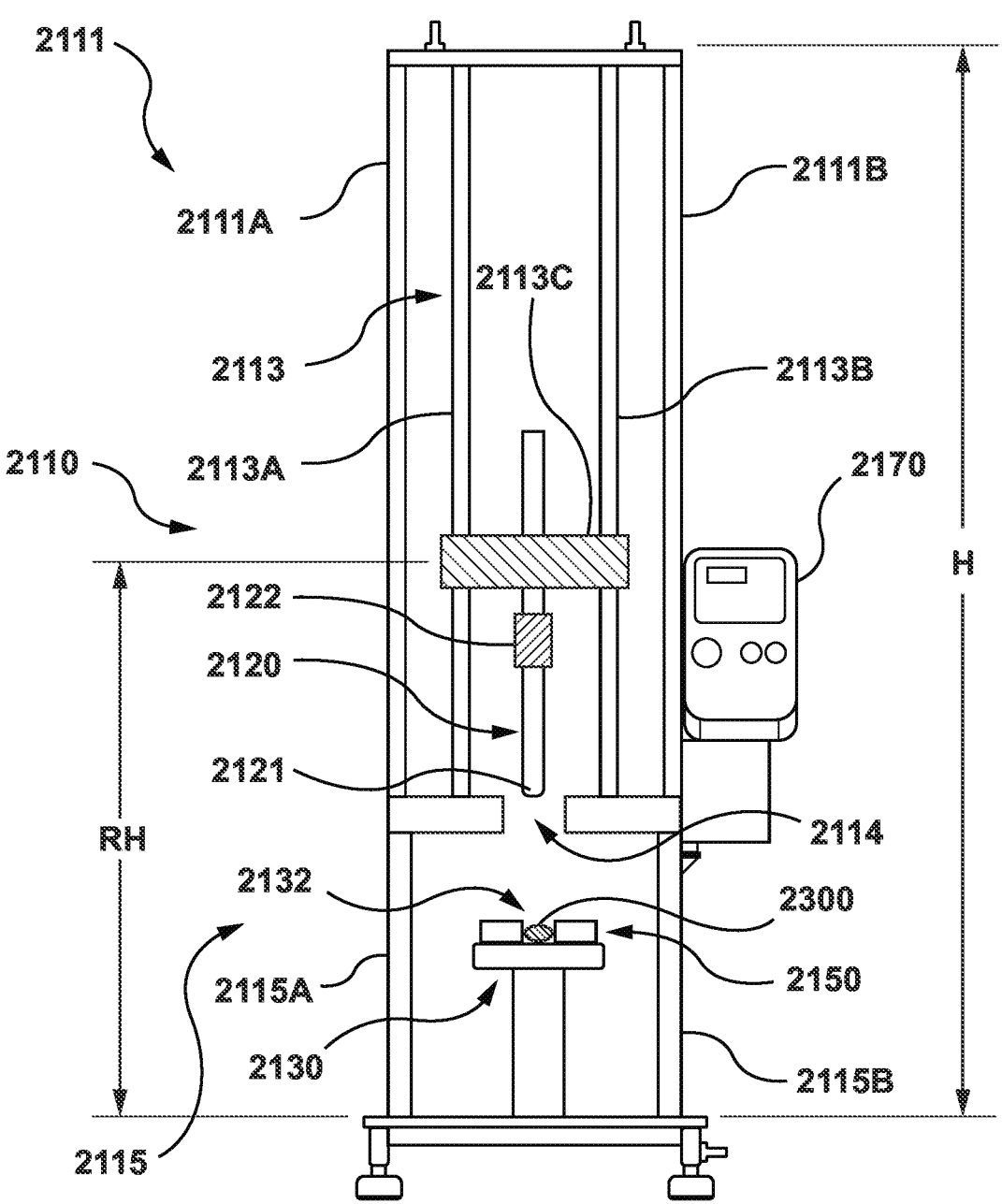
Figure 2B:
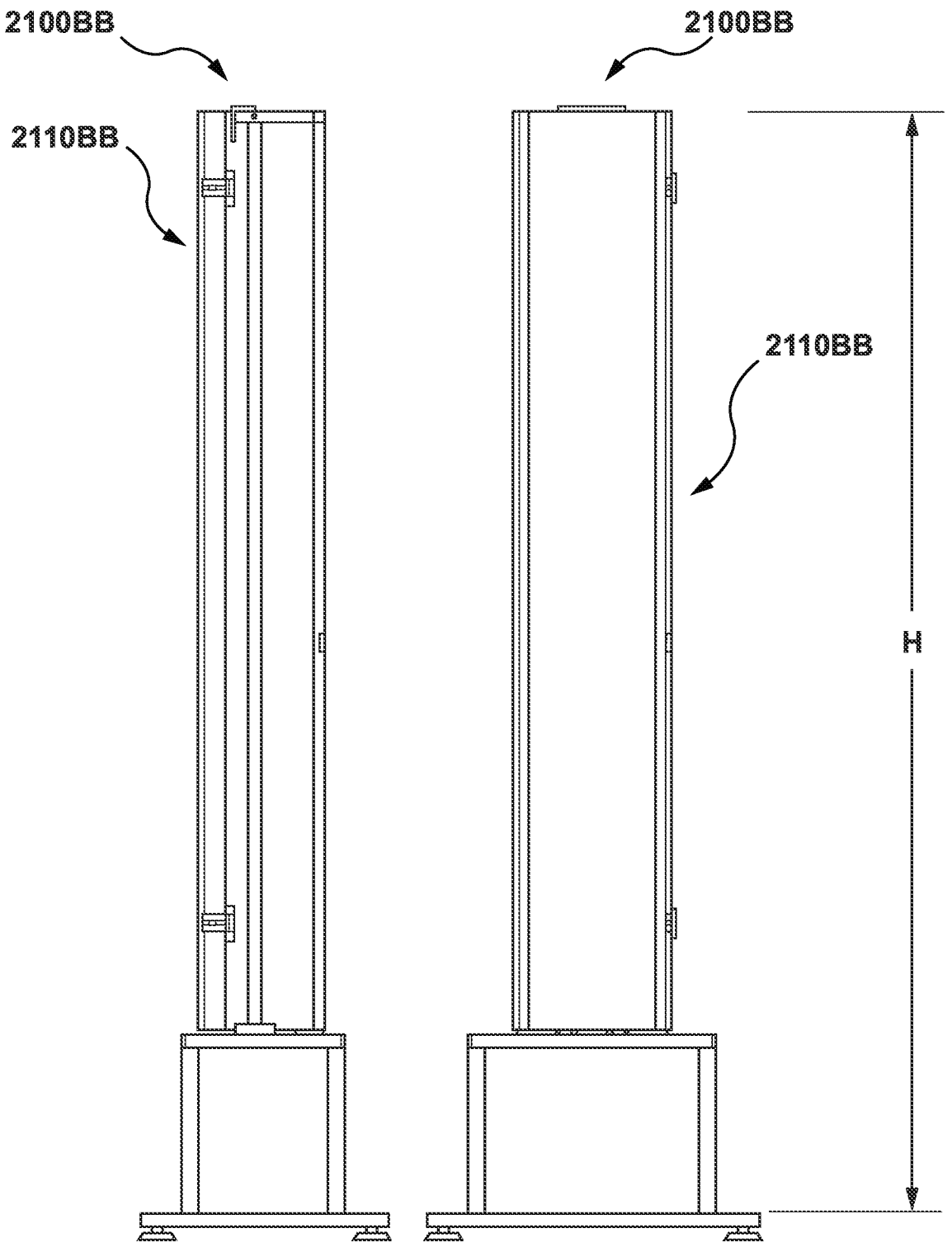

FIGS. 2A and 2B illustrate a tablet testing apparatus 2100 in accordance with an embodiment hereof, which may be an embodiment of the solid pharmaceutical dosage form testing apparatus testing apparatus 1100, 1100A. The tablet testing apparatus 2100 is configured as a floor standing system, which is by way of example and not limitation, and as noted below a benchtop or tabletop system also falls within the scope of the present disclosure. More particularly, FIG. 2A is a front view of the tablet testing apparatus 2100, while FIG. 2B is a sectional view of the tablet testing apparatus 2100 taken along line A-A in FIG. 2A. As depicted in FIG. 2A, the tablet testing apparatus 2100 includes a housing 2110 in which various components of the tablet testing apparatus 2100 are disposed. In an embodiment, a housing 2110 may form one or more chambers, such as a striker component chamber 2111 and an impact chamber 2115, which are discussed below in more detail. As depicted in FIG. 2B, the striker component chamber 2111 may be enclosed by one or more walls, such as walls 2111A and 2111B, while the impact chamber 2115 may also be enclosed by one or more walls, such as walls 2115A and 2115B. FIG. 2A further depicts the tablet testing apparatus 2100 having a user input device 2170, which may be configured to receive a user command or other user input. For instance, the user input device 2170 may be configured to receive one or more user commands associated with performing an impact strike test.

In an embodiment, a striker component chamber 2111 may be a chamber that contains an impact striker 2120) (also referred to as a tup), as illustrated in FIG. 2B. The striker component chamber 2111 may further contain a striker mechanism 2113 that releasably suspends the striker component 2120 above the impact chamber 2115. The striker mechanism 2113 may be configured to release the striker component 2120, so as to cause the striker component 2120 to fall or drop through an opening 2114 and onto an impact site 2132 within the impact chamber 2115, where the striker component 2120 may hit or otherwise strike a tablet 2300 or other object disposed at the impact site 2132. Thus, the impact chamber 2115 may contain the impact site 2132, and may be used to trap or otherwise contain debris that may be generated by the strike. In some implementations, the solid pharmaceutical dosage or tablet testing apparatus 1100, 1100A, 2100 may include a motor or other actuator which is configured to raise a striker component after it has been dropped, so that the striker component can be released once more to perform another impact strike test.

In an embodiment, an impact site 2132 may be provided by an impact platform 2130, which may be an embodiment of the impact platform 1130, that may be contained in an impact chamber 2115, and may provide a substrate for receiving an impact or other collision with a striker component 2120. For instance, the impact platform 2132 may be an object or apparatus which provides an upper surface that is flat (to form a flat upper surface) or that curves outward or inward (to form a convex upper surface or concave upper surface). In such instances, the impact site 2132 may be a location, such as a center location, on the flat upper surface of the impact platform 2130. The impact platform 2130 may have a cylindrical shape, a rectangular shape, or any other shape. In an embodiment, a tablet testing apparatus 2100 may include a tablet placement mechanism 2150, which may be an embodiment of the tablet placement mechanism 1150, that is disposed on the upper surface of an impact platform 2130. The tablet placement mechanism 2150 may have components that surround and/or are equidistant from the impact site 2132, and may be configured to push or otherwise move a tablet toward the impact site 2132, and more specifically to cause the tablet to be centrally placed around the impact site 2132, such that a center of the tablet may be directly above the impact site 2132. In some implementations, once the tablet 2300 placement mechanism has moved the tablet to the impact site, its components may move away from the tablet 2300, so as to disengage from the tablet. As a result, the tablet placement mechanism 2150 is no longer in contact with the tablet 2300. By moving out of contact with the tablet 2300, the tablet placement mechanism 2150 may avoid interfering with the impact strike test and avoid influencing sensor data generated during the impact strike test. Tablet placement mechanisms are discussed below in more detail.

In an embodiment, a striker component 2120) (also referred to as a tup) may be a rigid component, such an elongated rod made of a metal, such as stainless steel. The striker component 2120 is configured to be released or dropped to make impact with an impact site 2132 of an impact platform 2130. In some implementations, the striker component 2120 may have a tip 2121, such as a flat tip or a rounded tip, or more specifically a tip facing the impact site 2132, that is configured to contact a center of a tablet 2300 disposed at the impact site 2132 when the striker component 2120 impacts or otherwise strikes the tablet 2300. In embodiments hereof, a tip 2121 may be made of a metal, such as stainless steel.

In an embodiment, the striker component 2120 may have a body that is shaped as an elongated cylinder with the tip 2121 having a rounded profile. FIG. 2D depicts a flat tup insert 2121A that may be attached to a striker component 2120D to serve as a tip thereof with a flat face, and a hemispherical tup insert 2121B that may be attached to the striker component 2120D to serve as a tip thereof with a rounded face. Accordingly in some cases, a striker tip may be formed by an insert or a tup insert made of a metal, such as stainless steel, which may be inserted into or otherwise attached to a shaft forming the elongated cylinder, or other structure, of a striker component, such as shown in FIG. 2D for the striker component 2120D. Simply restating the foregoing, for example, a flat tip 2121 may be formed from a flat tup insert 2121A, while a rounded tip 2121 may be formed from a hemispherical tup insert 2121B or other curved tup insert. In some instances, a diameter of the cylinder may be similar to diameters or some other dimension (e.g., lengths or widths) of various tablets. As an example, the diameter of the cylinder may be in a range from, e.g., 5 mm to 12 mm.

In embodiments hereof, a striker component, a tip and/or a tip or tup insert may be formed of a non-rigid material chosen to mimic a material that a tablet may come into contact with at its various stages of manufacture, packaging, storing and transport. In such an embodiment, a striker component, a tip and/or a tip or tup insert may be formed from a non-rigid or soft elastomeric or polymeric material. In another embodiment, a striker component, a tip and/or a tip or tup insert may be formed from a non-rigid cardboard or other such packaging material.

Figure 2C:
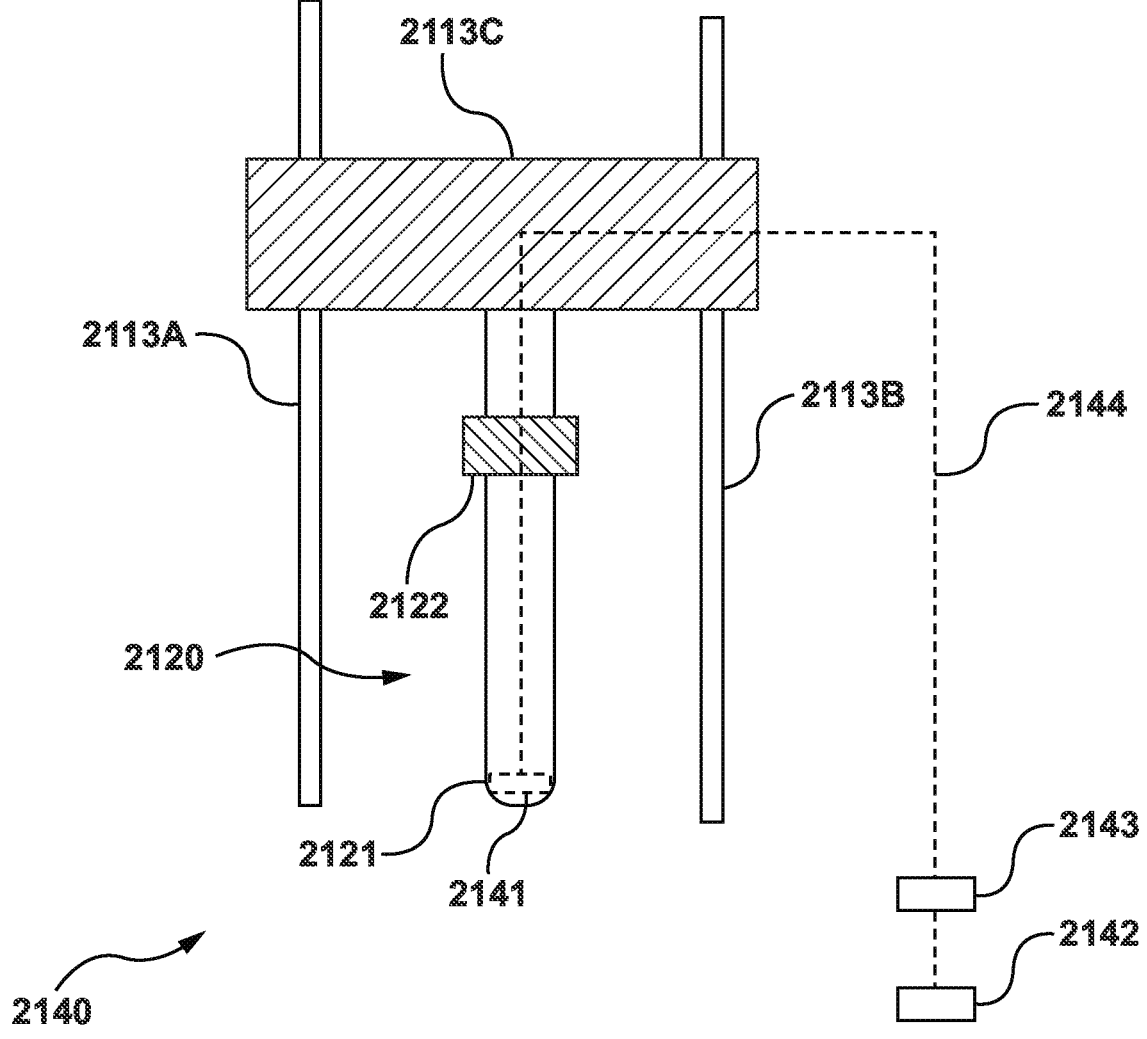
FIG. 2C depicts a sensor data acquisition system according to an embodiment herein.
Figure 2D:
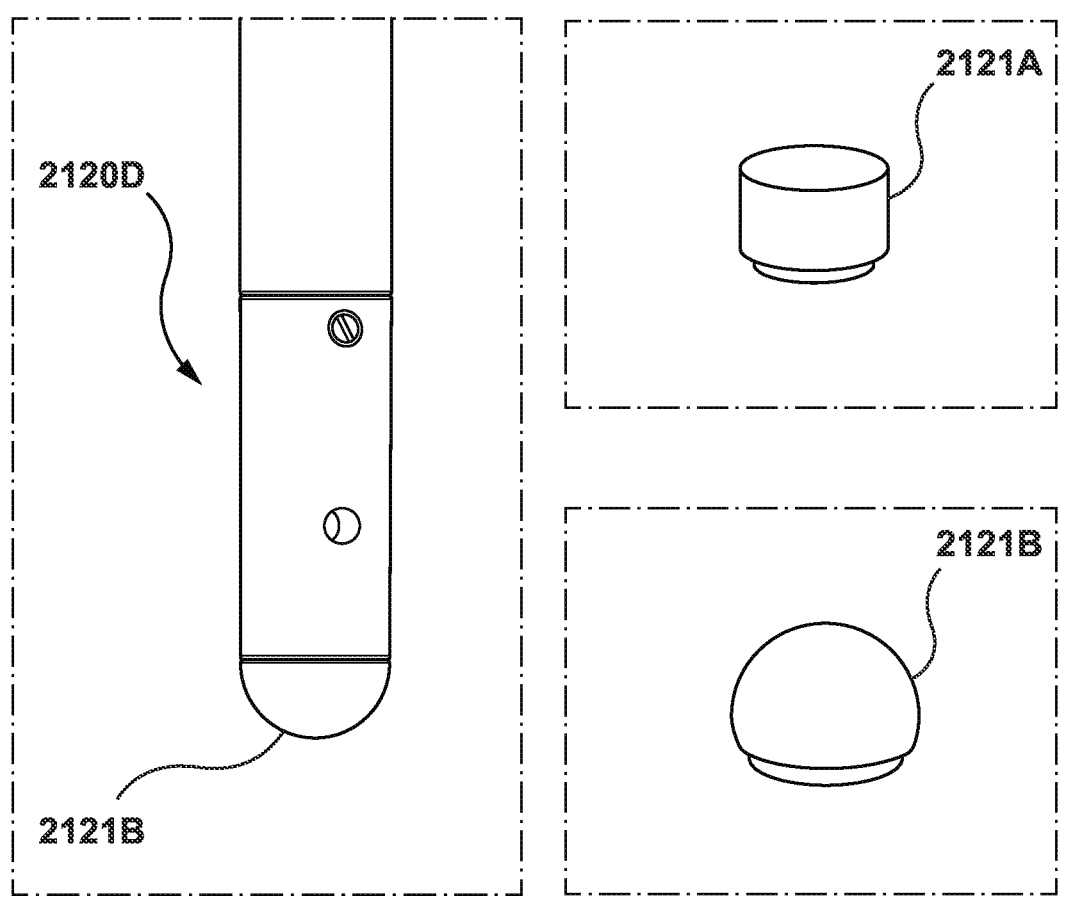
FIG. 2D depicts various tup inserts for a striker component according to embodiments herein.

In an embodiment and with reference to FIGS. 2B and 2C, a striker component 2120 may include one or more objects 2122 which may be removably attached to the body of the striker component 2120, so as to provide additional mass or weight to the striker component 2120. For instance, the one or more object 2122 may include one or more disks that may be slipped around a portion of the body of the striker component 2120. In some implementations, for a certain drop distance, a total mass of the striker component 2120, including the one or more objects 2122, may be sufficiently small so as to place a force of impact between the striker component 2120 and a drug tablet or other tablet within a range which is sufficient to break the tablet but is not large enough to completely crush the tablet. In some cases, for a certain drop distance, the total mass of the striker component 2120 may be less than or equal to 1 kg, or less than or equal to 0.5 kg.

Figure 2E:
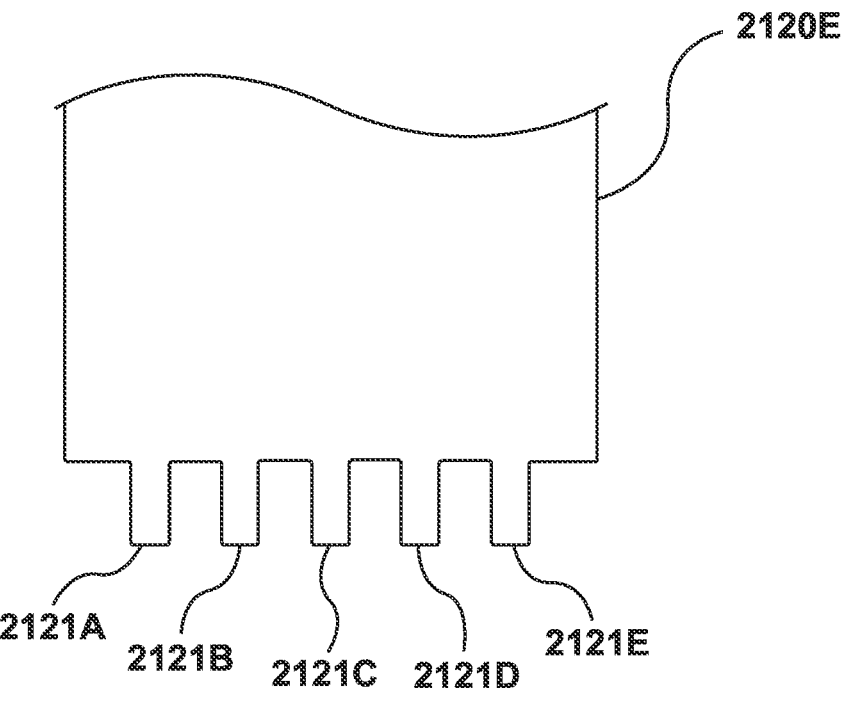
FIG. 2E depicts a striker component having multiple tips for striking multiple tablets simultaneously according to an embodiment herein.

In an embodiment, a striker component 2120E shown in FIG. 2E may have multiple tips or tup inserts configured to impact multiple tablets simultaneously. The multiple tips or tup inserts may thus be used to implement parallel processing of multiple tablets, so as to increase a speed by which impact strike tests can be performed on a sample or subset of a batch of tablets or other solid pharmaceutical dosage forms. In FIG. 2E the striker component 2120E includes tips or tup inserts 2121A, 2121B, 2121C, 2121D, 2121E. In some cases, the multiple tips may form a 2D array of tips (also referred to as a matrix of multiple tips). In this embodiment, a weight of the striker component, or more specifically a tup weight or tup mass, may be increased relative to the striker component of FIG. 2C. The weight or mass of the striker component 2120E may be increased to a level so that when the striker component 2120E in FIG. 2E falls from a certain height and collides with multiple tablets, it is able to impart sufficient force to have a reasonable likelihood of breaking all of the tablets. Further in this embodiment, a respective sensor may be disposed within or attached to each of the tips or tup inserts 2121A, 2121B, 2121C, 2121D, 2121E, so as to collect sensor data indicative of an amount of force imparted by the respective tip to a respective tablet struck by the tip.

Figure 2F:
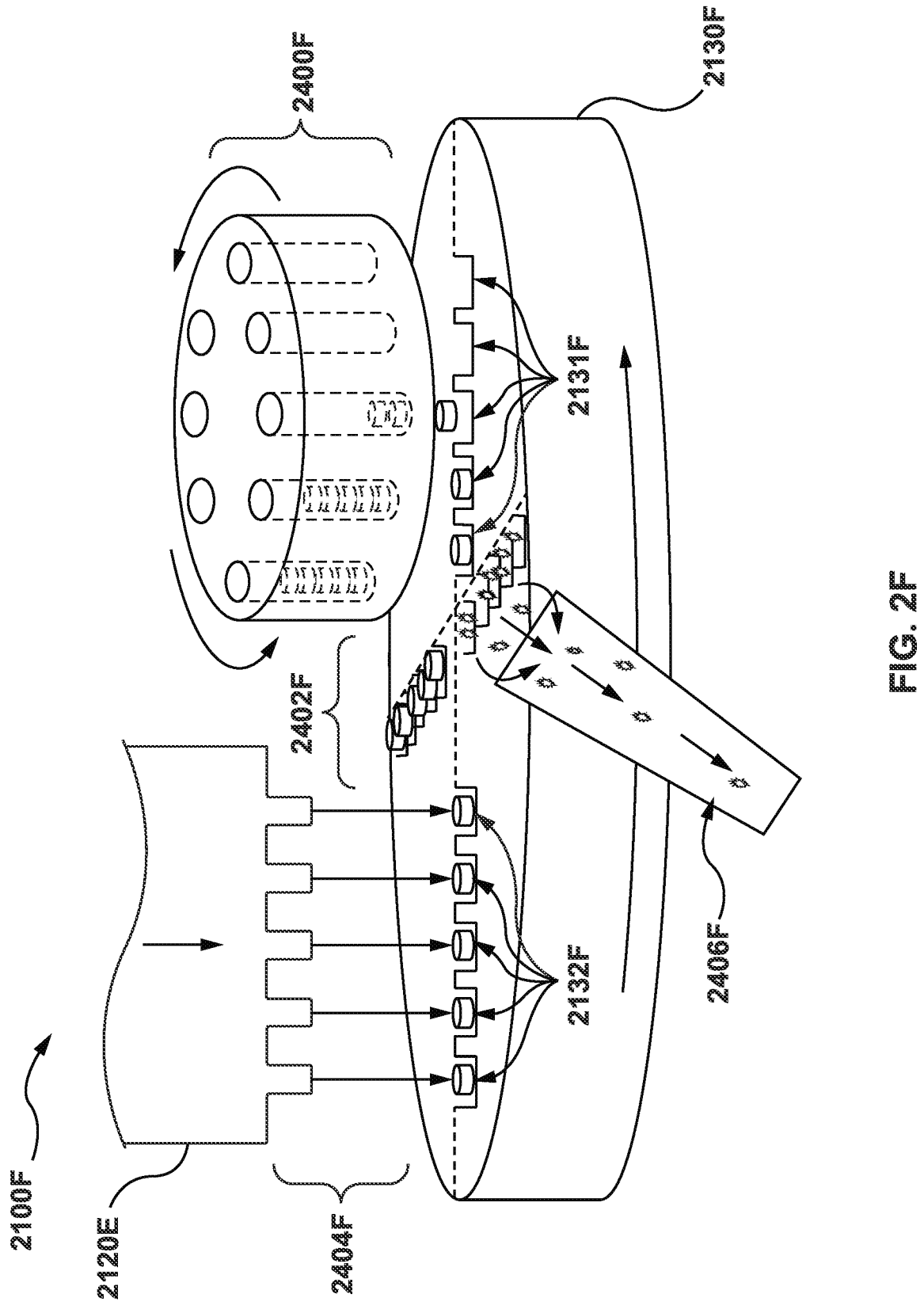
FIG. 2F depicts a carousel for dispensing tablets, and depicts a vacuum-based clearing system, according to an embodiment herein.
Figure 2G:
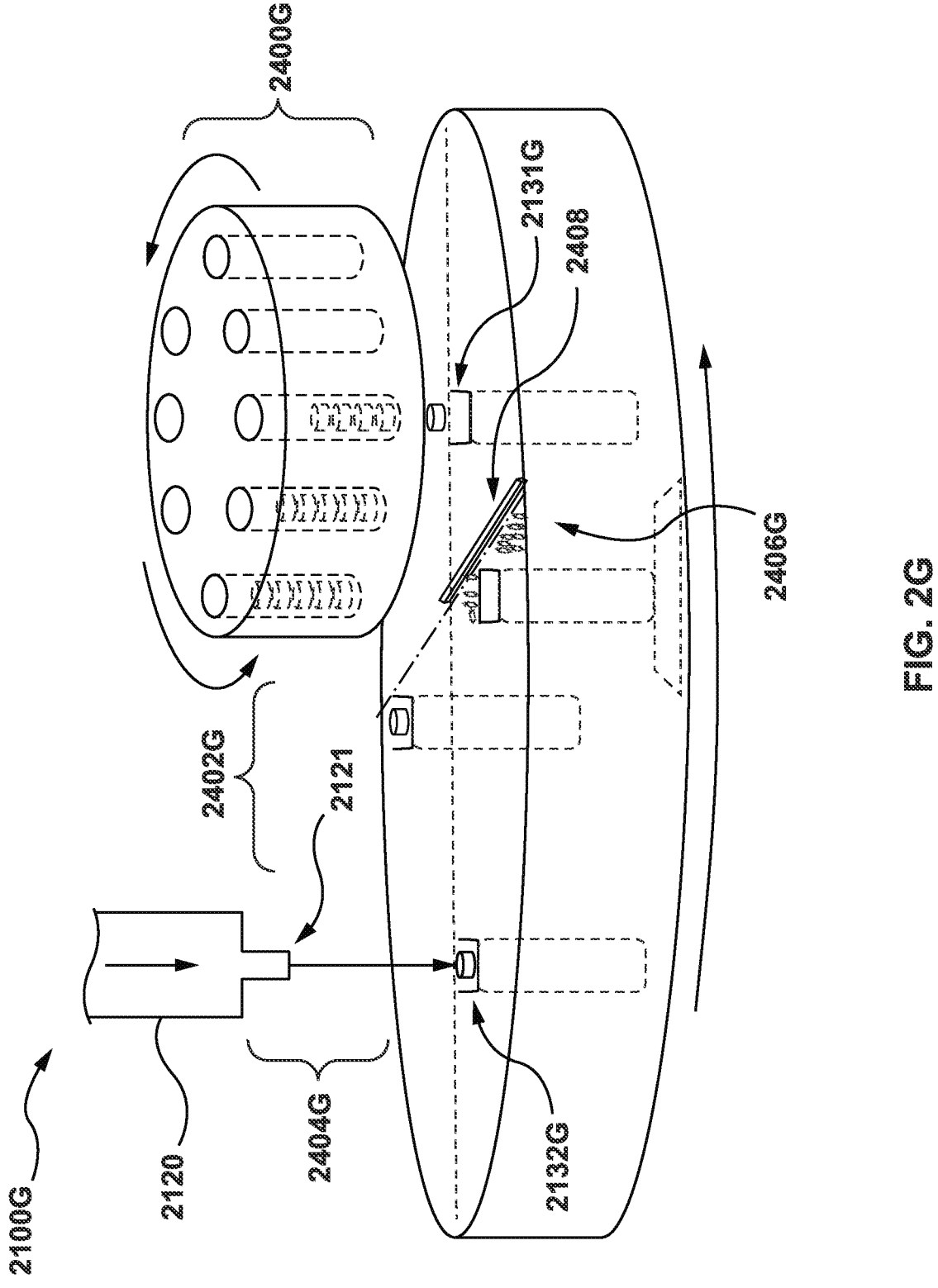
FIG. 2G depicts a carousel for dispensing tablets, and depicts a scraper-based clearing system according to an embodiment herein.

In embodiments hereof, a tablet testing apparatus 2100F, 2100G may include a sample filling station 2400F, 2400G, such as that illustrated in FIGS. 2F and 2G. In the examples of FIGS. 2F and 2G, the sample filling station 2400F, 2400G may form a carousel for dispensing one or more tablets onto one or more locations on an impact platform thereof. In some instances, a sample filling station 2400G may dispense one tablet at a time to locations 2131G (also referred to as tablet dispensed locations) of an impact platform 2130G, as illustrated in FIG. 2G. In some instances, a sample filling station 2400F may be configured to dispense multiple tablets at the same time to multiple tablet dispensed locations 2131F of an impact platform 2130F, as illustrated in FIG. 2F. In some instances, a tablet dispensed location may be a well or other indentation within a surface of the impact platform 2130F, 2130G, wherein the well may hold a dispensed tablet. In the example of FIG. 2F, the multiple tablet dispensed locations 2131F may be arranged in a line (e.g., row) of wells. In some instances, the sample filling station 2400F, 2400G may be configured as carousels with slots, wherein each of the slots may contain a respective set of tablets to be dispensed. For example, each slot may be used to contain a different type of tablet.

In embodiments hereof, the impact platforms 2130F, 2130G in FIGS. 2F and 2G may be rotatable, so as to rotate one or more dispensed tablets from the one or more tablet dispensed locations 2131F, 2131G to one or more impact sites 2132F, 2132G. In some instances, the impact platform 2130F, 2130G may rotate the one or more dispensed tablets to an intermediate position, or more specifically to an alignment station 2402F, 2402G. At the alignment station 2402F, 2402G, the tablet testing apparatus may, e.g., include a tablet placement mechanism that uses a pair of push components or multiple pairs of push components to ensure that a single dispensed tablet or multiple dispensed tablets are centered at desired locations, such as respective centers of the wells into which they are dispensed. Such an alignment operation may better ensure that, when the dispensed tablets are rotated to an impact testing station 2404F, 2404G they are centered directly below respective tips 2121A, 2121B, 2121C, 2121D, 2121E of a striker component 2120E, as shown in FIG. 2F, or below a tip 2121 of a striker component 2120, as shown in FIG. 2G.

In embodiments hereof, the impact testing station 2404F, 2404G are configured to include one or more impact sites which may receive impact from one or more tips of a striker component 2120, 2120E when the striker component falls toward the impact platform 2130F, 2130G. The striker component 2120, 2120E may be used as part of an impact strike test, as disclosed herein, which may be intended to break the dispensed tablets when the tablets are rotated to the impact testing station.

In embodiments hereof, the rotatable impact platform 2130F, 2130G may be configured to further rotate the one or more dispensed tablets, after they have been broken or otherwise struck by a respective striker component, from the impact testing station 2404F, 2404G to a clearing station 2406F, 2406G. The clearing station 2406F, 2406G may be configured to remove debris or other fragments of the one or more dispensed tablets (which may now be broken tablets) toward a site within an impact chamber, so as to prevent the debris or other fragments of the broken tablets from contaminating other regions of the tablet testing apparatus 2100F, 2100G. In the example of FIG. 2F, the clearing station 2406F may include a vacuum that is configured to generate negative pressure, which may suck the debris or other fragments of the broken tablets toward, e.g., a waste compartment of the tablet testing apparatus 2100F. In such an example, the tablet testing apparatus 2100F may be airtight, so as to facilitate the creation of negative pressure in an impact chamber thereof (relative to a remaining region of the tablet testing apparatus). In the example of FIG. 2G, the clearing station 2406G may include a scraper 2408 that is configured to clear debris or other fragments of one or more broken tablets from a top surface of the impact platform 2130G. The debris or other fragments may be, e.g., scraped to fall toward a waste compartment that is located below the impact platform 2130G.

In embodiments hereof with further reference to FIGS. 2B and 2C, a striker mechanism 2113 may be configured to releasably suspend the striker component 2120 within the housing 2110 and above the impact site 2132. For instance, the striker mechanism 2113 may include a base 2113C, which may be an apparatus, block, or other object from which the striker component 2120 is hung or otherwise suspended. In some implementations, the base 2113C may include a movable latch, stopper, or other component on which the striker component 2120 rests. Such a component may prevent the striker component 2120 from falling towards the impact site 2132. In an embodiment, a base 2113C may include an actuator, such as a solenoid, which is configured to retract or otherwise move a latch or stopper to a position in which it no longer supports a striker component 2120. Such a movement of the latch or stopper may release the striker component 2120, thus permitting the striker component 2120 to fall towards the impact site 2132. In some cases, the actuator in this example may be activated, deactivated, or otherwise controlled based on a user command, such as a user command received via the user input device 2170. For example, the user input device 2170 may provide a user interface which allows a user to input a user command to trigger the dropping of the striker component 2120. In such an example, the actuator in the base 2113C may be activated in response to the user command.

In an embodiment, a base 2113C may be a lifter device (also referred to as a tup lifter) that is configured to control a height at which a striker component 2120 is suspended above an impact site 2132, and thus a release height RH at which the striker component 2120 is released (also referred to as a drop height) to drop towards the impact site 2132. Raising the release height RH may increase an amount of energy or impact force that a striker component 2120 of a suitable/certain mass will impart to the tablet 2300 at the impact site 2132, while lowering the release height may decrease the amount of energy or impact force that the striker component 2120 of a suitable/certain mass will impart to the tablet 2300. In embodiments in accordance herewith, a desired impact force may be achieved by selecting an appropriate release height RH for a mass of the striker component, wherein any desired impact force may be achieved by properly selecting a weight of the striker component and a respective release height to provide the desired impact force at an impact site. In some implementations, the base 2113C may control the release height RH of the striker component 2120 by moving or being moved along one or more rails 2113A, 2113B, which may form a support frame or support structure of the striker mechanism 2113. More particularly, the one or more rails 2113A, 2113B may be or may include elongated bars or rods that guide movement of the base 2113C as the base 2113C raises or lowers the striker component 2120. In an embodiment, the mechanism 2130 may include an actuator, such as a motor or pneumatic actuator, that is configured to generate a force for raising or lowering the base 2113C along the one or more rails 2113A, 2113B. This actuator may be disposed within the base 2113C, or may be disposed elsewhere within the housing 2110, or even outside the housing 2110. If the actuator is disposed outside of the base 2113C, the tablet testing apparatus 2100 may include a transmission component, such as a chain, that is configured to transmit the force generated by the actuator to the base 2113C. If the actuator is disposed within the base 2113C, such an actuator may be separate from any actuator used to release the striker component 2120 from the base 2113C.

In an embodiment, a tablet testing apparatus 2100 may have a size that is sufficiently small to render the apparatus suitable as a benchtop or tabletop instrument, such as a benchtop tablet testing apparatus 2100BB shown in front and side views in FIG. 2BB. The benchtop tablet testing apparatus 2100BB includes a housing 2110BB that may have a relatively short height, for instance a height H of 130 cm to 140 cm, that is more suitable for placement and operation on a laboratory bench or table. In one example, the height H may limit a maximum distance by which a striker component (not shown), which may be weighted as described above, can be releasably suspended (a release height RH) above an impact site 2132BB to be 120 cm, 110 cm, 100 cm, 90 cm, 80 cm, 70 cm, 60 cm, 50 cm, 40 cm, 30 cm, 20 cm, 10 cm, 5 cm, or less. As an example, a height H of the housing 2110BB may be 140 cm, 130 cm, 120 cm, 110 cm, 100 cm, 90 cm, 80 cm, 70 cm, 60 cm, or a smaller value. The reduced release height RH discussed above may require a strike component of greater mass to provide a sufficient impact force at an impact site for an impact strike test to be performed, or more specifically sufficient to break a pharmaceutical tablet or other tablet during the impact strike test. The greater mass may be achieved by adding mass to an existing striker component, as previously discussed, or may be achieved by selecting a striker component of a heavier material. The benchtop tablet testing apparatus 2100BB may include all or most of the features described herein with reference to the tablet testing apparatus 2100, 3100, for instance, one or more chambers, such as a striker component chamber and an impact chamber, a striker mechanism for releasably suspending a striker component above the impact chamber, additional mass or weight for adding to the striker component, an impact platform situated within the impact chamber and having a tablet placement mechanism, wherein each of these structures is suitably sized for a bench or table top application.

In an embodiment, a tablet testing apparatus 2100 may include a sensor data acquisition system 2140, as illustrated in FIG. 2C, which may be an embodiment of the sensor data acquisition system 1140, that is configured to generate sensor data which measures various aspects of an impact strike test. For instance, the sensor data acquisition system 2140 may include at least a sensor 2141 and a sensor 2142. The sensor 2141 may be, e.g., a strain gauge force sensor or other sensor configured to measure an impact force which the striker component 2120 imparts to the tablet 2300 or other object at the impact site 2132 when the striker component 2120 collides with, impacts, or otherwise strikes the object. In one example, as depicted in FIG. 2C, the sensor 2141 may be disposed at the tip 2121 of the striker component 2120. In an embodiment, a sensor 2142 may be a laser sensor or other sensor configured to measure kinetic energy or speed of a striker component 2120 as the striker component 2120 falls or otherwise moves toward an impact site 2132. In some cases, the sensor data acquisition system 2140 may include a communication circuit 2143 which is configured to receive or collect sensor data generated by the sensors 2141, 2142 via a wired or wireless connection 2144. If the sensor data is processed by the computing system 1200 of FIGS. 1A and 1B, the computing system 1200 may receive the sensor data via the communication circuit 2143. In an embodiment, a sensor (e.g., 2141) of the sensor data acquisition system may be disposed on or within the impact platform and configured to measure a force by which the striker component 2120 impacts the impact site 2132. In certain implementations, the sensor may be statically located at a fixed location, such as directly below the impact site 2132 and within the impact platform.

Figure 3A:
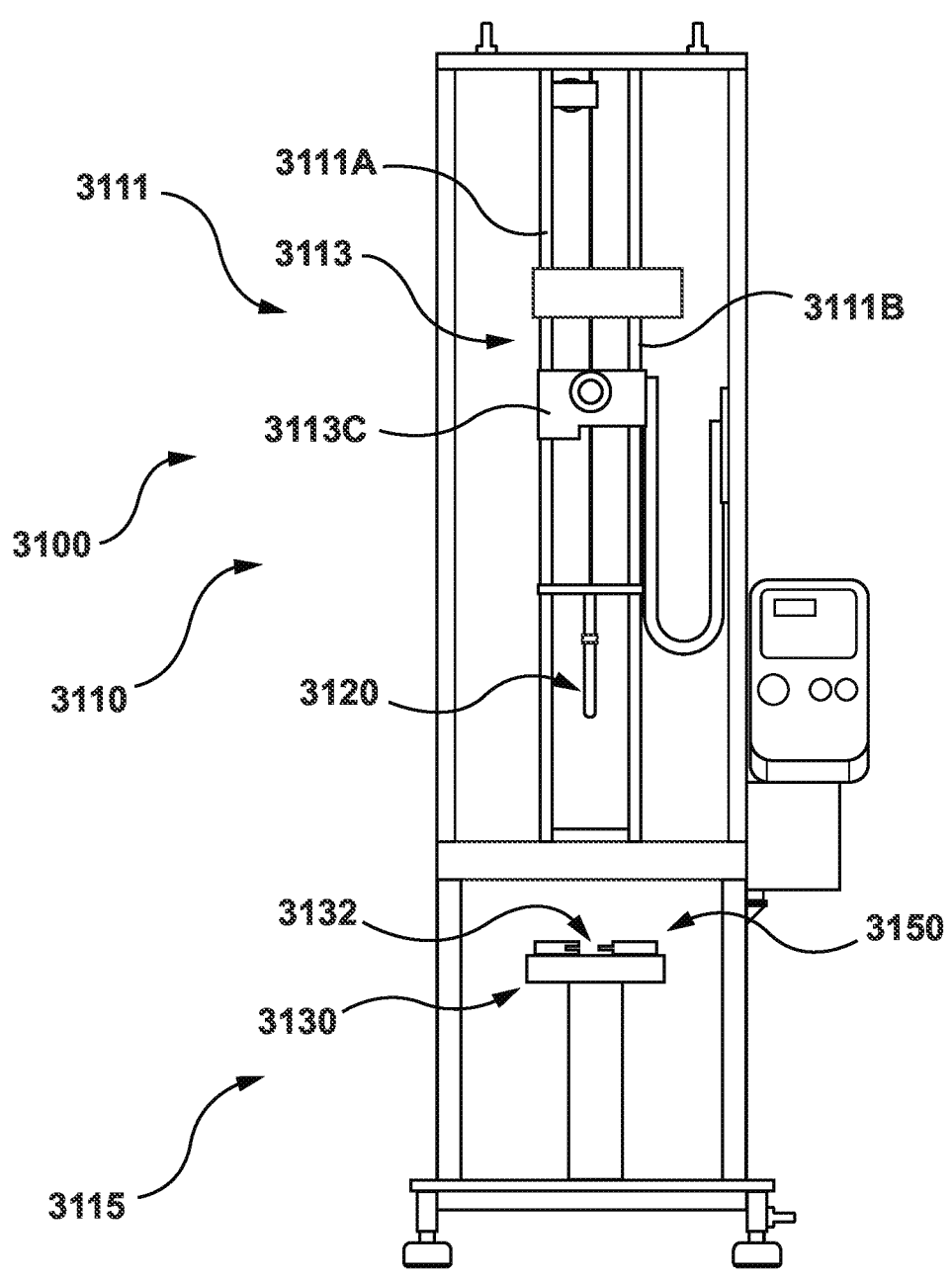
FIG. 3A depicts a tablet testing apparatus according to an embodiment herein.

FIG. 3A illustrates a tablet testing apparatus 3100, which may be an embodiment of the solid pharmaceutical dosage form or tablet testing apparatus 1100, 1100A, 2100, that includes a housing 3100 that forms a striker component chamber 3111 and an impact chamber 3115. The striker component chamber 3111 may include a striker component 3120 and a mechanism 3113 that is configured to releasably suspend the striker component 3120 above the impact chamber 3115. The impact chamber 3115 may include an impact platform 3130 and a tablet placement mechanism 3150 disposed on an upper surface of the impact platform 3130. In some instances, the components depicted in FIG. 3A may be an embodiment of similar components discussed above with respect to the embodiment depicted in FIGS. 2A-2C.

Figure 3B:
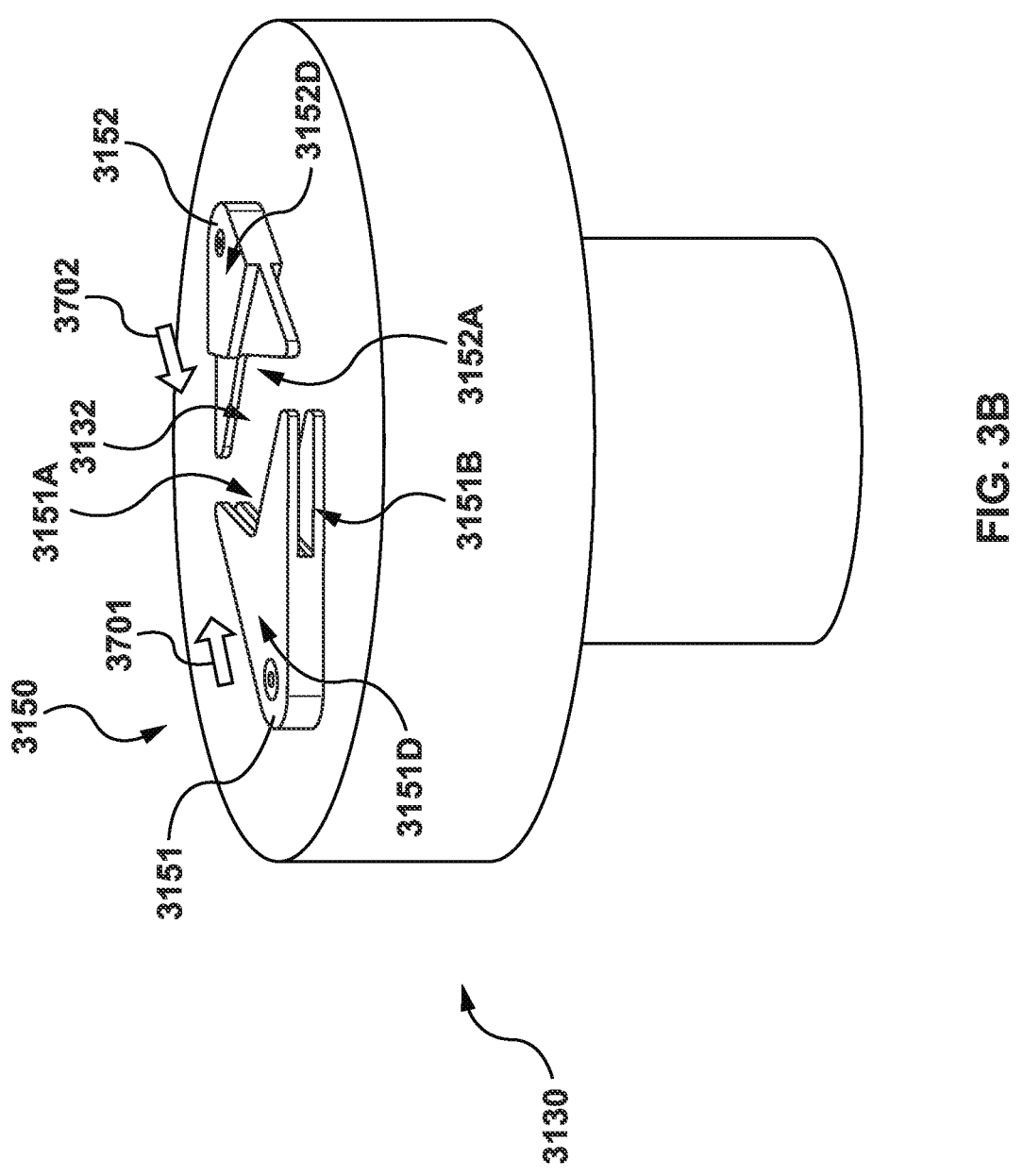
FIGS. 3B-3D depict a tablet placement mechanism according to an embodiment herein.
Figure 3C:
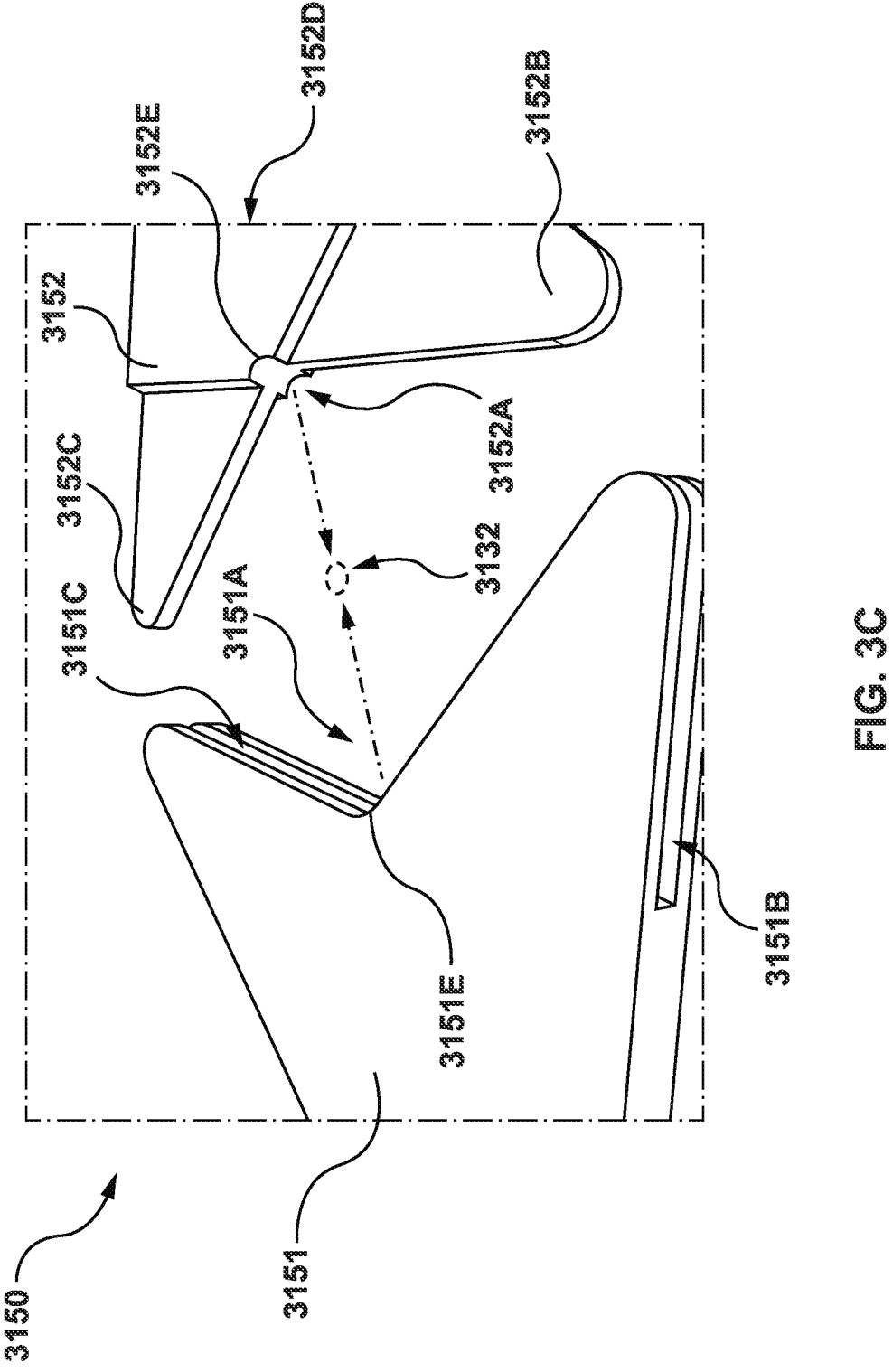
Figure 3D:
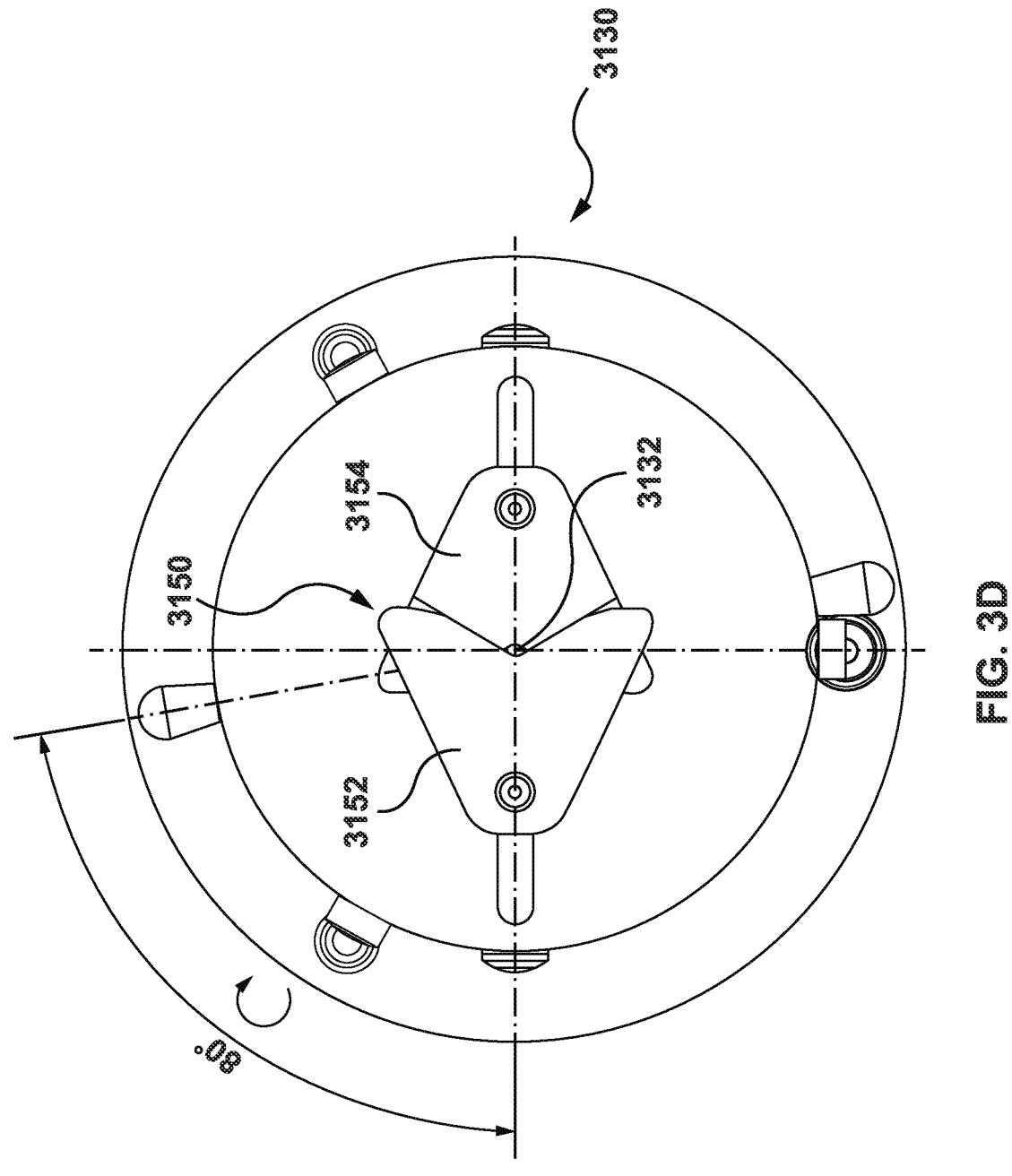

As stated above, the solid pharmaceutical dosage form or tablet testing apparatus 1100/2100/3100 may include a solid dosage form or tablet placement mechanism 1150/2150/3150. FIGS. 3B and 3C depict an embodiment of a tablet placement mechanism 3150 that may be configured to push or otherwise move a tablet toward an impact site, or more specifically to place the tablet so that it is centered around the impact site. Such a placement may cause the tablet to be placed directly under a striker component before a start of an impact strike test. More particularly, the tablet placement mechanism 3150 may be disposed on an upper surface of the impact platform 3130, and may include a first push component 3151 and a second push component 3152 that are attached or otherwise coupled to the upper surface of the impact platform 3130. In this example, the impact site 3132 may be located between the first push component 3151 and the second push component 3152. The first push component 3151 and the second push component 3152 in this example may be movable toward each other manually or via an actuator (e.g., motor) along directions indicated by the arrows 3701, 3702 in FIG. 3B. More particularly, the tablet placement mechanism 3150 may have an open configuration, as illustrated in FIGS. 3B and 3C, in which the first component 3151 and the second component 3152 have a space therebetween for placement of a tablet in the space. The tablet placement mechanism 3150 may be movable or adjustable from the open configuration to a closed configuration (e.g., via the motor), which is illustrated in FIG. 3D, by moving the push components 3151, 3152 closer to each other and to the impact site 3132, so as to push a tablet or other object toward the impact site 3132, and more specifically to cause the tablet to be centered around the impact site 3132. In some instances, the first push component and the second push component may be equidistant from the impact site, so that when they are moved toward each other by equal amounts, they cause the tablet to be pushed toward the impact site. Once the tablet has been centrally placed at the impact site 3132, the push components 3151, 3152 may also be moved back to the open configuration, in which the push components 3151, 3152 are moved away from the tablet such that they are no longer be in contact with the tablet.

In some instances, the impact platform 3130 may include one or more coupling components, such as springs, which couple the first push component 3151 and the second push component 3152 to the impact platform 3130, but still permit the first push component 3151 and the second push component 3152 to move toward each other or away from each other along the upper surface of the impact platform 3130.

In an embodiment, a first push component 3151 may have a first recessed portion 3151A, which may provide a recess that may be used to engage one side (e.g., left side) of a tablet if the tablet is on a particular side (e.g., left side) of an impact site. In such a scenario, as the first push component 3151 is moved in a rightward direction toward the second push component 3152, the first push component 3151 may also push the tablet in the rightward direction towards the impact site. Similarly, a second push component 3152 may have a second recessed portion 3152A, which may provide a recess that may be used to engage another side (e.g., right side) of the tablet. As the second push component 3152 is moved in a leftward direction toward the first push component, if the tablet is on the other side (e.g., right side) of the impact site, the second push component 3152 may push the tablet in the leftward direction towards the impact site. More particularly, a recess formed by the first recessed portion 3151A of the first push component 3151 may extend inwardly toward an interior 3151D, such as a center, of the first push component 3151, to thereby extend away from the impact site 3132. Similarly, a recess formed by the second recessed portion 3152A of the second push component 3152 may extend inwardly toward an interior 3152D of the second push component 3152, to thereby extend away from the impact site 3152. As depicted in FIGS. 3B and 3C, the first push component 3151 and the second push component 3152 may surround the impact site 3132, such that the impact site 3132 may be located between the first recessed portion 3151A of the first push component 3151 and the second recessed portion 3152A of the second push component 3152. More specifically, the impact site may remain as a center location of a space between the first push component 3151 and the second push component 3152. When the first push component 3151 and the second push component 3152 are moved toward each other, the movement may position the first recessed portion 3151A and the second recessed portion 3152A at the impact site 3132, and thus place a tablet at the impact site 3132, such that the tablet is centered around impact site 3132.

In an embodiment, a first push component 3151 and a second push component 3152 may be well suited for engaging a tablet and centering or otherwise placing the tablet at the impact site 3132. More specifically, various tablets may have convex sides or, more generally, a convex shape. For example, some tablets may have a circular or elliptical shape, in which opposite sides curve outward. The first push component 3151 and the second push component 3152 may have concave shapes which complement the convex shape of the tablets. As an example, the first recessed portion 3151A of the first push component 3151 in FIGS. 3B and 3C may form a first concave corner 3151E that is configured to engage a first convex side of a tablet. In this example, the second recessed portion 3152A of the second push component 3152 may form a second concave corner 3152E that is configured to engage a second convex side of the tablet. The concave corners 3151E, 3152E may each be a curved corner that have a degree of curvature, or may each be a sharper corner with no degree of curvature. The concave corners 3151E, 3152E may cause the tablet, when it engages one or both of the corners, to be pushed toward the impact site 3132 as the first push component 3151 and the second push component 3152 are moved toward each other. In an embodiment, a first push component 3151 and a second push component 3152 may be located such that an impact site 3132 is equidistant from the push components 3151, 3152. For example, the impact site 3132 may be equidistant from the first concave corner 3151E and the second concave corner 3152E.

In an embodiment, a first push component 3151 and a second push component 3152 may have complementary portions which temporarily mate with or otherwise engage each other when a tablet placement mechanism 3150 moves from an open configuration to a closed configuration, so as to allow the push components 3151, 3152 to approach the impact site to a sufficiently close distance to centrally place a tablet at the impact site. For instance, as depicted in FIG. 3C, the first recessed portion 3151A of the first push component 3151 may form one or more slots 3151B. 3151C. The one or more slots 3151B, 3151C may be configured to receive the second recessed portion 3152 when the first push component 3151 and the second push component 3152 are moved toward each other. More specifically, the second recessed portion 3152 may include a first sub-portion 3152B and a second sub-portion 3152C that protrude from the second push component 3152. In this example, the slot 3151B may be configured to receive the first sub-portion 3152B, while the slot 3151C may be configured to receive the second sub-portion 3152C. In other words, the sub-portions 3152B, 3152C may be slidable into the slots 3151B, 3151C. These complementary structures of the first push component 3151 and the second push component 3152 may permit them to move close to each other and close to the impact site 3132, so as to push an object toward the impact site 3132, and to be centered around the impact site 3132 as illustrated in FIG. 3D. In an embodiment, once the push components 3151, 3152 have moved from the open configuration to the closed configuration, so as to place a tablet or other object at the impact site 3132, the push components may return to the open configuration. When the push components are returning to the open configuration, they may disengage from the tablet, so that they are not in contact with the tablet when a striker component is falling toward the tablet during an impact strike test.

Figure 4A:
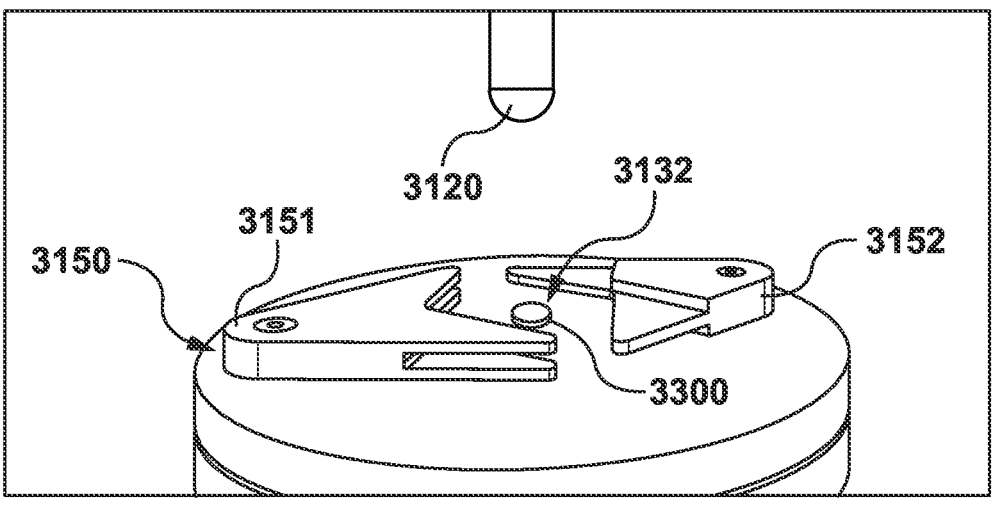
FIGS. 4A-4C depict an impact strike test being performed with a tablet testing apparatus according to an embodiment herein.
Figure 4B:
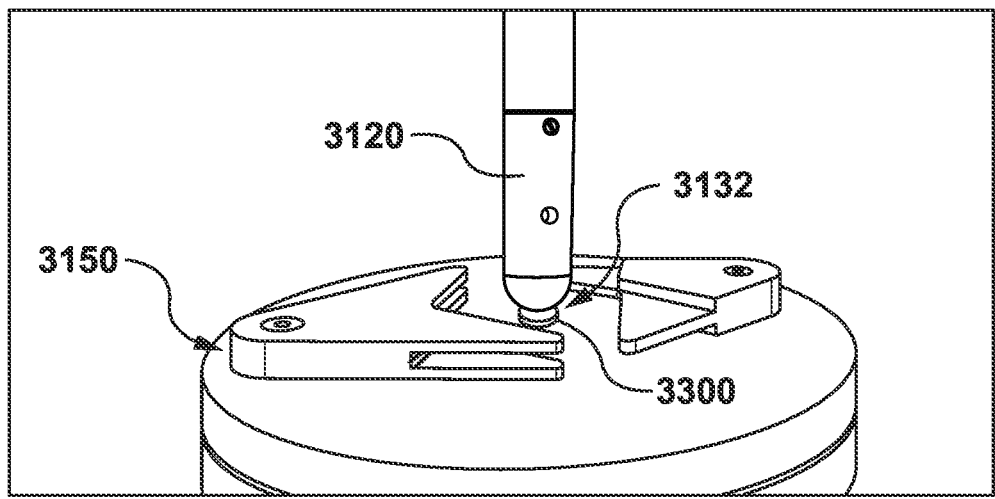
Figure 4C:
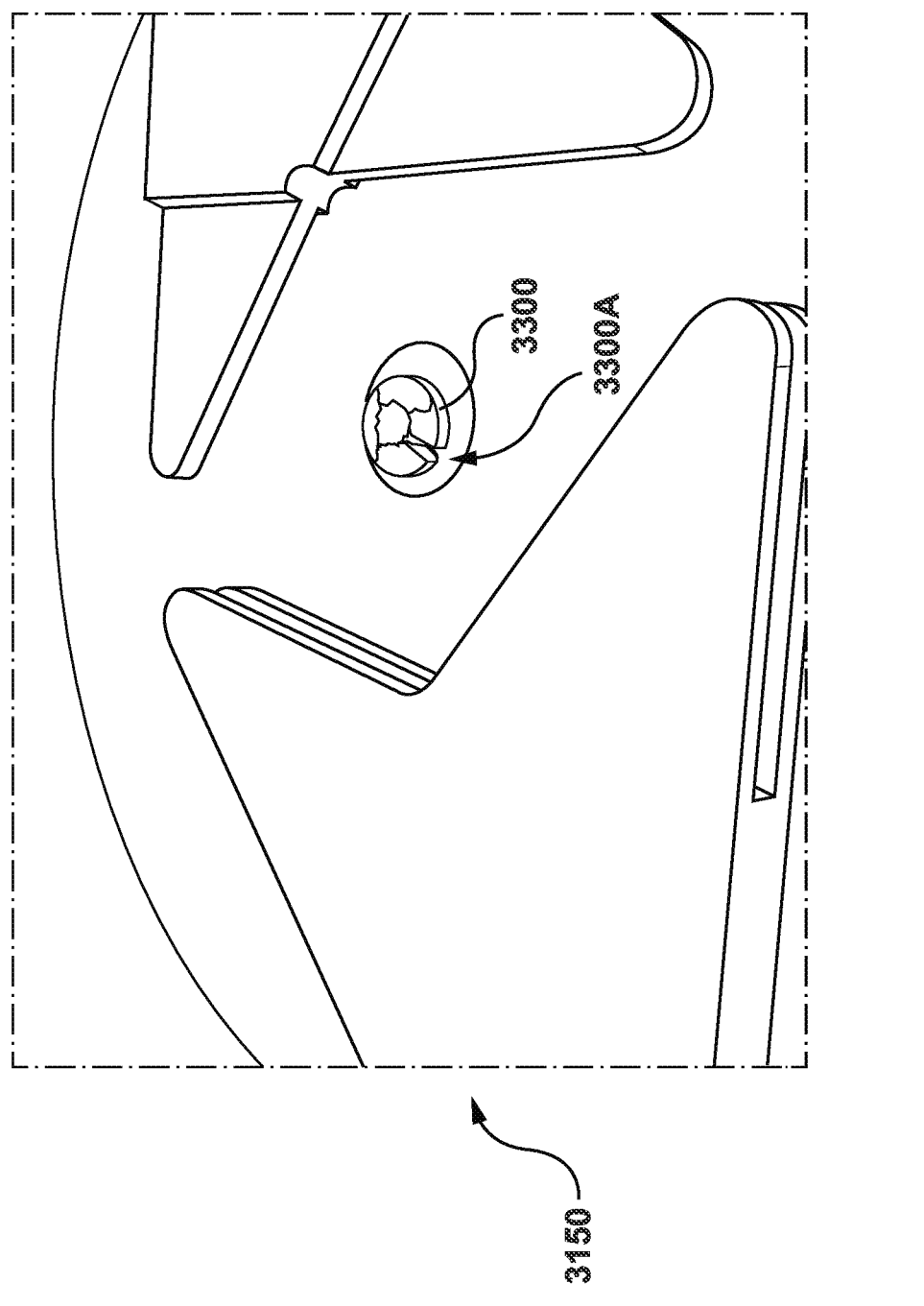

FIGS. 4A and 4B illustrate a striker component 3120 striking a tablet 3300, by being dropped on the tablet 3300 under the influence of gravity. FIGS. 4A and 4B depict a scenario in which the tablet placement mechanism 3150 is shown in an open configuration while the striker component 3120 is being dropped or falling on the tablet 3300, such that the tablet placement mechanism 3150 is disengaged from the tablet 3300 while the striker component 3120 is being dropped or falling on the tablet 3300. In such a configuration, the tablet placement mechanism 3150, or more specifically the first push component 3151 and the second push component 3152, may avoid interfering with the striker component 3120, and avoid interfering with measurements of how much force is imparted from the striker component 3120 to the tablet 3300. FIG. 4C illustrates a result of an impact strike test being performed on the tablet 3300. More particularly, the impact strike test may involve the striker component 3120 having sufficient mass and/or being released from a sufficient height so that, when the striker component 3120 is released and impacts the tablet 3300, the striker component 3120 imparts enough force or energy to break the tablet 3300. For instance, FIG. 4C illustrates a gap 3300A in the tablet 3300 that is created when a portion of the tablet 3300 breaks off from the tablet 3300 as a result of the force of impact from the striker component 3120. As discussed below in more detail, some embodiments herein may involve detecting a tablet breakage event by determining, based on measurements made with sensor data, whether a tablet has in fact been broken as a result of the impact strike test.

As stated above, the impact chamber 1115, 2115, 3115 may surround an impact site 2132, 3132 and may be used to contain debris that may be created during an impact strike test. For instance, the impact from a striker component, e.g. 2120), may create debris in the form of a dispersed powder. The powder may contain pharmaceutical substances that may have adverse health effects if exposed to personnel outside of the housing 1110, 2110, 3100 of the solid pharmaceutical dosage form or tablet testing apparatus. Thus, the impact chamber 1115, 2115, 3115 may be used to trap the debris therewithin. In an embodiment, as illustrated in FIG. 2F, the impact chamber may be connected to a vacuum to create negative pressure and prevent any contaminated air from escaping the impact chamber.

Figure 5:
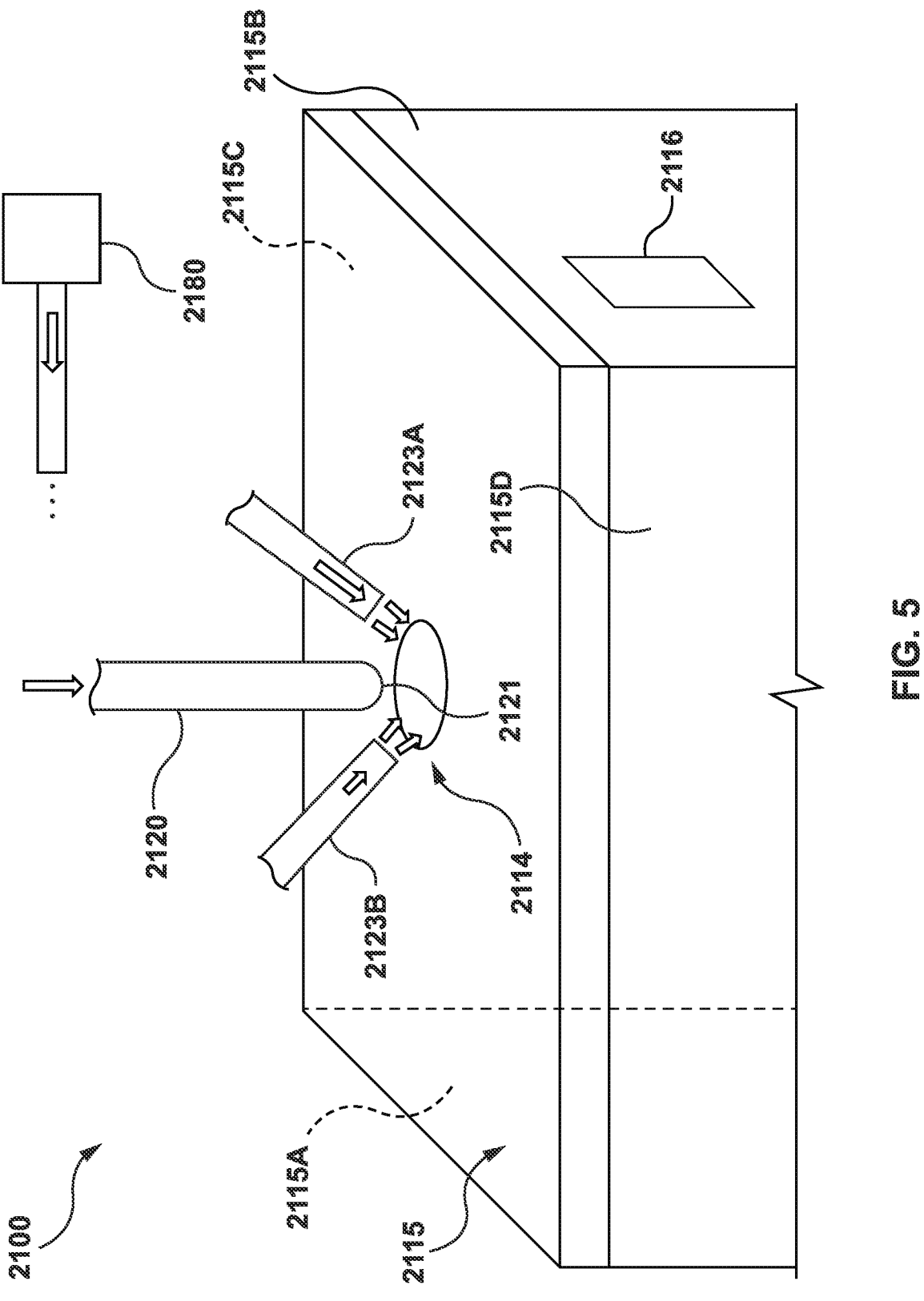
FIG. 5 depicts an air flow generator for applying air flow toward an opening of an impact chamber according to an embodiment herein.

For instance, FIG. 5 illustrates the tablet testing apparatus 2100 that is configured to generate air flow that may keep the debris from escaping the impact chamber 2115. More particularly, the tablet testing apparatus 2100 may include the opening 2114, or more specifically a hole, which allows the striker component 2120 to pass into the impact chamber 2115 and to reach the impact site 2132. In this embodiment, the impact chamber 2115 may have walls 2115A, 2115B. 211C, and 2115D that are connected to each other in an airtight manner, and connected to a top wall and bottom wall in an airtight manner. In one example, walls 2115D and 2115C may be a front wall and a back wall, respectively, of the impact chamber 2115, while walls 2115A and 2115B may be side walls, respectively, of the impact chamber. Thus, the walls 2115A, 2115B, 2115C, and 2115D may prevent the debris from escaping the impact chamber 2115 in a lateral direction. However, the debris may escape through the opening 2114. To reduce the likelihood of such an occurrence, the tablet testing apparatus 2100 may include air flow generator 2180, such as a fan or a pneumatic pump, or a conduit that is connected to compressed air, that is configured to generate an air flow. In this embodiment, the tablet testing apparatus may have one or more channels 2123A, 2123B (e.g., tubes, hoses, or pipes) are directly or indirectly connected to the air flow generator 2180. The one or more channels 2123A, 2123B may have an outlet around the opening 2114, and may allow air flow generated by the air flow generator 2180 to reach a region which is close to the opening 2114 (e.g., right above the opening 2114, as illustrated in FIG. 5). Thus, the air flow generator 2180) and the one or more channels 2123A. 2123B may apply air pressure into the impact chamber 2115 via the opening 2114. The air pressure may reduce the likelihood of the debris escaping from the impact chamber 2115. In some implementations, the impact chamber 2115 may include a filter 2116 that provides an outlet for the air flow which enters the impact chamber 2115 via the opening 2114. The filter 2116 may be configured to filter out any debris which was created by the impact strike test and is being carried by the air flow, thus further preventing the debris from escaping the impact chamber 2115. In some implementations, an impact chamber 2115 may be configured to provide environmental control. More specifically, the impact chamber 2115 may be configured to control a temperature or other environmental condition at an impact site, so as to create a standardized condition for an impact strike test.

FIG. 6 illustrates a method 6000 which may use a tablet testing apparatus to evaluate the strength of a tablet or a sample or subset of a batch of tablets. The method may involve determining how much impact force various tablets are able to absorb or otherwise withstand before physically breaking. In an embodiment, the method 6000 may involve determining a relationship between such an impact force and a physical defect rate that indicates a likelihood that the tablets will experience a physical defect in a particular circumstance or set of circumstances. In some cases, the method 6000 may use this relationship to predict a physical defect rate for another circumstance and/or another batch of tablets or type of tablets. In an embodiment, the method 6000 may be performed by, e.g., a manufacturing facility that manufactures pharmaceutical tablets or other tablets, and/or a research/development facility, or more specifically by personnel at the facility. In some cases, method 600 may be performed as part of a tablet manufacturing process or tablet (formulation) development.

In an embodiment, a method 6000 may begin with or otherwise include a step 6002, in which an impact strike test is performed on a first plurality of tablets or a first plurality of sets of tablets. In some cases, the first plurality of tablets or the first plurality of sets of tablets may be associated with a plurality of tablet types that have different physical characteristics. In other words, each tablet of the first plurality of tablets may be associated with a respective tablet type of the plurality of tablet types, or each set of tablets of the first plurality of sets of tablets may be associated with a respective tablet type of the plurality of tablet types. For example, if the impact strike test is performed on a first plurality of tablets, the first plurality of tablets may include a first tablet that belongs to a first tablet type. e.g., a tablet type 1, a second tablet that belong to a second tablet type. e.g., a tablet type 2, etc. If the impact strike test is performed on a first plurality of sets of tablets, the first plurality of sets of tablets may include a first set of tablets. e.g., 10 or 20 tablets, that belongs to the first tablet type, a second set of tablets that belongs to the second tablet type, etc. Thus, the impact strike test may be used to generate sensor data associated with different tablet types.

In some cases, a tablet type may be associated with a batch of manufactured tablets. In other words, tablets of the same batch may belong to a common tablet type. In some instances, a physical characteristic for a tablet type may refer to a physical structure for tablets associated with the tablet type, such as a shape and/or size of the tablets. For example, the shape of the tablets may refer to whether the tablets have an elliptical shape or a circular shape, and/or whether the tablets have a flat surface. In some instances, a physical characteristic for a particular tablet or tablet type may be affected by, e.g., a formulation of the tablet or tablet type, a shape of the tablet, and/or a manner in which the tablet is manufactured. A manner in which a tablet is manufactured may refer to or may be affected by a parameter value or manufacturing technique used to manufacture the tablet. For example, if the tablet is manufactured based on compressing a powder, a parameter value may involve an amount of compression pressure used to compress the powder. The powder may be compressed directly by direct compression or it may be granulated to form granules using dry granulation or wet granulation techniques before compression. In such examples, the manner of manufacturing the tablet may affect a physical characteristic, such as porosity, of the tablet or tablet type. In another example, a manner in which a tablet is manufactured may refer to use of a coating process on a tablet core that may subject the tablet core to various forces. In such an example, the manner of coating the tablet may further affect a physical characteristic, such as a porosity, of the tablet or tablet type. In yet another example, a manner in which a tablet is manufactured may refer to use of molding or additive manufacturing such as 3D printing using, for example, hot melt extrusion.

In an embodiment, a tablet's formulation may refer to which materials are included in the tablet, or more generally to a qualitative and/or quantitative composition of the tablet. The materials included in a tablet may be divided into one of the categories of active pharmaceutical ingredient (API) or excipient. Excipients in a tablet formulation may further be classified into one or more of the following categories: filler, disintegrant, binding agent (solution binder or dry binder), glidant, lubricant/anti-adherent. (See, e.g., M. E. Aulton, Pharmaceutics—The science of dosage form design, second edition).

In an embodiment, a qualitative composition describing a tablet formulation may list such classes of excipients and/or specific substances. Examples of fillers include: MCC (e.g., MCC Avicel PH 102101, Emcocel 90M, etc.), mannitol (e.g., Pearlitol 50c, Pearlitol 120c or Pearlitol 160c). Examples of disintegrants include sodium starch glycolate, for example ExploTab or Glycolys LV. Examples of binding agents include Plasdone K29/32. Povidone and Kollidon K30. Examples of glidants include colloidal silica and talc. Examples of lubricants include magnesium stearate and glyceryl dibehenate.

In an embodiment, a quantitative composition may list the specific substances alongside the amount of each substance. Amounts may be expressed as a weights or percentages. Fillers, when employed, range between for example about 10 to about 75 weight percent (e.g. about 15 to about 70 weight percent) of the dry formulation: disintegrants, when employed, range from between about 0.5 and 10.0 weight percent (e.g. about 5 weight percent) of the dry formulation: binding agents, when employed, range between for example about 2 to about 8 weight percent of the dry formulation: glidants, when employed, range between about 0.1 and 10.0 weight percent of the dry formulation: lubricants, when employed, range from between about 0.25 and 2.5 weight percent of the dry formulation.

In some examples, a filler (also referred to as a diluent/carrier) for use in peroral formulations, such as those in the form of immediate release tablets, may include monobasic calcium phosphate, dibasic calcium phosphate (including dibasic calcium phosphate dihydrate and dibasic calcium phosphate anhydrate), tribasic calcium phosphate, lactose, microcrystalline cellulose, silicified microcrystalline cellulose, mannitol, sorbitol, starch (such as maize, potato or rice), glucose, calcium lactate, calcium carbonate and the like. In one example, the diluents/carriers may include dibasic calcium phosphate and microcrystalline cellulose, which may be used alone or in combination with another diluent/carrier, such as mannitol. In an embodiment, a formulation of an immediate release tablet may comprise one or more excipients to improve the physical and/or chemical properties of a final composition of the tablet, and/or to facilitate the process of manufacture. Such excipients may be used in the formulation of immediate release formulations for peroral drug delivery, and may include one or more of the following: one or more lubricants (such as magnesium stearate, stearic acid, calcium stearate, stearyl alcohol or, sodium stearyl fumarate); a glidant (such as talc or a colloidal silica); one or more binders (such as polyvinylpyrrolidone, microcrystalline cellulose, a polyethylene glycol (PEG), a polyethylene oxide, a hydroxypropyl methylcellulose (HPMC) of a low molecular weight, a methylcellulose (MC) of a low molecular weight, a hydroxypropyl cellulose (HPC) of a low molecular weight, a hydroxyethyl cellulose (HEC) of a low molecular weight, a starch (such as maize, potato or rice) or a sodium carboxymethyl cellulose of a low molecular weight; polyvinylpyrrolidone or a HPMC of a low molecular weight for use as a binder; one or more pH controlling agents (such as an organic acid (for example citric acid) or an alkali metal (for example sodium) salt thereof, an oxide of magnesium, an alkali or alkaline earth metal (for example sodium, calcium or potassium) sulphate, metabisulphite, propionate or sorbate); one or more disintegrant (for example sodium starch glycollate, a crosslinked polyvinylpyrrolidone, a crosslinked sodium carboxymethyl cellulose, a starch (such as maize, potato or rice) or an alginate); a colorant, a flavoring, a tonicity-modifying agent, a coating agent or a preservative.

As an example, a composition of a tablet in some instances may include one or more of the following diluents: calcium phosphate (monocalcium phosphate, dicalcium phosphate and tricalcium phosphate), lactose, microcrystalline cellulose, mannitol, sorbitol, titanium dioxide, aluminum silicate and the like. In some cases, diluents include microcrystalline cellulose and also mannitol. In some instances, compositions of the tablet may contain one or more of the following lubricants: magnesium stearate, sodium stearyl fumarate, and the like. In some instances, compositions of the tablet may contain a glidant, such as a colloidal silica. In some instances, compositions of the tablet may contain one or more of the following binders: polyvinylpyrrolidone, lactose, mannitol, microcrystalline cellulose, a polyethylene glycol (PEG), a HPMC of a low molecular weight, a MC of a low molecular weight, a HPC of a low molecular weight and the like. Preferred binders include microcrystalline cellulose. In some instances, compositions of the tablet may contain one or more of the following pH controlling agents: organic acids (for example, citric acid and the like) or alkali metal (for example sodium) salts thereof, pharmaceutically acceptable salts (for example sodium, magnesium or calcium salts) of inorganic acids (such as carbonic acid or phosphoric acid), oxides of magnesium, as well as alkali, and alkaline earth metal (for example sodium, calcium, potassium and the like) sulphates, metabisulphites, propionates and sorbates. Other further excipients may include colorants, flavorings, solubilizing agents (such as SDS), coating agents, preservatives, etc.

As a further example, one formulation for a tablet may include a composition that includes materials such as microcrystalline cellulose (MCC), mannitol (MAN), and/or di calcium phosphate (CDPA). The formulation may further include a coating around a tablet core, or may lack such a coating.

Figure 7:
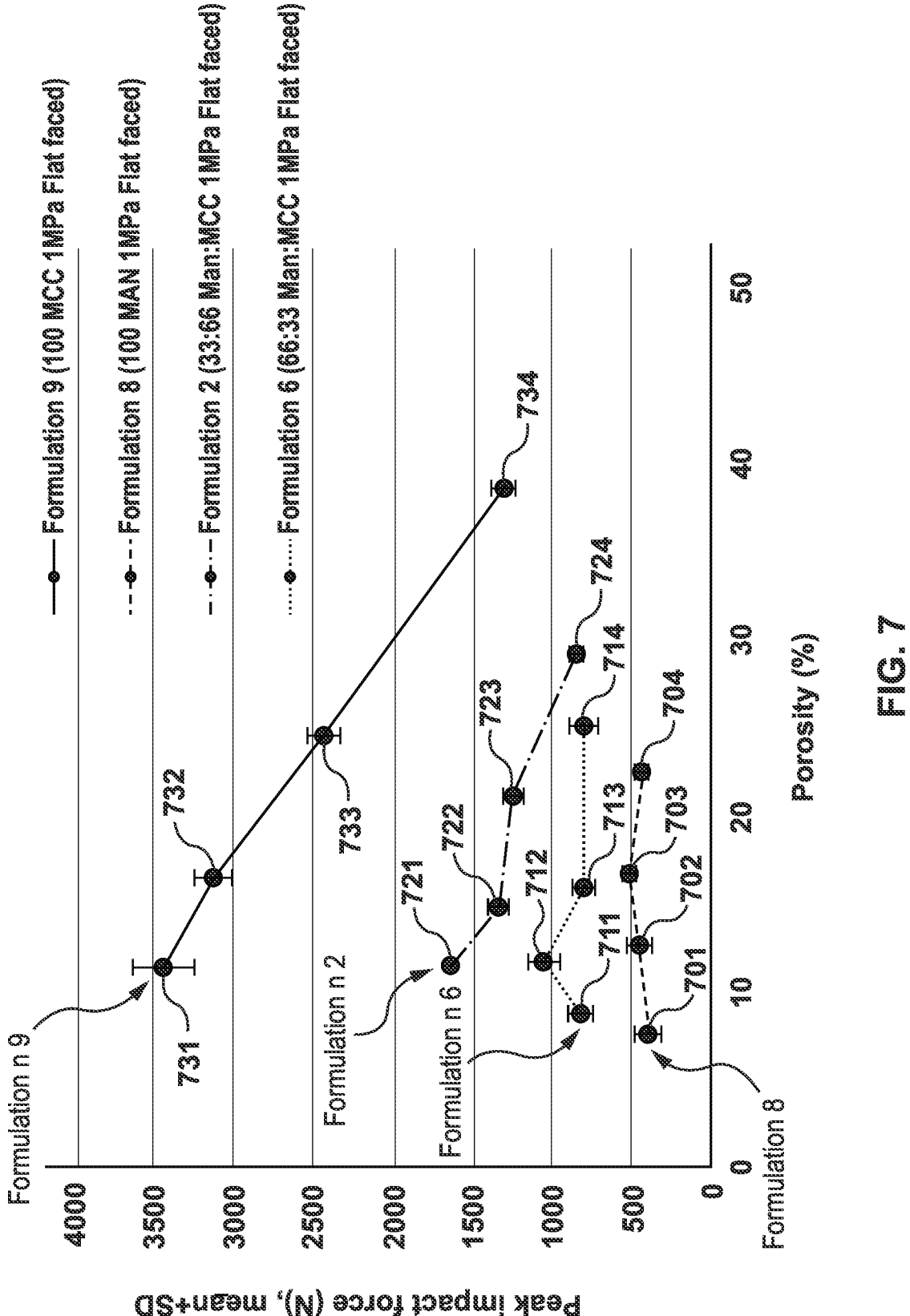
FIG. 7 illustrates peak impact force values associated with various formulations and porosities according to an embodiment herein.

Thus, in one example, different tablet types may refer to different respective formulations, or different respective combinations of formulation and porosity of the manufactured tablets. For instance, FIG. 7 illustrates various data points 701, 702, 703, 704, 711, 712, 713, 714, 721, 722, 723, 724, 731, 732, 733, 734 that are associated with different tablet types, respectively (e.g., a tablet type 1, a tablet type 2, a tablet type 3, etc.). In this example, each tablet type may be associated with a respective combination of a specific porosity and a specific formulation. As an example, the data point 701 may indicate a peak impact force value for a first tablet type associated with tablets that have a porosity of about 7.5% and a formulation in which a powder having mannitol (and no MCC) is compressed to a target tensile strength of 1 MPa to form tablets having a flat face. The peak impact force value may indicate how much impact force tablets of the first tablet type is able to absorb or otherwise withstand before breaking, as discussed below in more detail.

In an embodiment, if the impact strike test is performed on a first plurality of tablets, such an impact strike test may involve, e.g., only a single tablet per tablet type. For example, the first plurality of tablets may include a single tablet that belongs to a first tablet type, a single tablet that belongs to a second tablet type, a single tablet that belongs to a third tablet type, etc. In such an example, the impact strike test may generate, e.g., a single peak impact force value, which is discussed below, that indicates an amount of force needed to break each of the tablets. The single peak impact force value may be associated with a respective tablet type to which the broken tablet belongs.

In an embodiment, if the impact strike test is performed on a first plurality of sets of tablets, the impact strike test may generate an average peak impact force value for each of the sets. The average peak impact force value for a particular set of tablets may indicate an average amount of force needed to break the set of tablets. For example, if one of the sets includes, e.g., ten tablets that are associated with a particular tablet type, the impact strike test may be performed to determine ten respective peak impact force values needed to break the ten tablets of the set. In such an example, the impact strike test may be used to determine an average peak impact force value associated with the tablet type, wherein the average peak impact force value may be an average of the ten respective peak impact force values.

As stated above, the impact strike test may be performed with a solid pharmaceutical dosage form or tablet testing apparatus, such as apparatus 1100, 2100, 3100. For instance, the impact strike test may involve placing a first tablet or solid dosage form of the first plurality of tablets or solid dosage forms at the impact site 2132, 3132 on the impact platform 1130, 2130, 3130, and centrally placing the first tablet or solid dosage form at the impact site 2132, 3132 with the solid dosage form or tablet placement mechanism 1150, 2150, 3150. As an example, the tablet placement mechanism 1150, 2150, 3150 may be moved from the open configuration discussed above to the closed configuration in which various components of the solid dosage form or tablet placement mechanism 1150, 2150, 3150, such as the first push component 3151 and second push component 3152, are moved closer to the impact site 2132, 3132. The solid pharmaceutical dosage form or tablet testing apparatus may have a striker component 1120, 2120, 3120 that is initially suspended above the impact site 2132, and the step 6002 may involve releasing the striker component 1120, 2120, 3120 of the solid pharmaceutical dosage form or tablet testing apparatus 1100, 2100, 3100 so as to cause the striker component 1120, 2120, 3120 to fall and strike the first tablet or solid dosage form. For instance, the striker component 1120, 2120, 3120 may be released via a user command that is inputted into a user input device 2170. In this example, the impact strike test may further involve removing the first tablet or solid dosage form after it has been struck by the striker component 1120, 2120, 3120. In some cases, the removal may be performed manually. In other cases, the removal may be performed automatically. For example, the tablet testing apparatus 2100 may include a waste removal apparatus or component. The waste removal apparatus or component may include a waste filtration component that is configured to remove tablet debris or other waste, which may have been created as a result of the impact strike test, from the tablet testing apparatus 2100. In some instances, the removal may involve, e.g., moving the solid dosage form or tablet placement mechanism 1150, 2150, 3150 from a closed configuration to an open configuration.

In an embodiment, the impact strike test may repeat the above operation, step 6002, on more tablets or solid dosage forms. As an example, if the first plurality of tablets includes ten tablets associated with ten tablet types, respectively, the above operation may be repeated nine more times, so that all ten of the tablets will be placed at the impact site 2132, 3132 and be struck by the striker component 1120, 3120, 3120. As another example, if the impact strike test is performed on ten sets of tablets, wherein each set is associated with a different respective tablet type and includes five tablets, the above operation may be repeated forty-nine times, so that all fifty of the tablets will be placed at the impact site 2132, 3132 and be struck by the striker component. As yet another example, if the tablet testing apparatus includes a striker component which has multiple tips, the tablet testing apparatus may perform the impact strike test on multiple tablets simultaneously. For example, if the striker component has a 2D array of 5×5 tips (i.e., 25 tips), the tablet testing apparatus may enable the impact strike test to be performed on 25 tablets simultaneously, and may then enable the impact strike test to be repeated on another 25 tablets, to cause the impact strike test to be performed on a total of 50 tablets.

In an embodiment, an impact strike test may be performed in a manner that maximizes a likelihood that each tablet of a first plurality of tablets or first plurality of sets of tablets is broken as a result of the impact strike test. For example, the impact strike test may involve a striker component 1120, 2120, 3120 having enough total mass, e.g., 1 kg, and/or being suspended at a sufficient height, e.g., 30 cm, above the impact site 2132, 3132 to ensure that, when the striker component 1120, 2120, 3120 is released and falls toward the impact site 2132, 3132, the striker component 1120, 2120, 3120 accumulates enough momentum and/or kinetic energy during the fall so that when the striker component reaches the impact site, the accumulated momentum and/or kinetic energy is sufficient to break a tablet, e.g., by creating a gap 3300A. In an embodiment, as discussed below in more detail with respect to FIG. 8C, a computing system 1200 may be configured to detect or determine, based on sensor data that measures force profile during an impact strike test, whether a tablet has in fact been broken.

In an embodiment, a method 6000 may include a step 6004, which includes measuring, during the impact strike test, a plurality of peak impact force values that indicate respective peak amounts of impact force that a first plurality of tablets or solid dosage forms received during the impact strike test from a striker component 1120, 2120, 3120, or respective average peak amounts of impact force that a first plurality of sets of tablets or solid dosage forms received during the impact strike test. In some cases, the peak impact force may indicate a peak amount of force that a tablet withstood before breaking during the impact strike test, or an average of peak amounts of force that a set of tablets withstood before breaking during the impact strike test. The plurality of peak impact force values in this example may be associated with the first plurality of tablet types, respectively.

As stated above, the method 6000 may include detecting a tablet or solid dosage form breakage event. Such a detecting operation may involve determining, based on sensor data that measures impact force being imparted to a tablet, whether the force did in fact break the tablet. Such a determination may be made based on an impact force profile, which may refer to, e.g., a function of force imparted by the striker component onto a tablet as a function of time. More specifically, FIG. 8E illustrates impact force profiles associated with three instances in which three respective tablets are broken by impact forces from a striker component, and three instances in which another three respective tablets remained unbroken despite impact forces from the striker component. In some implementations, such a determination may involve detecting whether the force profile has a time period during which force values remain substantially flat as a function of time, and form a plateau shape having a duration which exceeds a predefined threshold. Such a shape of the force profile may indicate that a tablet associated with the force profile has not been broken. If, on the other hand, the force profile has a shape in which force values increase toward a peak, and then decrease without forming a plateau, such a force profile may indicate that a tablet associated with the force profile has been broken by the force imparted to it during the impact strike test.

In some cases, if the impact strike test is performed on a single tablet or solid dosage form for a particular tablet type, the step 6004 may involve measuring a peak impact force value that indicates a peak amount of force imparted to the tablet by the striker component, or more specifically how much impact force is involved in breaking the single tablet. In some cases, if the impact strike test is performed on a set of tablets for a particular tablet type, the step 6004 may involve measuring a peak impact force value which indicates an average of peak amounts of impact force imparted to the set of tablets, or more specifically an average of how much impact force is involved in breaking the set of tablets.

In some instances, the step 6004 may be performed by or with assistance of a sensor data acquisition system, e.g., sensor data acquisition system 1140, 2140. For example, a strain gauge force sensor 2141 embedded within a striker component 2120 may measure, for each of the first plurality of tablets or first plurality of sets of tablets, a respective peak impact force. In this example, the step 6004 may further involve personnel at a manufacturing or research/development facility and/or a computing system, e.g., computing system 1200, receiving the sensor data generated by the sensor 2141. The sensor data may be received directly from the sensor 2141, or via a communication circuit, e.g., the communication circuit 2143.

Figure 8A:
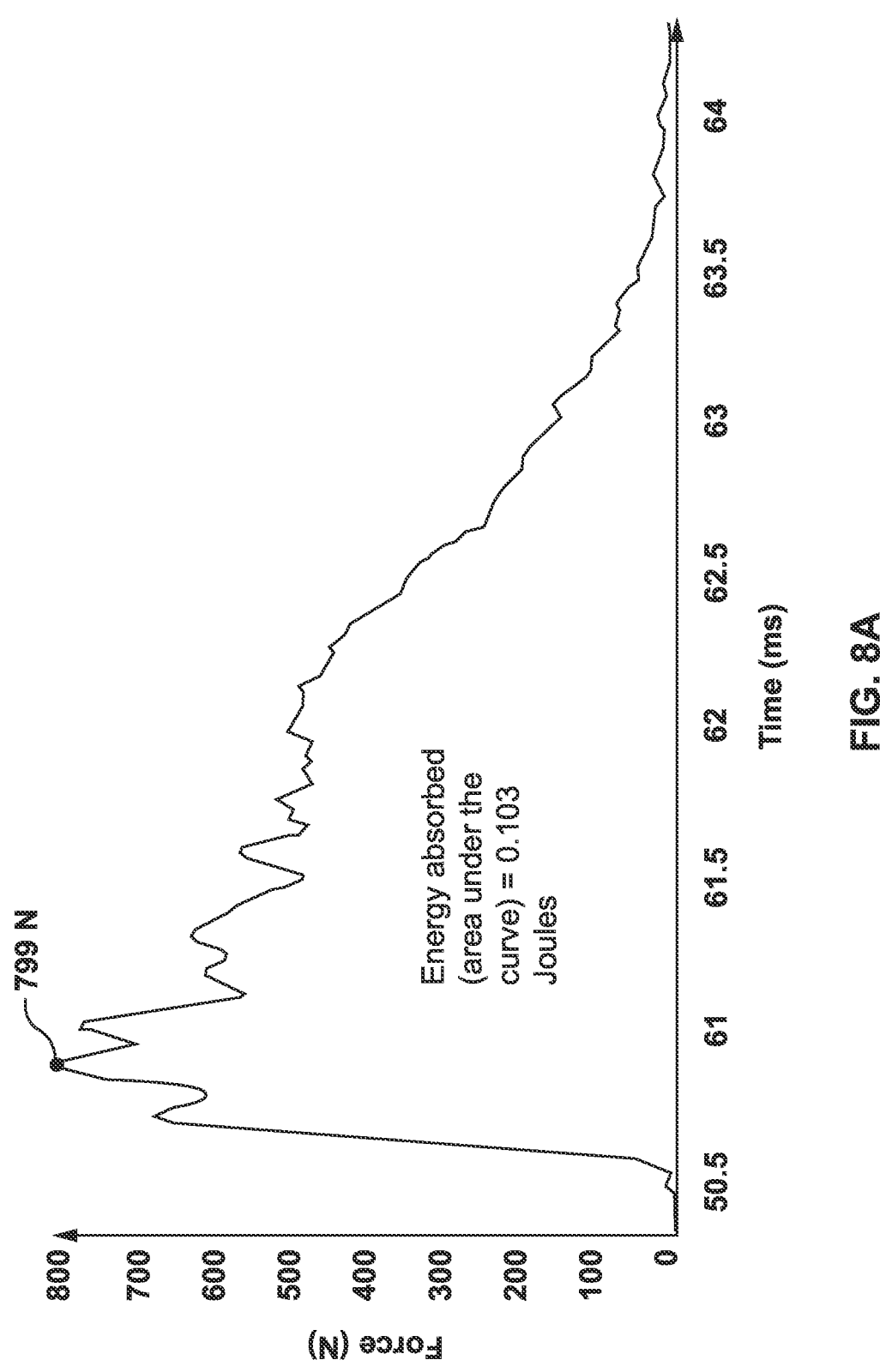
FIGS. 8A and 8B depict a force being imparted by a striker component to a tablet during an impact strike test according to embodiments herein.
Figure 8B:
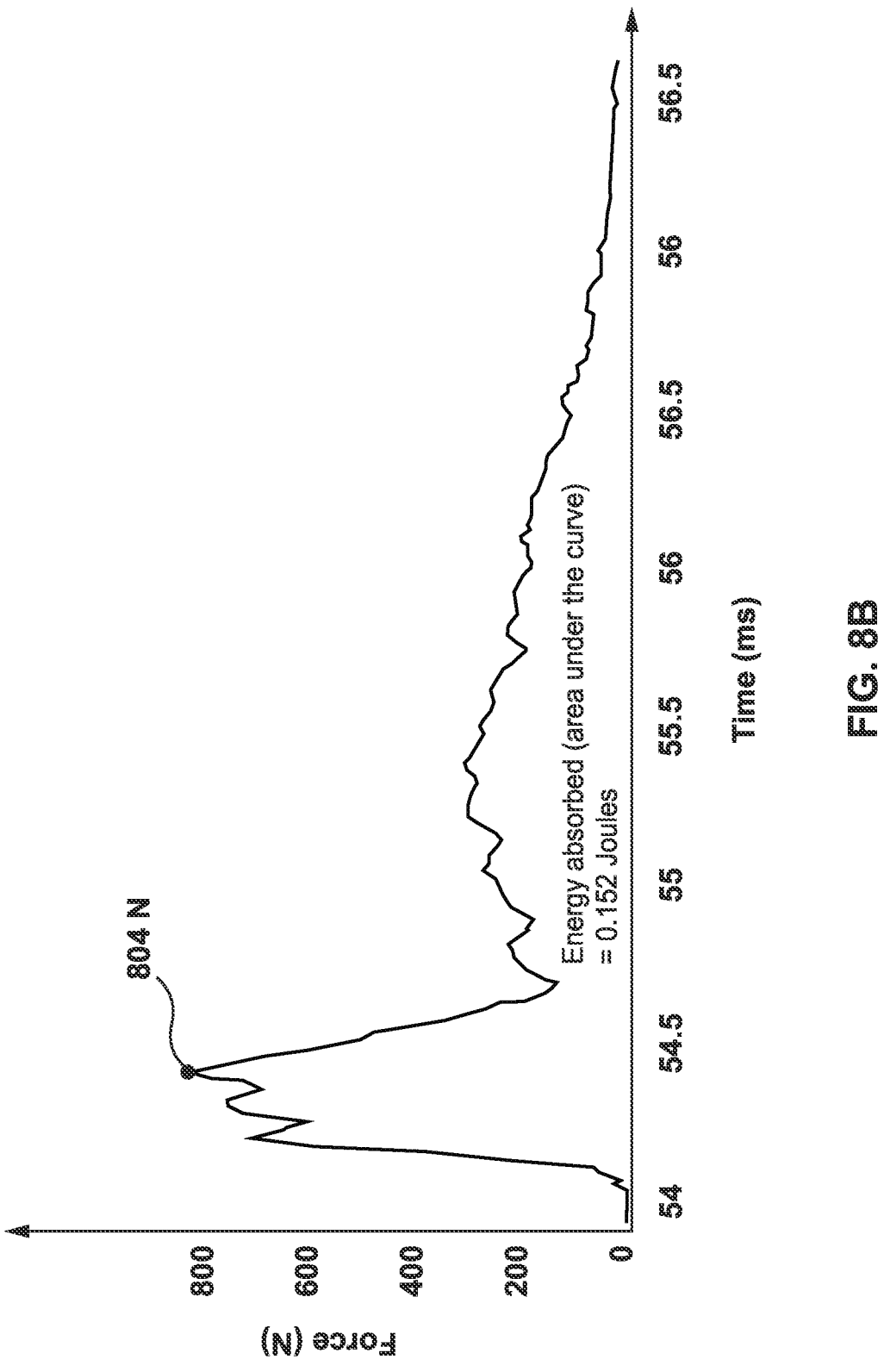
Figure 8E:
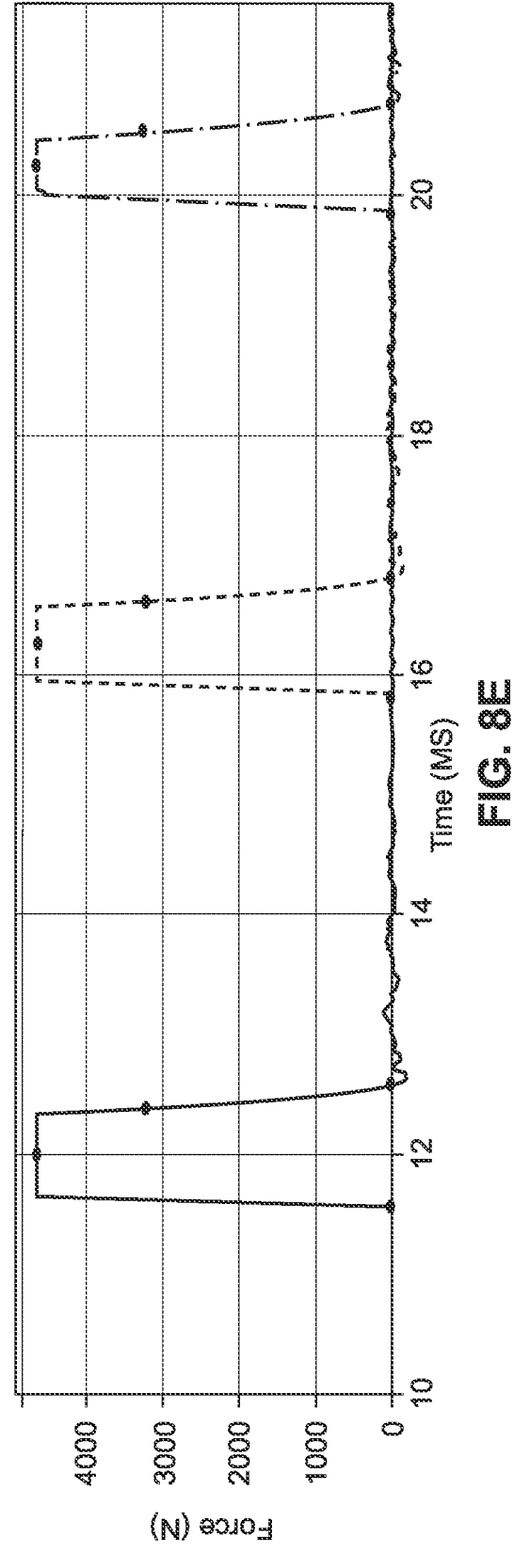
FIG. 8E depicts force profiles for situations in which a tablet is broken during an impact strike test, and force profiles for situations in which a tablet is not broken according to embodiments herein.

FIGS. 8A and 8B illustrate a graph of data which may illustrate how much force is being imparted by a striker component 1120, 2120, 3120 to a tablet, e.g., a tablet 3300, at an impact site 2132, 3132 at different points in time, and/or how much force is being absorbed by a tablet from the striker component. The graph may represent or may be based on, e.g., sensor data collected at a step 6004. For instance, FIG. 8A may represent data that is collected or generated when an impact strike test is breaking a first tablet, while FIG. 8B may represent data that is collected or generated when the impact strike test is breaking a second tablet. In one example, as the striker component 1120, 2120, 3120 collides with, impacts, or otherwise strikes the tablet, e.g., tablet 3300, the striker component 1120, 2120, 3120 may suddenly decelerate. The sensor 2141 or some other sensor may measure how much the striker component 1120, 2120, 3120 is accelerating or decelerating at different points in time. Such a measurement may be used to approximate or otherwise indicate how much force (also referred to as impact force) the striker component 1120, 2120, 3120 is imparting to the tablet 3300 as a function of time. More specifically, the sensor data may indicate a peak impact force value that is imparted by the striker component 1120, 2120, 3120 to the tablet 3300, and/or an energy absorbed by the tablet from the striker component 1120, 2120, 3120. In some instances, a step 6004 may involve a computing system 1200 calculating force values, such as those forming the graphs of FIGS. 8A and 8B, based on sensor data generated by the sensor data acquisition system, e.g., sensor data acquisition system 2140. As stated above, the impact strike test may be performed in a manner that maximizes a likelihood of breaking each tablet of the first plurality of tablets. As further stated above, a computing system or other device may determine, based on sensor data collected by performing an impact strike test on a tablet, whether the tablet was in fact broken. Thus, a step 6004 may involve measuring peak impact force values associated with breaking the first plurality of tablets. For example, if a step 6004 is based on the data represented in FIGS. 8A and 8B, the step 6004 may involve determining a peak impact force value of 799 N associated with breaking a first tablet, and a peak impact force value of 804 N associated with breaking a second tablet. FIGS. 8C and 8D illustrate examples of average peak impact force values determined from a set of ten tablets for various formulations and various tablet shapes.

Figure 9A:
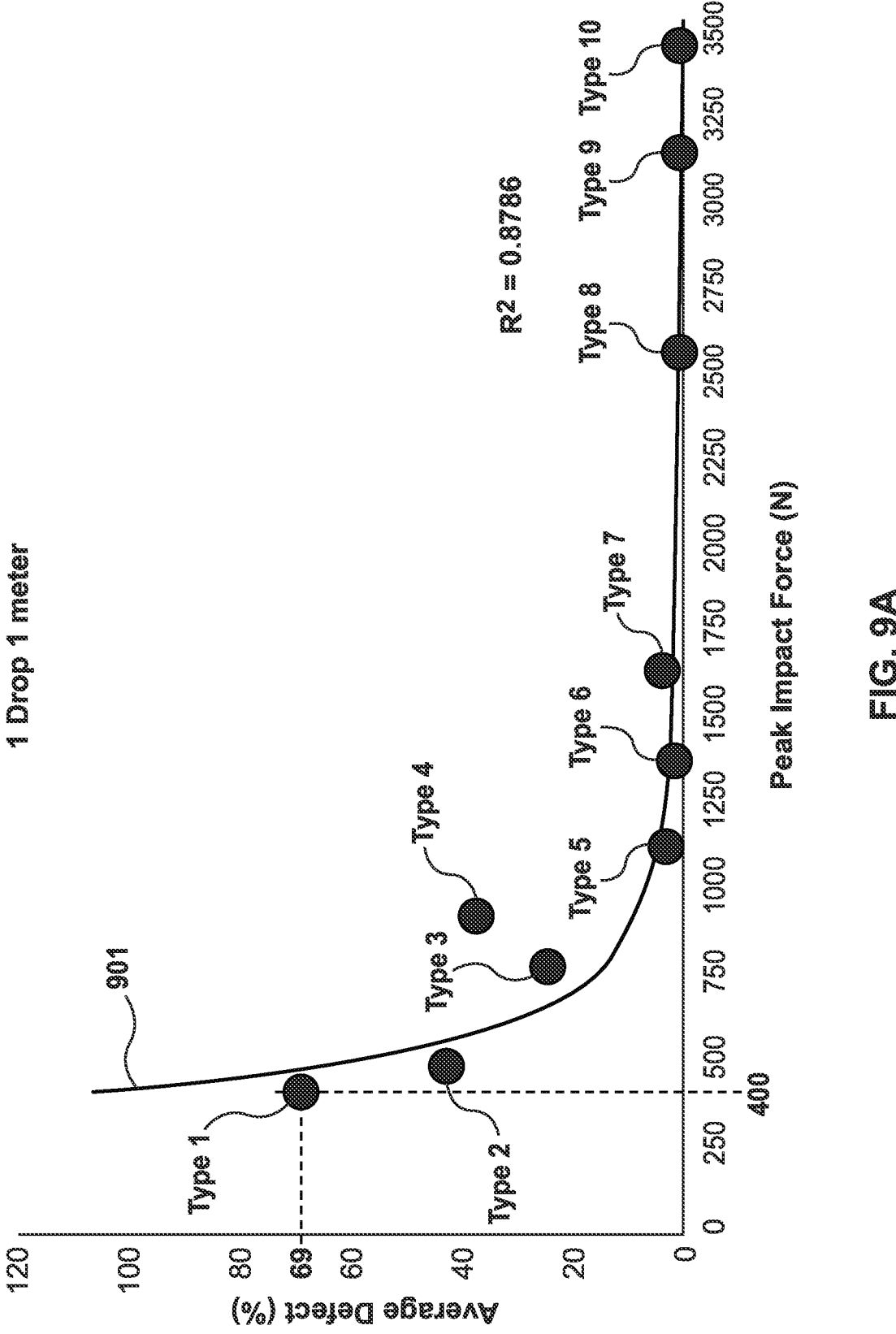
FIGS. 9A-9F illustrate various values of peak impact force and physical defect rate associated with various tablet types according to embodiments herein.
Figure 9B:
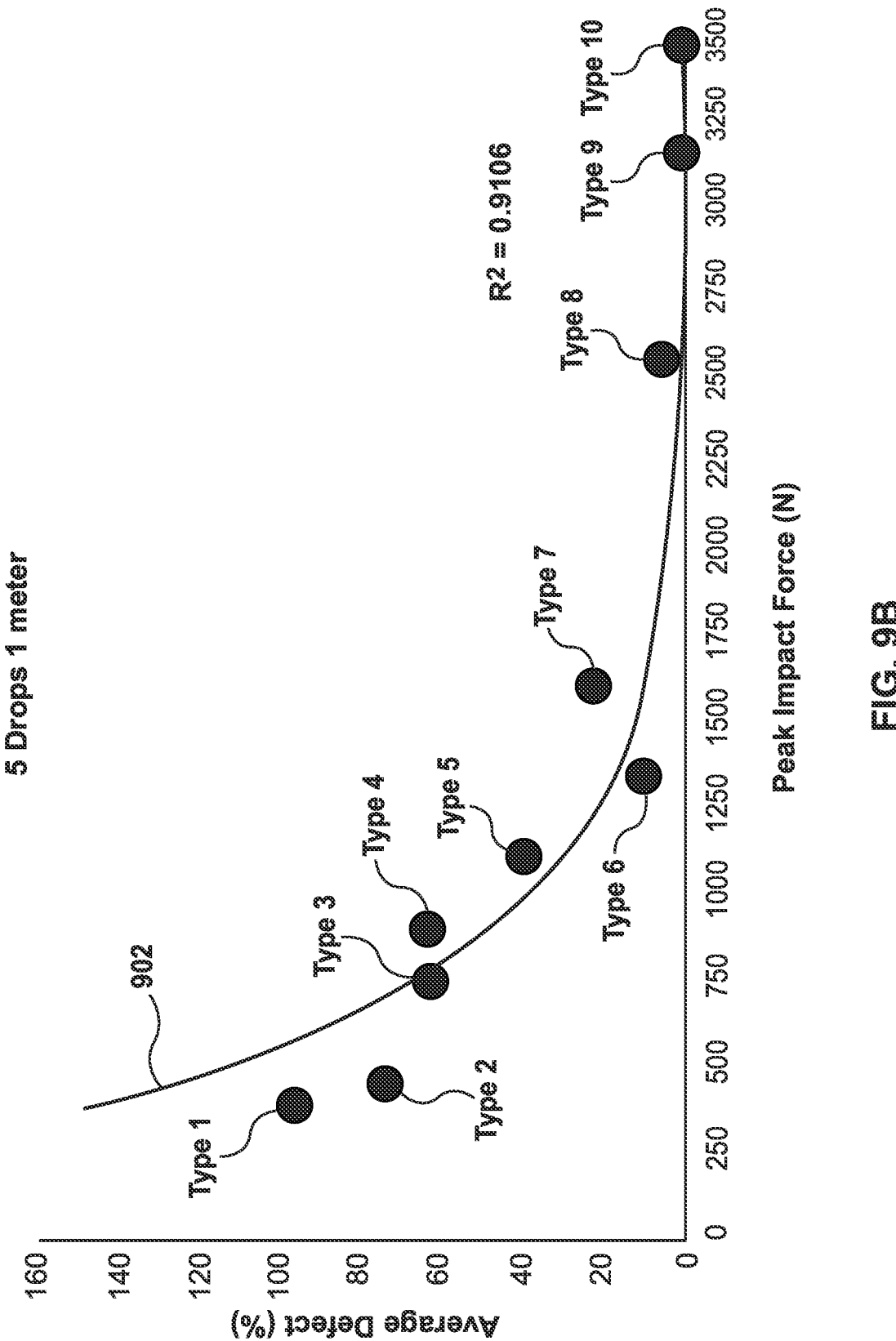
Figure 9C:
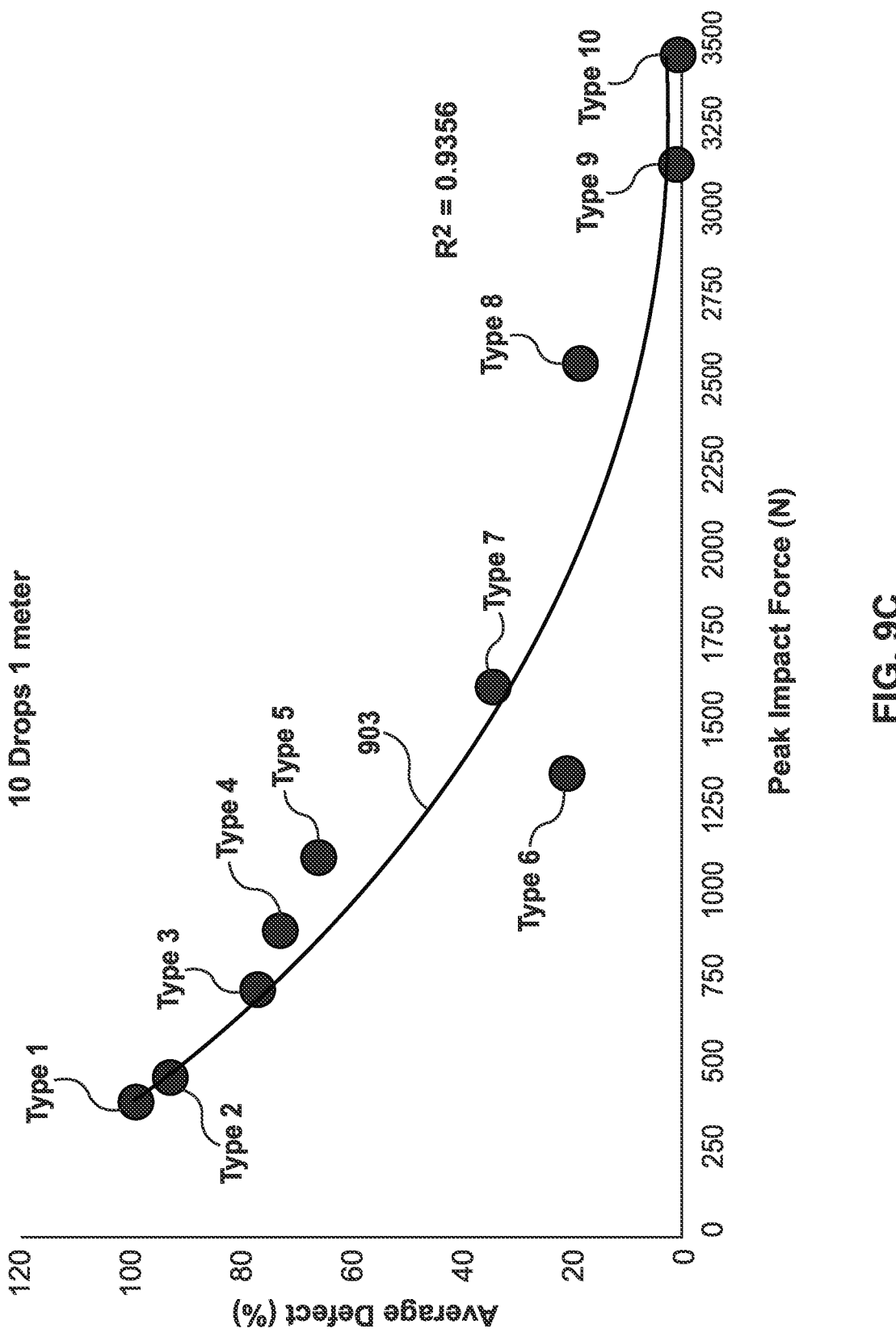

FIGS. 9A-9F illustrate peak impact force values which may be measured as a result of a step 6006 of the method 6000. More specifically, the figures depict graphs in which the X-axis represents average peak impact force values associated with breaking tablets of different tablet types. For example, the graph in FIG. 9A represents data which indicates that a set of tablets associated with a Tablet Type 1 has an average peak impact force value of about 400 N. This data point may have been determined, e.g., by performing the impact strike test in a step 6002 on a set of, e.g., five tablets belonging to or otherwise associated with the Tablet Type 1, and determining an average of the peak impact force values imparted to or absorbed by the five tablets. As stated above, the peak impact force values may indicate a maximum force the five tablets withstood before breaking. In an embodiment, FIGS. 9A-9F may each indicate average peak impact force values associated with Tablet Types 1 through 10, respectively, but may be associated with different circumstances under which a tablet drop test is performed, as discussed below in more detail.

Figures 10A, 10B:
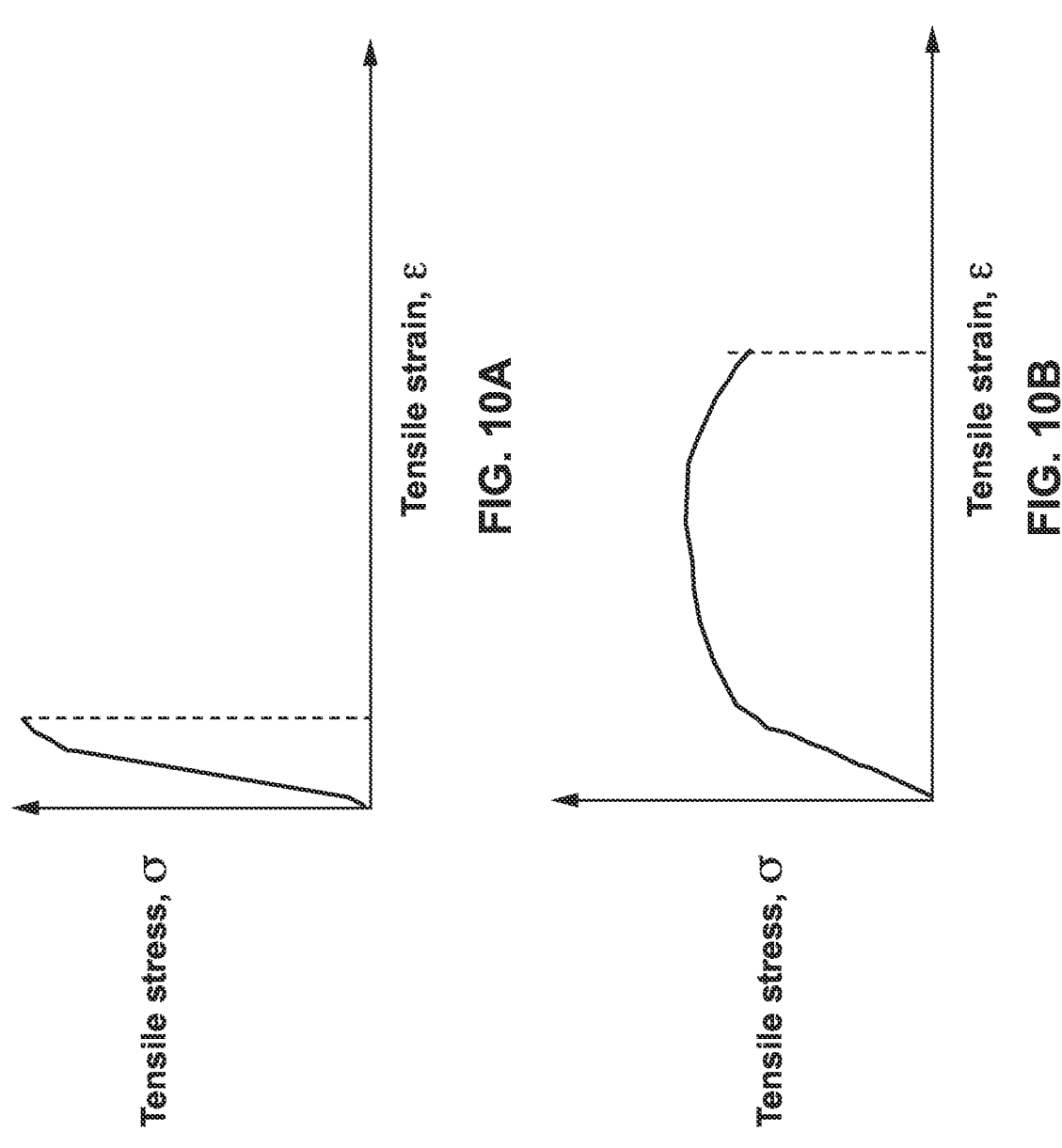
FIGS. 10A and 10B illustrate stress-strain curves which may be used to measure toughness associated with various tablet types according to an embodiment herein.

In some implementations, a step 6004 may involve measuring or otherwise determining an amount of energy absorbed by a tablet or solid dosage form during an impact strike test, instead of or in addition to measuring peak impact force values. As depicted in FIGS. 8A and 8B, the amount of energy absorbed may be determined by integrating the force values in the figures, so as to determine an area under the curves in FIGS. 8A and 8B. For example, FIGS. 8C and 8D illustrate data which indicates both a peak impact force imparted to or absorbed by a tablet, and an amount of energy imparted to or absorbed by the tablet. In some implementations, a step 6004 may involve measuring a toughness parameter for a first plurality of tablets or first plurality of sets of tablets, instead of or in addition to measuring peak impact force values. In some instances, the toughness parameter for a tablet may be measured based on calculating an area under a stress-strain curve of the tablet, such as the stress-strain curves illustrated in FIGS. 10A and 10B.

Returning to FIG. 6, the method 6000 may in an embodiment include a step 6006, which includes performing a tablet or solid dosage form drop test on a second plurality of sets of tablets or solid dosage forms. The second plurality of sets of tablets may be also associated with a plurality of tablet types discussed above with respect to the step 6002. In other words, each set of the second plurality of sets of tablets may be associated with a respective tablet type of the plurality of tablet types. For example, the second plurality of tablets may include a set of tablets, e.g., one hundred tablets, that belong to a first tablet type, e.g., a Tablet Type 1, include a set of tablets, e.g., one hundred tablets that belong to a second tablet type, e.g., Tablet Type 2, etc.

In an embodiment, a tablet drop test may include dropping a second plurality of sets of tablets on a solid or otherwise rigid surface, and inspecting what percentage of the tablets break, or experience a physical defect as a result of being dropped. For instance, the tablet drop test may be performed on a set of tablets associated with a particular tablet type by holding the set of multiple tablets, e.g., one hundred tablets above a solid surface, and releasing the set of tablets to permit them to drop onto the solid surface. The holding and dropping of the tablets may be performed manually, or may be performed automatically, and may be done one tablet at a time, or may be done for some or all of the set of tablets at the same time.

In an embodiment, a tablet drop test may simulate different circumstances in which tablets are dropped. The circumstances may refer to, e.g., drop height, drop count, or a combination thereof. In such an embodiment, different circumstances may refer to different drop heights, different drop counts, or different combinations thereof. As an example, the different circumstances may involve a first combination in which tablets are dropped only once, from a height of one meter; a second circumstance in which tablets are dropped five times, from a height of one meter; a third circumstance in which tablets are dropped ten times, from a height of one meter; a fourth circumstance in which tablets are dropped only one, from a height of two meters; a fifth circumstance in which tablets are dropped five times, from a height of two meters, and a sixth circumstance in which tablets are dropped ten times, from a height of two meters. These circumstances may be used to generate data illustrated in, e.g., FIGS. 9A-9F. For instance, the tablet drop test may be performed on a set of, e.g., six hundred tablets associated with a particular tablet type, e.g., Tablet Type 1. In this example, the tablet drop test may involve dropping a different respective subset of tablets for each of the circumstances discussed above. Thus, the tablet drop test may in this example may involve dropping a first subset of one hundred tablets onto a solid surface using the first circumstance discussed above: dropping a second subset of one hundred tablets onto the solid surface using the second circumstance discussed above: dropping a third subset of one hundred tablets onto the solid surface using the third circumstance discussed above: dropping a fourth subset of one hundred tablets onto the solid surface using the fourth circumstance discussed above: dropping a fifth subset of one hundred tablets onto the solid surface using the fifth circumstance discussed above; and dropping a sixth subset of one hundred tablets onto the solid surface using the sixth circumstance discussed above. In the above example, the tablet drop test may involve dropping other sets of tablets, which may be associated with other tablet types, e.g., Tablet Type 2, Tablet Type 3, etc.

Returning to FIG. 6, the method 6000 may in an embodiment include a step 6008, which may include measuring, based on the tablet drop test, a plurality of physical defect rates associated with the plurality of tablet types. For instance, FIG. 9A illustrates data points which represent a plurality of physical defect rates associated with Tablet Types 1 through 10. As an example, the data points indicate that a Tablet Type 1 has a physical defect rate of 69%. FIGS. 9B-9F may each indicate another respective plurality of physical defect rates associated with the plurality of tablet types, and associated with other circumstances in which the tablet drop test is performed.

In an embodiment, measuring a physical defect rate for a tablet type may involve counting, automatically or manually, how many tablets in a set or subset of tablets associated with the tablet type were broken or otherwise experienced a physical defect as a result of being dropped, and calculating what rate or percentage of the set of tablets experienced the physical defect. As an example, if the tablet drop test involved dropping the first subset of, e.g., 100 tablets associated with Tablet Type 1 only once from a height of 1 meter, as discussed above, a step 6008 may involve counting how many tablets of the subset were broken or experienced physical defect as a result of being dropped. For instance, if 69 of the tablets is counted as experiencing a physical defect, then a step 6008 may involve determining that there is a physical defect percentage (also referred to as physical defect rate) of 69% associated Tablet Type 1 when tablets associated with Tablet Type 1 are dropped only once from a height of 1 meter.

In an embodiment, a plurality of physical defect rates as discussed above may be a first plurality of physical defect rates, and a step 6008 may involve measuring or determining a second plurality of physical defect rates, a third plurality of physical defect rates, etc. Each plurality of physical defect rates may be associated with a particular circumstance, such as a combination of drop height and drop count, in which tablets are dropped. As an example. FIG. 9A may represent data that indicates a first plurality of physical defect rates associated with Tablet Types 1 through 10, respectively, when tablets in the tablet drop test are dropped only once, from a height of 1 meter, while FIG. 9B may represent data that indicates a second plurality of physical defect rates associated with Tablet Types 1 through 10, respectively, when tablets in the tablet drop test are dropped a total of five times, from a height of one meter. While the above embodiment discusses obtaining physical defect rates from performing a drop test, the physical defect rates may be obtained using any other test.

Returning to FIG. 6, the method 6000 may in an embodiment include a step 6010, which includes determining, based on the plurality of peak impact force values and the plurality of physical defect rates, a model that describes a relationship between peak impact force values and physical defect rates. In an embodiment, a model may include or may be described by an equation or function which describes the relationship between peak impact force values and physical defect rates. For example. FIG. 9A illustrates a curve 901 that represents an equation or function between peak impact force values and physical defect rates. The curve 901 or its corresponding equation may be determined by performing a curve fitting operation. Such an operation may involve determining a curve that best fits the data points in FIG. 9A. As discussed above, each of the data points in FIG. 9A may indicate a respective average peak impact force value associated with one of Tablet Types 1 through 10, and a respective physical defect rate associated with the tablet type. The average peak impact force value may have been determined via the impact strike test, while the physical defect rate may have been determined via the tablet drop test.

In an embodiment, a model may be determined based on multiple curves or equations, each of which may be associated with a specific circumstance under which the tablet drop test is performed, such as a specific combination of drop height and drop count. For example, the model may include or may be described by curves 901, 902, 903, 904, 905, and 906 of FIGS. 9A-9F, respectively, or by the equations represented by the curves. The curves 901-906 may be associated with different circumstances in which the tablet drop test is performed.

In an embodiment, a method 6000 may include a step of determining, based on the model of a step 6010, a predicted physical defect rate for another circumstance in which tablets are dropped, and/or for another tablet type. For instance, the prediction may be performed for another tablet type such as Tablet Type 11, and/or for another combination of drop count and drop height, such as 5 drops from a height of 1.5 meters, or 4 drops from a height of 2 meters. In some cases, such a step may be performed by personnel at a manufacturing facility and/or by the computing system 1200.

Figure 11B:
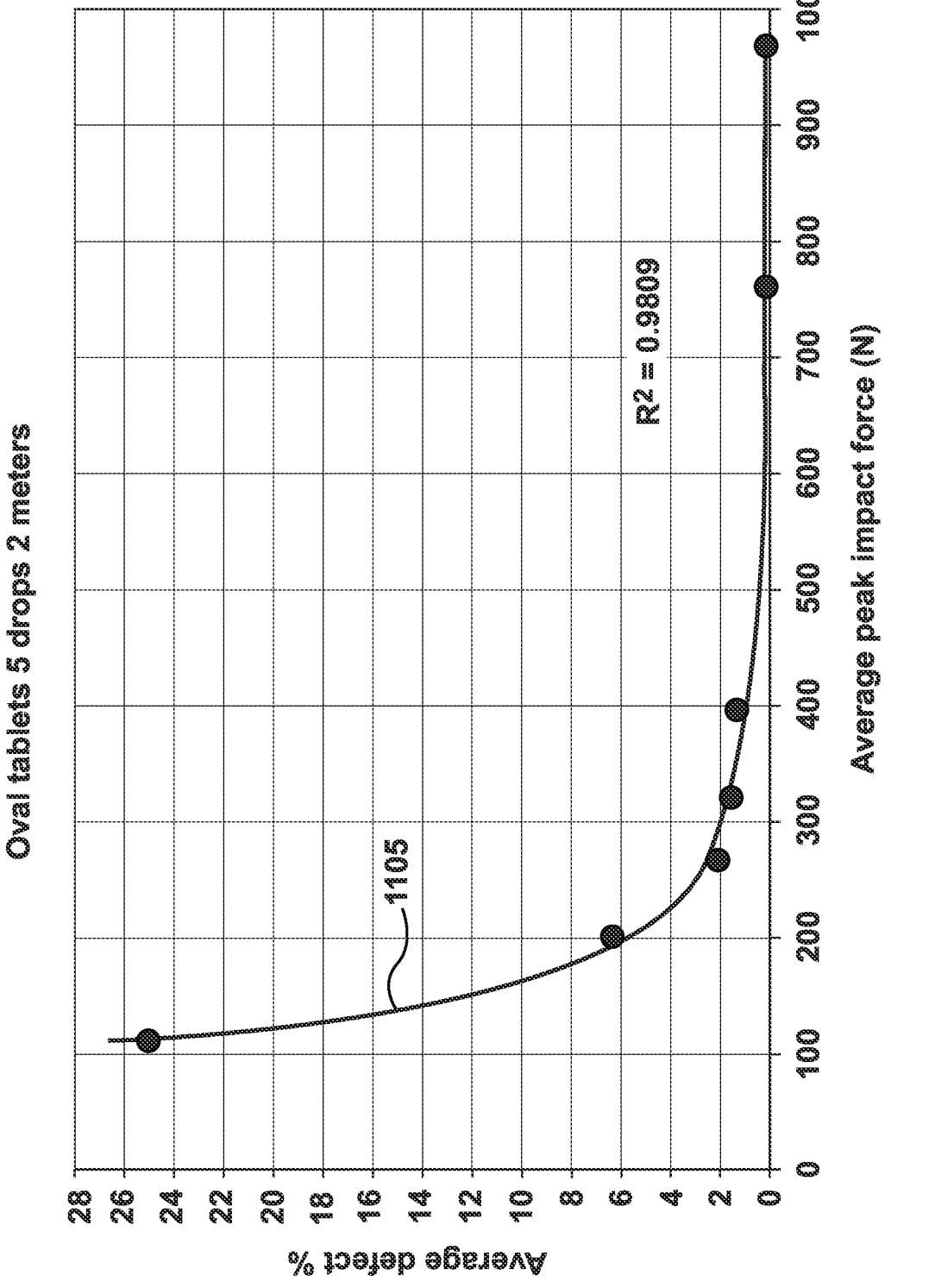

In some cases, determining such a prediction may involve performing an impact strike test on an additional tablet or set of tablets to determine a peak impact force value, and using the peak impact force value to determine the predicted physical defect rate, or more generally to assess a physical strength or robustness of the additional tablet or set of tablets. For instance, the step may involve performing the impact strike test on an additional tablet or an additional set of tablets associated with, e.g., Tablet Type 11, and measuring a peak impact force value which indicates a peak amount of impact force that the additional tablet or additional set of tablets received from the striker component during the impact strike test, or more specifically indicates a maximum amount of force withstood by the additional tablet before breaking during the impact strike test. In this example, the step may determine a predicted physical defect rate for Tablet Type 11 based on the model discussed above, and based on the peak impact force value. In some cases, the peak impact force value may be an average peak impact force value involved in breaking the additional set of tablets. FIG. 11A depicts predicted physical defect rates for various tablet types, wherein the predictions may be based on average peak impact force values derived from performing the impact strike test on tablets belonging to the tablet types. In some cases, the predicted physical defect rate may be for a specific circumstance in which tablets are dropped, such as a circumstance in which tablets are dropped five times, from a height of two meters. In such instances, the prediction may involve using a curve associated with such a circumstance, such as curve 905 of FIG. 9E or curve 1105 of FIG. 11B. For example, the predictions in FIG. 11A may involve determining a value of physical defect rate that corresponds to, e.g., 508 N, 234 N, and 128 N on the curve 1105.

Figure 9D:
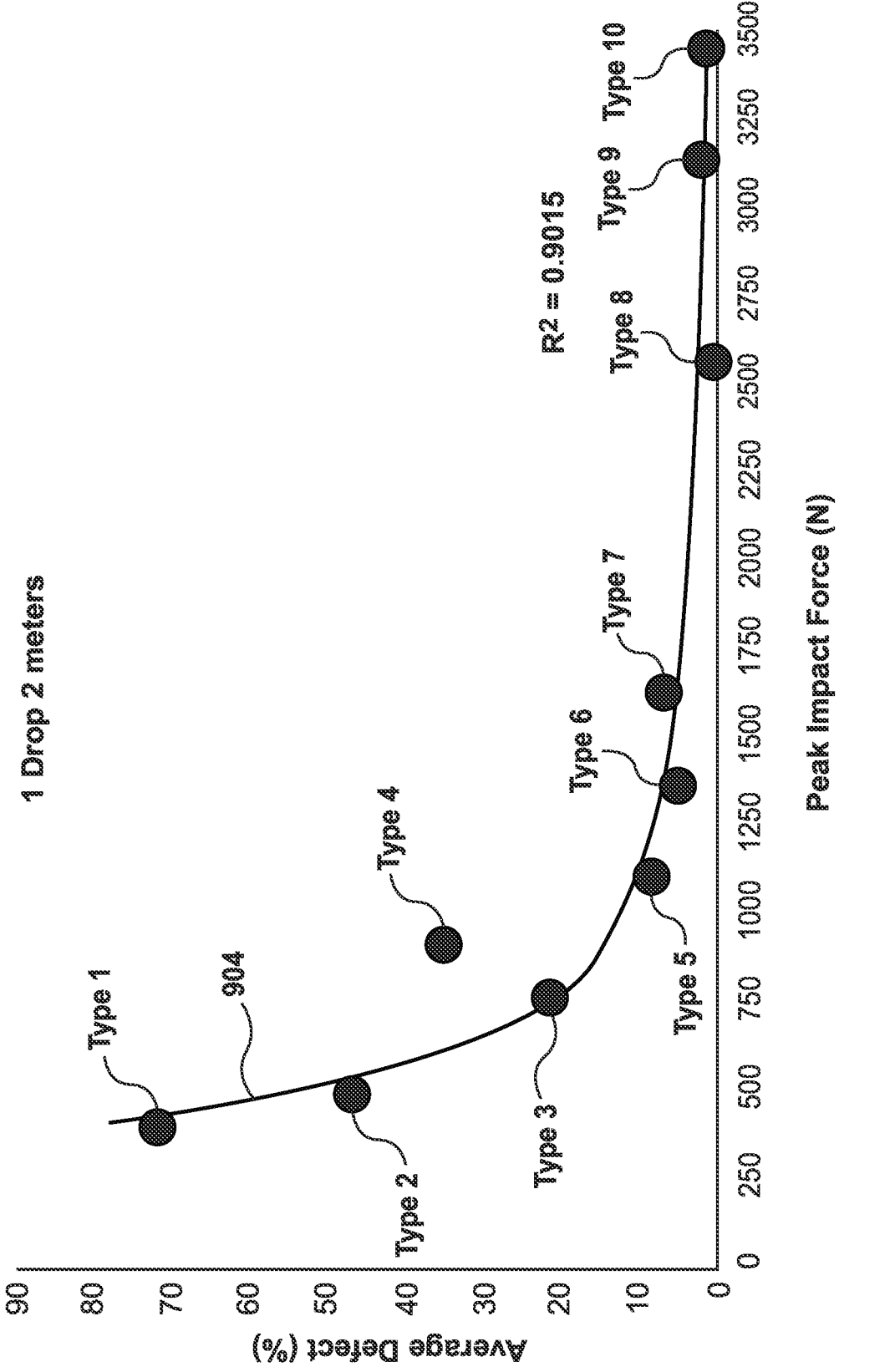
Figure 9E:
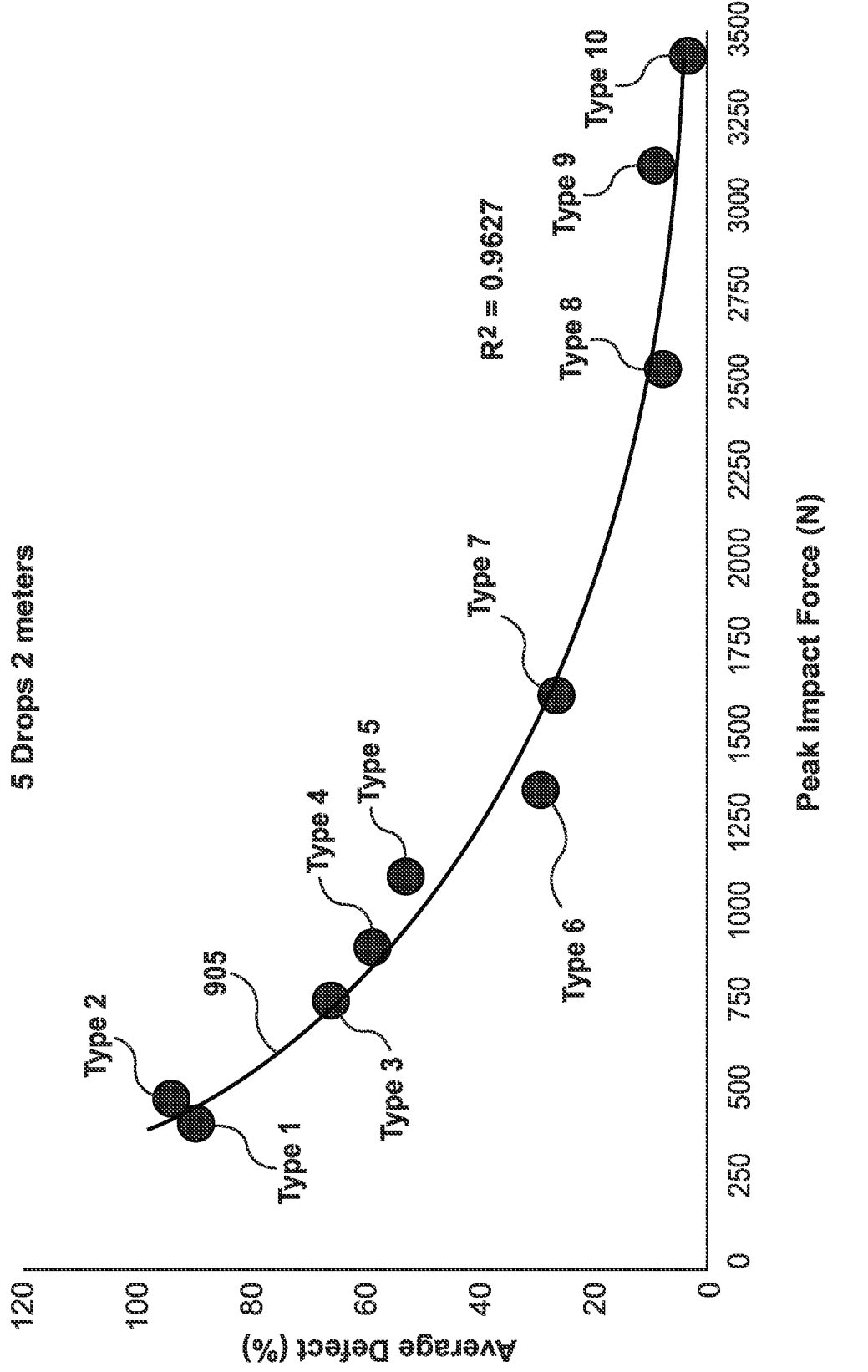
Figure 9F:
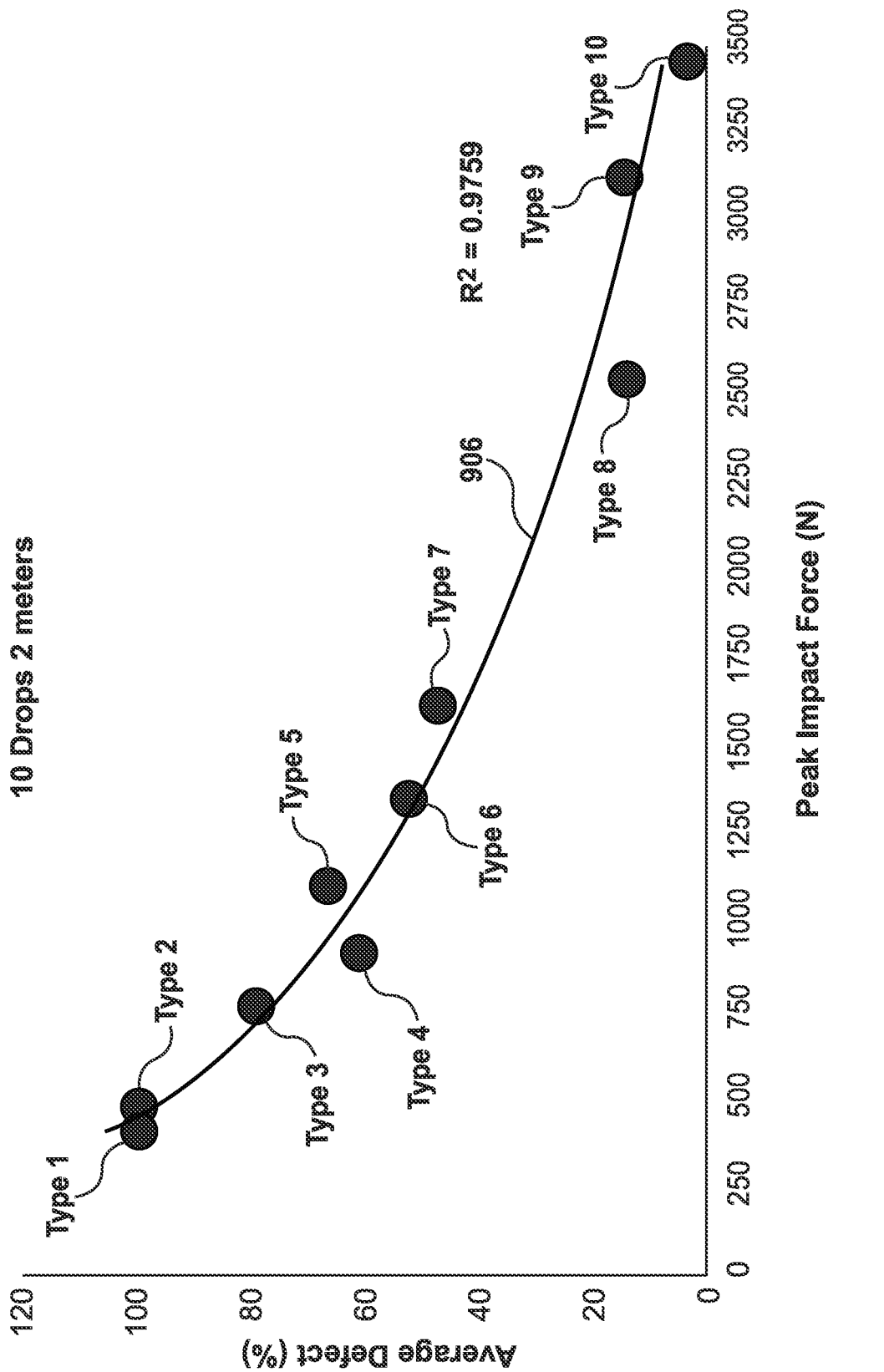

As another example, the above step 6010 may involve determining a predicted physical defect rate for, e.g., an additional circumstance different than the circumstances in which tablets are dropped during the tablet drop test in a step 6006. For instance, the step may involve determining a predicted physical defect rate for Tablet Type 1. Tablet Type 2. Tablet Type 11. Tablet Type 12, or some other tablet type, for a circumstance in which tablets of the tablet type are dropped four times, from a height of 2 meters. Such a circumstance may be different than those illustrated in FIGS. 9A-9F, which represent circumstances in which the tablet drop test is performed for a step 6006. In such an example, the step may involve determining one or more intermediate physical defect rates, which may be physical defect rates associated with circumstances that are directly represented by the model of a step 6010 and which are closest to the additional circumstance discussed above. For example, if the additional circumstance refers to tablets being dropped four times from a height of two meters, the intermediate physical defect rates may include a first physical defect rate associated with a circumstance in which tablets are dropped once, from a height of two meters, and a second physical defect rate associated with a circumstance in which tablets are dropped five times, from a height of two meters, as illustrated in FIGS. 9D and 9E. In this example, the prediction step discussed above may extrapolate the physical defect rate for the additional circumstance (of four drops from a height of two meters) based on the intermediate physical defect rates discussed above.

Figure 12B:
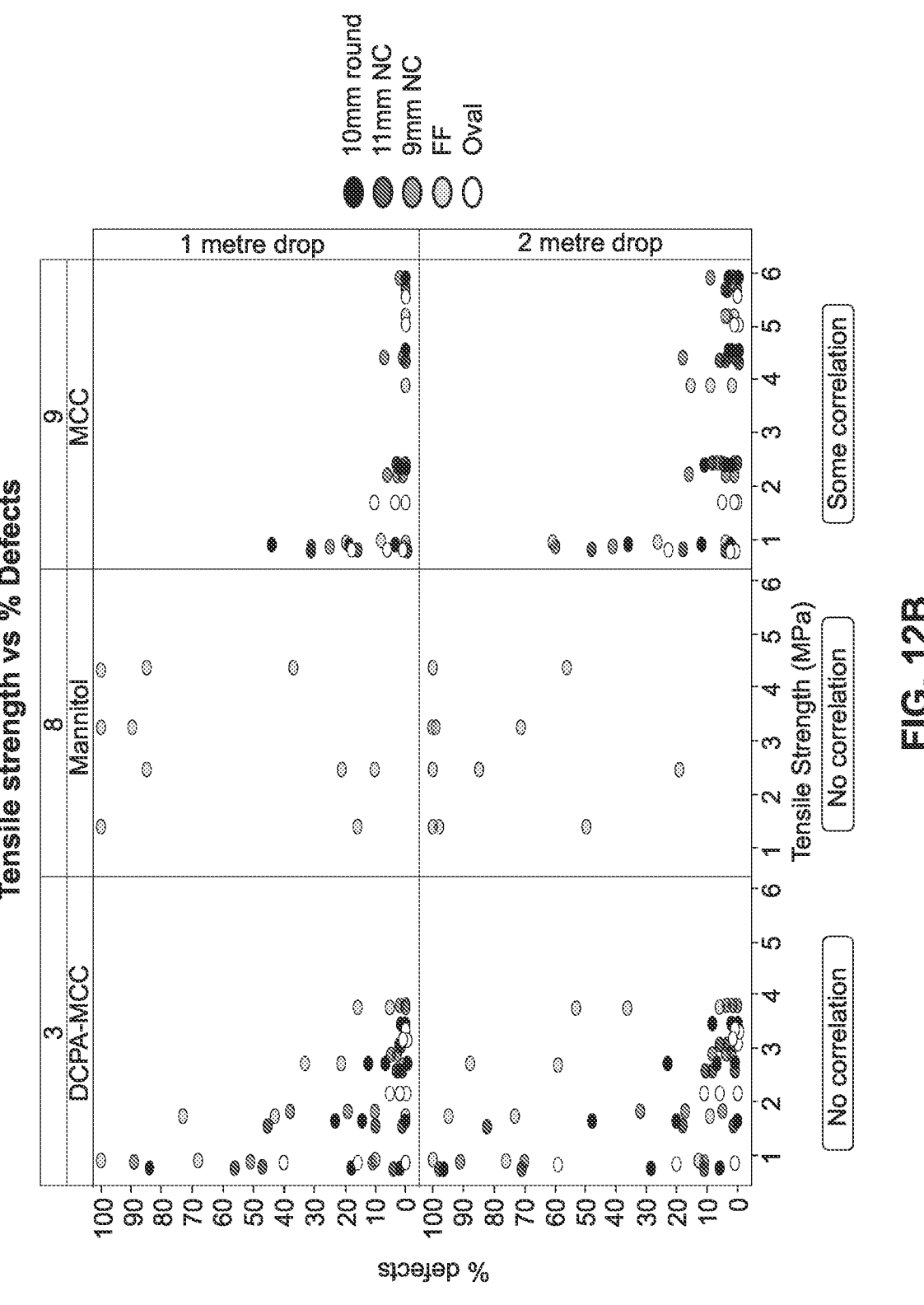
FIG. 12B illustrates a relative lack of correlation between tensile strength and physical defect rates of tablets according to an embodiment herein.
Figure 12C:
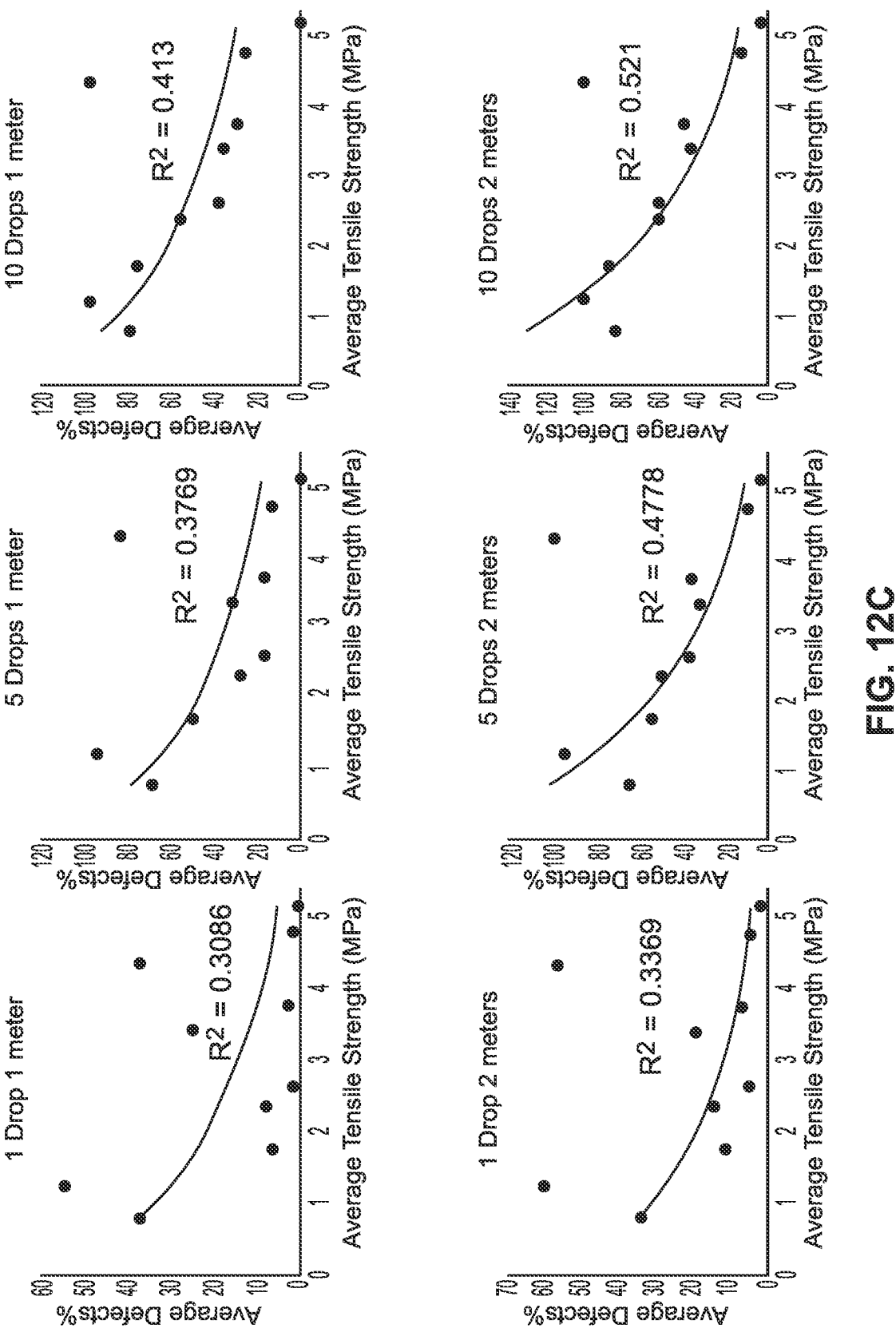
FIG. 12C illustrates error values associated with curves that attempt to relate tensile strength to physical defect rates according to an embodiment herein.
Figure 15:
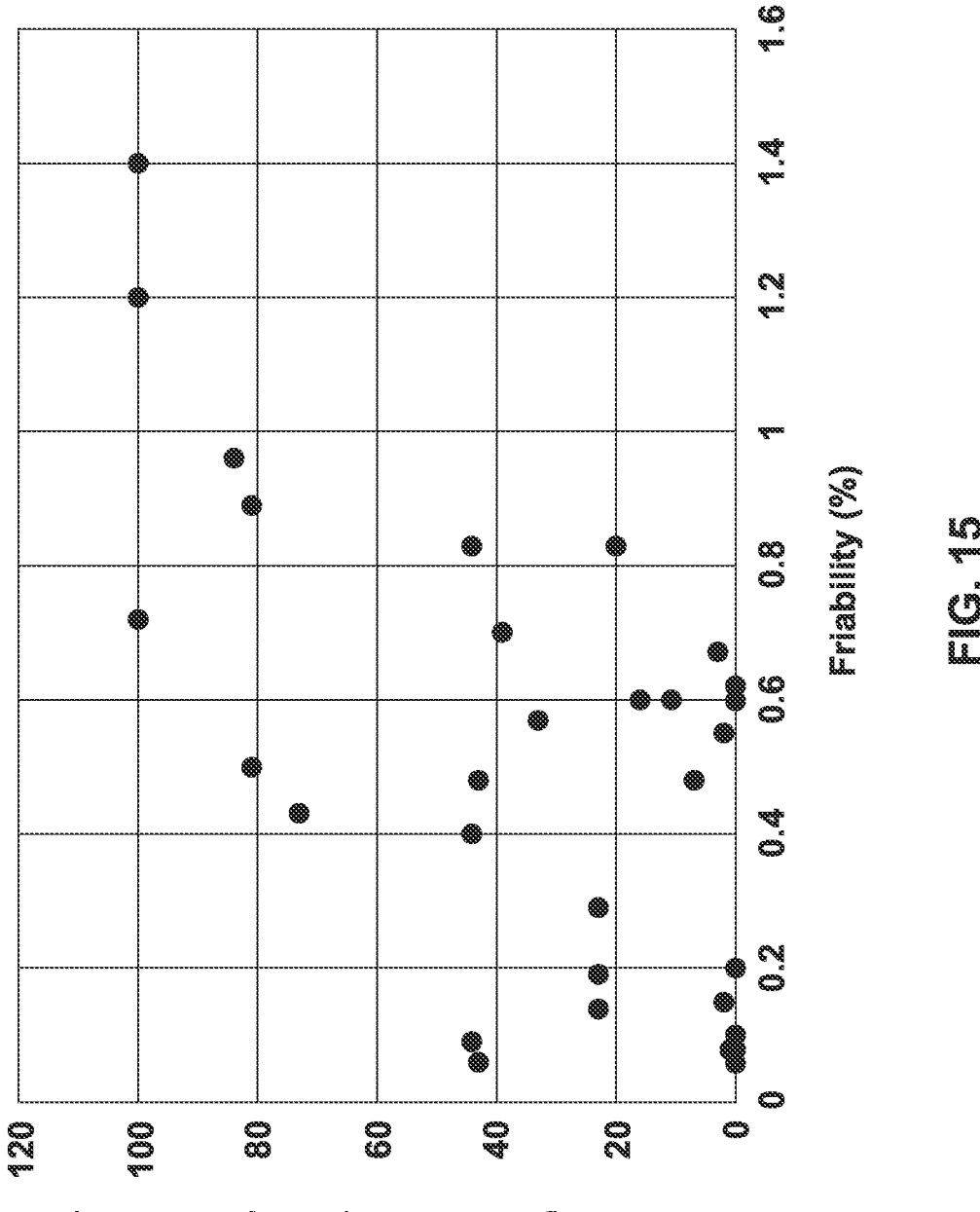
FIG. 15 illustrates a relative lack of correlation between friability values and physical defect rates of tablets according to an embodiment herein.

As discussed above, one aspect of the present disclosure relates to using a measurement of peak impact force involved in breaking a tablet to assess the physical strength or robustness of a tablet or batch of tablets, or more specifically to predict a physical defect rate for a batch of tablets (or some other parameter which indicates a likelihood that the tablets will experience physical defects). More particularly, the peak impact force value may provide a strong indicator or a strong predictor regarding a physical defect rate that will likely be experienced by a batch of tablets. For instance, FIG. 12A depicts data which compares p-values and $R^2$ values associated with peak impact force and p-values and $R^2$ values associated with tensile strength. The p-value for a parameter may indicate how useful the parameter is for explaining variations in physical defect rates, or more specifically may indicate whether the parameter supports a hypothesis that physical defect rates are affected by the parameter. As illustrated in FIG. 12A, the peak impact force values may have low p-values. A low p-value, e.g., a p-value less than 0.05, may indicate a high likelihood that a null hypothesis is untrue, such as a null hypothesis in which physical defect rates are not affected by variations in peak impact force values. In other words, a low p-value for peak impact force values may indicate or may be at least consistent with a hypothesis that physical defect rates are influenced by or correlated with variations in peak impact force values. As further depicted in FIG. 12A, the p-values for tensile strength may be considerably higher than p-values for peak impact force values. A high p-value for a parameter, e.g., a p-value greater than 0.05, may indicate that the parameter has only limited or no influence on physical defect rates. FIG. 12B provides additional data which illustrate a lack of correlation between tensile strength and physical defect rates among tablets. FIG. 12A further indicates that there is a higher $R^2$ value for fitted curves or equations which describe a relationship between peak impact force value and physical defect rates, than curves or equations which describe a relationship between tensile strength and physical defect rates. A higher $R^2$ value may indicate that a fitted curve has a lower level of error when compared with data points used to perform the curve fitting. FIG. 12C illustrates the $R^2$ values for fitted curves which are used in an attempt to relate tensile strength and physical defect rates. As FIG. 12C illustrates, the $R^2$ values for such curves are lower relative to the $R^2$ of curves like that in FIG. 11B, that relate peak impact force to physical defect rates. Thus, the data in FIGS. 11B, 12A and 12C indicate that, relative to other parameters such as tensile strength, peak impact force values have greater influence on physical defect rates, and a greater ability to accurately predict physical defect rates. More generally speaking, the peak impact force values may provide a greater ability than other parameters to assess the physical strength or robustness of tablets. FIG. 15 further demonstrates a limited ability of the other parameters, such as friability, to predict physical defect rates. The friability test is a qualitative test that provides a pass or fail criteria on tablet mechanical strength (e.g., pass: if no broken tablets and less than 1% weight loss, or fail: if any single tablet is broken and/or more than 1% weigh loss). Such a test only provides data at the test conditions (fixed drop height and fixed number of drops) and may have no ability or only a limited ability to be used to extrapolate beyond the test condition (more or less impact). Additionally, the friability test may lack ability to measure the energy absorbed by the broken tablets and therefore may fail to explain why a certain tablet gets broken or chipped.

Figure 13:
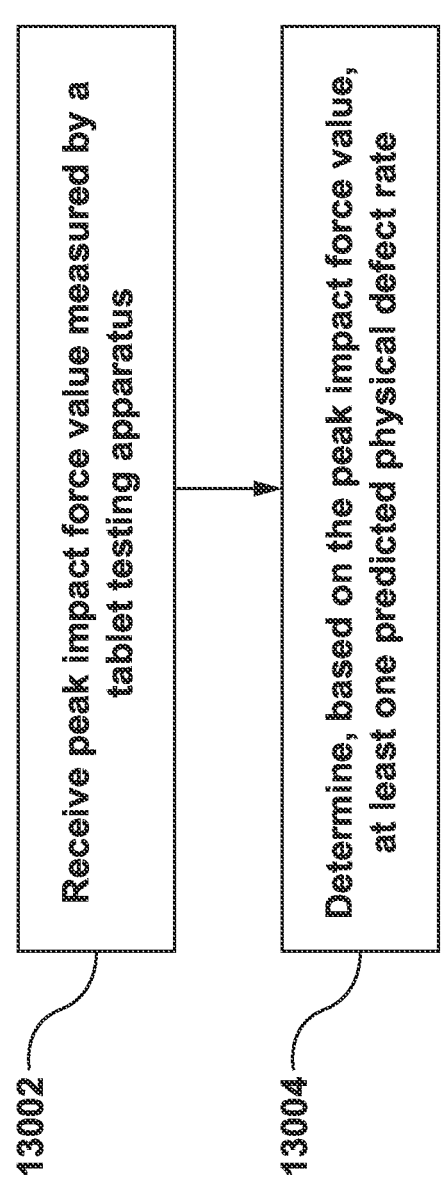
FIG. 13 is a flow diagram that depicts a method of predicting a physical defect rate based on peak impact force value according to an embodiment herein.

FIG. 13 illustrates a method 13000 which may be performed for using a peak impact force value to make a prediction regarding physical defect rates. As discussed below in more detail, the method 13000 may be performed based on a model, such as the model determined above using the impact strike test and the tablet drop test. In some implementations, the method 13000 may be performed by a computing system, such as the computing system 1200.

In an embodiment, a method 13000 may include a step 13002, in which a computing system 1200 receives a peak impact force value measured by a sensor of a tablet testing apparatus, e.g., 1100, 2100, 3100 during an impact strike test in which a striker component of the tablet testing apparatus strikes and breaks a tablet or a set of tablets. The tablet or set of tablets may belong to a particular tablet type, such as a Tablet Type 11. The peak impact force value may indicate a peak amount of impact force the tablet or set of tablets received from the striker component, e.g., 1120, 2120, 3120 during the impact strike test. If the impact strike test is performed on a set of tablets, the peak impact force value may be an average of the peak amounts of force respectively received by the set of tablets. In some instances, the peak impact force may be a maximum amount of force that the tablet withstood before breaking during the impact strike test, or an average of maximum amounts of force that the set of tablets respectively withstood before breaking.

In an embodiment, a method 13000 may include a step 13004, in which the computing system 1200 determines, based on the peak impact force value, at least one predicted physical defect rate for the tablet type, e.g., a Tablet Type 11, associated with the tablet or set of tablets used in the impact strike test. As discussed above, the tablet type is associated with a physical characteristic or set of physical characteristics for the tablet, such as a combination of formulation and physical shape or porosity. In this example, the at least one predicted physical defect rate may predict a likelihood of tablets belonging to the tablet type breaking when dropped on a solid surface.

Figure 14:
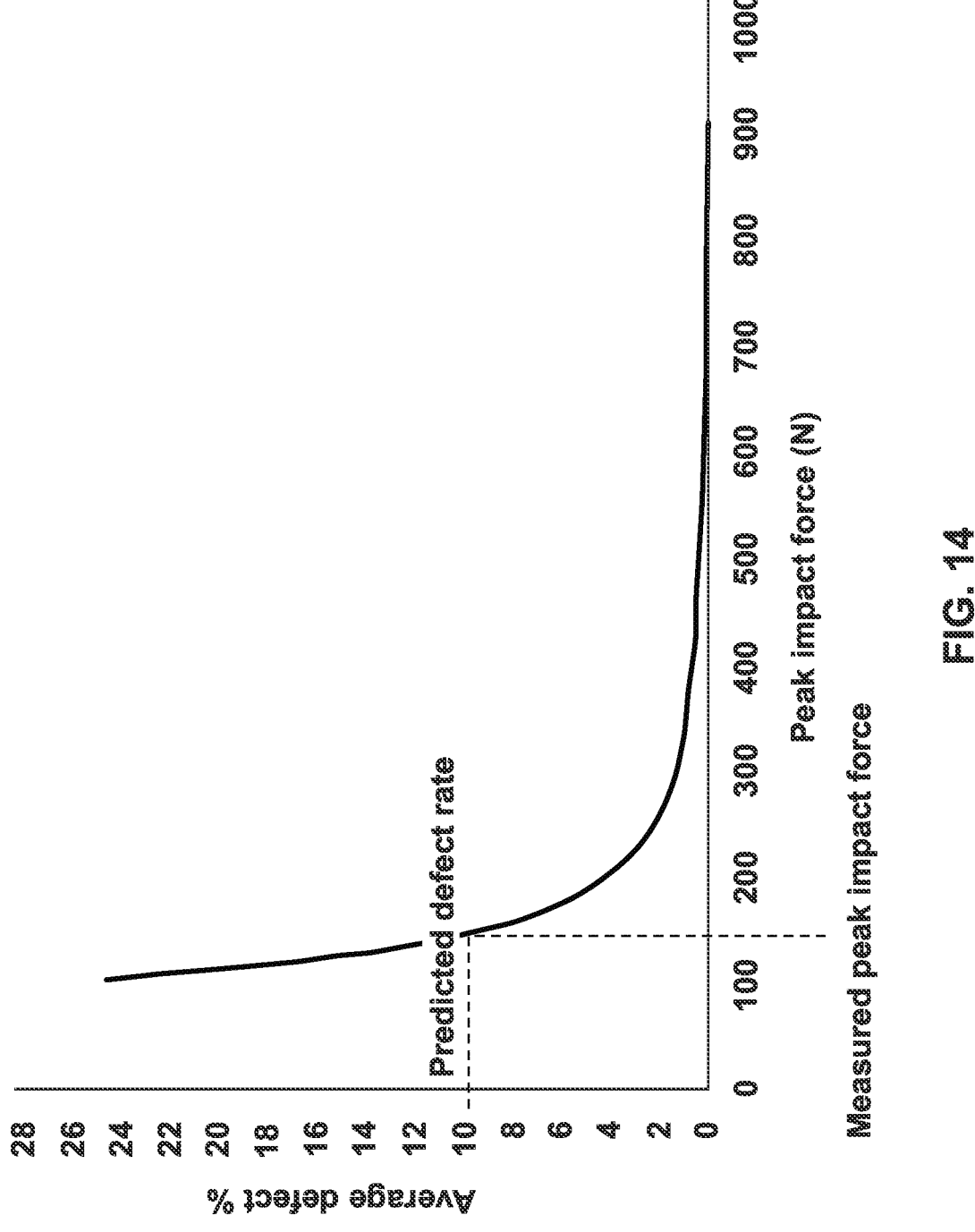
FIG. 14 illustrates the prediction of a physical defect rate based on a model which describes a relationship between physical defect rate and peak impact force according to an embodiment herein.

In an embodiment, at least one physical defect rate may be determined based on a stored model that describes a relationship between peak impact force values and physical defect rates, such as the model discussed above. For instance, the model may include or may be described by a curve or an equation that describes the relationship between peak impact force values and physical defect rate, such as the curve illustrated in FIG. 14. As discussed above, the peak impact force values may describe a peak amount of force imparted to a single tablet, or an average of peak amounts of force imparted to a set of tablets. In the example of FIG. 14, the at least one physical defect rate may be determined as a value on the curve which corresponds to the peak impact force determined in step 13002.

In an embodiment, the at least one predicted physical defect rate may include a first predicted physical defect rate that is associated with a specific circumstance in which tablets are dropped or can be dropped on a solid surface, such as when they are dropped five times and/or are dropped from a height of two meters. In some cases, the method 13000 may determine a plurality of predicted physical defect rates for a plurality of circumstances in which tablets are dropped or can be dropped onto a solid surface. For example, the plurality of predicted physical defect rates for the tablets may be associated with a plurality of different drop heights, a plurality of different drop counts, and/or a plurality of different combinations of drop height and drop count, from which the tablets can be dropped onto the solid surface. As stated above, making such predictions may in some instances involve extrapolating the predicted physical defect rates from intermediate physical defect rates.

In an embodiment, a method 13000 may involve determining, based on the peak impact force value, a predicted maximum height from which the tablets of the tablet type can be dropped without breaking or without the at least one predicted physical defect rate exceeding a predefined defect rate threshold, and/or a predicted maximum number of times by which the tablets of the tablet type can be dropped without breaking or without the at least one predicted physical defect rate exceeding a predefined defect rate threshold. Such a determination may be used to evaluate physical strength or robustness of a tablet or tablet's formulation, and/or whether the formulation needs to be adjusted to increase its physical strength.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A solid pharmaceutical dosage form testing apparatus, comprising:
  a striker component;
  an impact platform configured to provide an impact site;
  a housing within which the striker component and the impact platform are disposed, the housing including a mechanism configured to releasably suspend the striker component within the housing above the impact site;
  a sensor data acquisition system configured to obtain sensor data indicative of speed or kinetic energy of the striker component when the striker component is released so as to drop toward the impact site; and
  a solid dosage form placement mechanism having a first push component and a second push component that are coupled to the impact platform, wherein the first push component has a first recessed portion, the second push component has a second recessed portion, and the impact site is located between the first recessed portion of the first push component and the second recessed portion of the second push component,
  wherein a recess of the first recessed portion of the first push component inwardly extends toward an interior of the first push component away from the impact site,
  wherein a recess of the second recessed portion of the second push component inwardly extends toward an interior of the second push component away from the impact site, and
  wherein the first push component and the second push component are configured to be movable toward each other to position a solid dosage form disposed between the first recessed portion and the second recessed portion at the impact site.

2. The solid pharmaceutical dosage form testing apparatus of claim 1, wherein the first recessed portion forms a first concave corner and the second recessed portion forms a second concave corner, and wherein the first push component and the second push component are configured to surround the solid dosage form when the solid dosage form is disposed at the impact site.

3. The solid pharmaceutical dosage form testing apparatus of claim 1, wherein the first recessed portion forms a slot adapted to receive the second recessed portion when the first push component and the second push component are moved toward each other.

4. The solid pharmaceutical dosage form testing apparatus of claim 1, wherein the housing forms an impact chamber that surrounds the impact site for containing debris that is created during an impact strike test, and wherein the solid pharmaceutical dosage form testing apparatus further comprises at least one of: (i) an air flow generator configured to generate an air flow that applies air pressure into the impact chamber, or a vacuum configured to generate negative pressure for preventing the debris from leaving the impact chamber.

5. The solid pharmaceutical dosage form testing apparatus of claim 1, wherein the striker component has a rounded tip that faces the impact site.

6. The solid pharmaceutical dosage form testing apparatus of claim 1, wherein the striker component has a mass that is less than or equal to 1 kg.

7. The solid pharmaceutical dosage form testing apparatus of claim 6, wherein the striker component has a mass that is less than or equal to 0.5 kg.

8. The solid pharmaceutical dosage form testing apparatus of claim 1, wherein the housing has a height which limits a maximum distance by which the striker component is releasably suspended above the impact site to less than or equal to 120 cm, 110 cm, 100 cm, 90 cm, 80 cm, 70 cm, 60 cm, 50 cm, 40 cm, 30 cm, 20 cm, 10 cm, 5 cm, or less.

\* \* \* \* \*